(12) United States Patent
Errico et al.

(10) Patent No.: US 7,258,699 B2
(45) Date of Patent: *Aug. 21, 2007

(54) ARTIFICIAL INTERVERTEBRAL DISC HAVING A CAPTURED BALL AND SOCKET JOINT WITH A SOLID BALL AND RETAINING CAP

(75) Inventors: Joseph P. Errico, Kirkland, WA (US); Michael W. Dudasik, Nutley, NJ (US); Rafail Zubok, Midland Park, NJ (US)

(73) Assignee: SpineCore, Inc., Summit, NJ (US)

( * ) Notice: Subject to any disclaimer, the term of this patent is extended or adjusted under 35 U.S.C. 154(b) by 279 days.

This patent is subject to a terminal disclaimer.

(21) Appl. No.: 10/294,983

(22) Filed: Nov. 14, 2002

(65) Prior Publication Data

US 2003/0074069 A1    Apr. 17, 2003

Related U.S. Application Data

(63) Continuation of application No. 10/256,160, filed on Sep. 26, 2002, which is a continuation-in-part of application No. 10/175,417, filed on Jun. 19, 2002, which is a continuation-in-part of application No. 10/151,280, filed on May 20, 2002, and a continuation-in-part of application No. 10/140,153, filed on May 7, 2002, and a continuation-in-part of application No. 10/128,619, filed on Apr. 23, 2002, now Pat. No. 6,863,689, and a continuation-in-part of application No. 09/982,148, filed on Oct. 18, 2001, now Pat. No. 6,673,113, which is a continuation-in-part of application No. 09/970,479, filed on Oct. 4, 2001, now Pat. No. 6,669,730, which is a continuation-in-part of application No. 09/968,046, filed on Oct. 1, 2001, now abandoned, which is a continuation-in-part of application No. 09/906,119, filed on Jul. 16, 2001, now Pat. No. 6,607,559.

(51) Int. Cl.
*A61F 2/44* (2006.01)

(52) U.S. Cl. .................. 623/17.14; 623/17.15

(58) Field of Classification Search ............. 623/17.14, 623/17.15, 17.16, 17.13; 606/61
See application file for complete search history.

(56) References Cited

U.S. PATENT DOCUMENTS

| | | |
|---|---|---|
| 3,867,728 A | 2/1975 | Stubstad et al. |
| 4,309,777 A | 1/1982 | Patil |
| 4,605,417 A | 8/1986 | Fleischauer |
| 4,759,766 A | 7/1988 | Buettner-Janz et al. |

(Continued)

*Primary Examiner*—Brian E. Pellegrino
(74) *Attorney, Agent, or Firm*—Lerner, David, Littenberg, Krumholz & Mentlik, LLP

(57) ABSTRACT

An artificial disc having a pair of opposing baseplates, for seating against opposing vertebral bone surfaces, separated by a ball and socket joint that includes a solid ball mounted to protrude from one of the baseplates. The ball is captured within a curvate socket formed in a peak of a convex structure integral with the other of the baseplates. The socket is formed by opposing curvate pockets, one on the convex structure and one on a retaining cap that is secured to the other of the baseplates. The ball rotates and angulates in the socket. The ball and socket joint therefore permits the baseplates to rotate and angulate relative to one another.

11 Claims, 42 Drawing Sheets

A-A

U.S. PATENT DOCUMENTS

| | | | |
|---|---|---|---|
| 4,759,769 A | 7/1988 | Hedman et al. | |
| 4,932,969 A | 6/1990 | Frey et al. | |
| 4,997,432 A | 3/1991 | Keller | |
| 5,236,460 A | 8/1993 | Barber | |
| 5,314,477 A | 5/1994 | Marnay | |
| 5,370,697 A | 12/1994 | Baumgartner | |
| 5,401,269 A | 3/1995 | Buttner-Janz et al. | |
| 5,425,773 A | 6/1995 | Boyd et al. | |
| 5,507,816 A | 4/1996 | Bullivant | |
| 5,556,431 A | 9/1996 | Buttner-Janz | |
| 5,562,738 A | 10/1996 | Boyd et al. | |
| 5,676,701 A | 10/1997 | Yuan et al. | |
| 5,683,465 A | 11/1997 | Shinn et al. | |
| 5,782,832 A | 7/1998 | Larsen et al. | |
| 5,893,889 A * | 4/1999 | Harrington | 623/17.16 |
| 5,895,428 A | 4/1999 | Berry | |
| 5,899,941 A | 5/1999 | Nishijima | |
| 5,989,291 A | 11/1999 | Ralph et al. | |
| 6,039,763 A | 3/2000 | Shelokov | |
| 6,368,350 B1 | 4/2002 | Erickson et al. | |
| 6,375,682 B1 | 4/2002 | Fleischmann et al. | |
| 6,517,580 B1 | 2/2003 | Ramadan et al. | |
| 6,582,468 B1 | 6/2003 | Gauchet | |
| 6,610,092 B2 | 8/2003 | Ralph et al. | |
| 6,645,249 B2 | 11/2003 | Ralph et al. | |
| 6,673,113 B2 | 1/2004 | Ralph et al. | |
| 6,682,562 B2 | 1/2004 | Viart et al. | |
| 6,706,068 B2 | 3/2004 | Ferree | |
| 2001/0016773 A1 | 8/2001 | Serhan et al. | |
| 2002/0111681 A1 | 8/2002 | Ralph et al. | |
| 2003/0014110 A1 | 1/2003 | Ralph et al. | |
| 2003/0014112 A1 | 1/2003 | Ralph et al. | |
| 2003/0028249 A1 | 2/2003 | Baccelli et al. | |
| 2003/0055503 A1 | 3/2003 | O'Neil | |
| 2003/0060886 A1 | 3/2003 | Van Hoeck et al. | |
| 2003/0069586 A1 | 4/2003 | Errico et al. | |
| 2003/0069642 A1 | 4/2003 | Ralph et al. | |
| 2003/0074067 A1 | 4/2003 | Errico et al. | |
| 2003/0149482 A1 | 8/2003 | Michelson | |
| 2003/0204260 A1 | 10/2003 | Ferree | |
| 2003/0208271 A1 | 11/2003 | Kuras | |
| 2003/0233097 A1 | 12/2003 | Ferree | |
| 2003/0233148 A1 | 12/2003 | Ferree | |
| 2004/0002759 A1 | 1/2004 | Ferree | |
| 2004/0002762 A1 | 1/2004 | Hawkins | |
| 2004/0030389 A1 | 2/2004 | Ferree | |
| 2004/0030390 A1 | 2/2004 | Ferree | |
| 2004/0034426 A1 | 2/2004 | Errico et al. | |
| 2004/0078079 A1 | 4/2004 | Foley | |

* cited by examiner

B-B

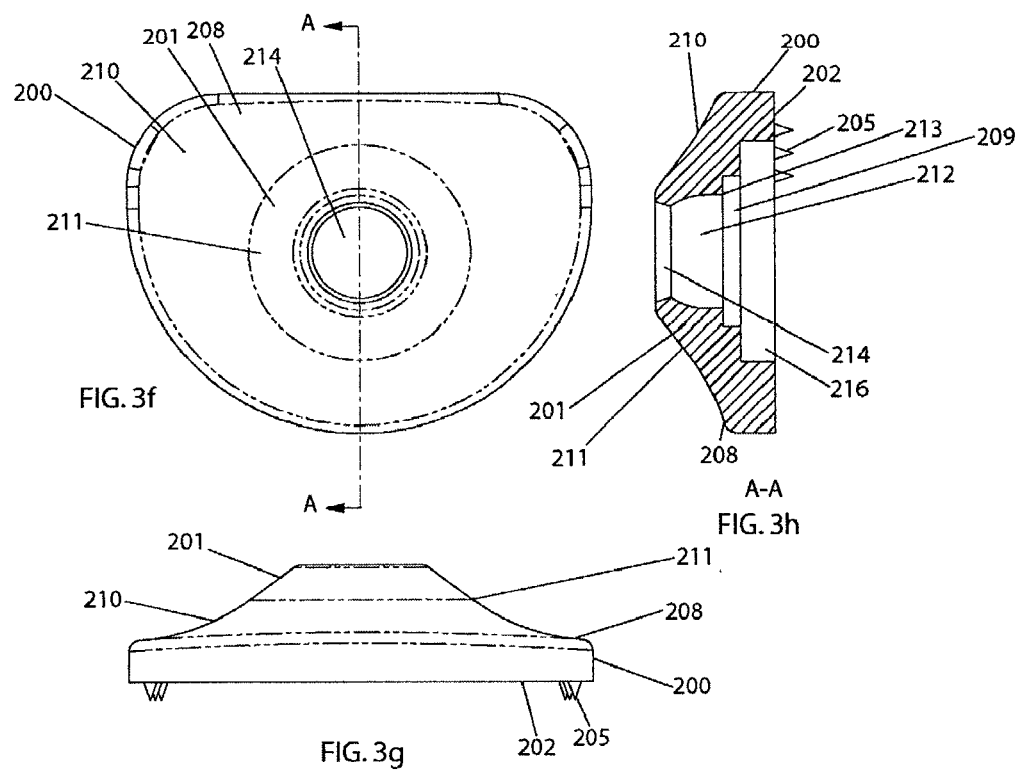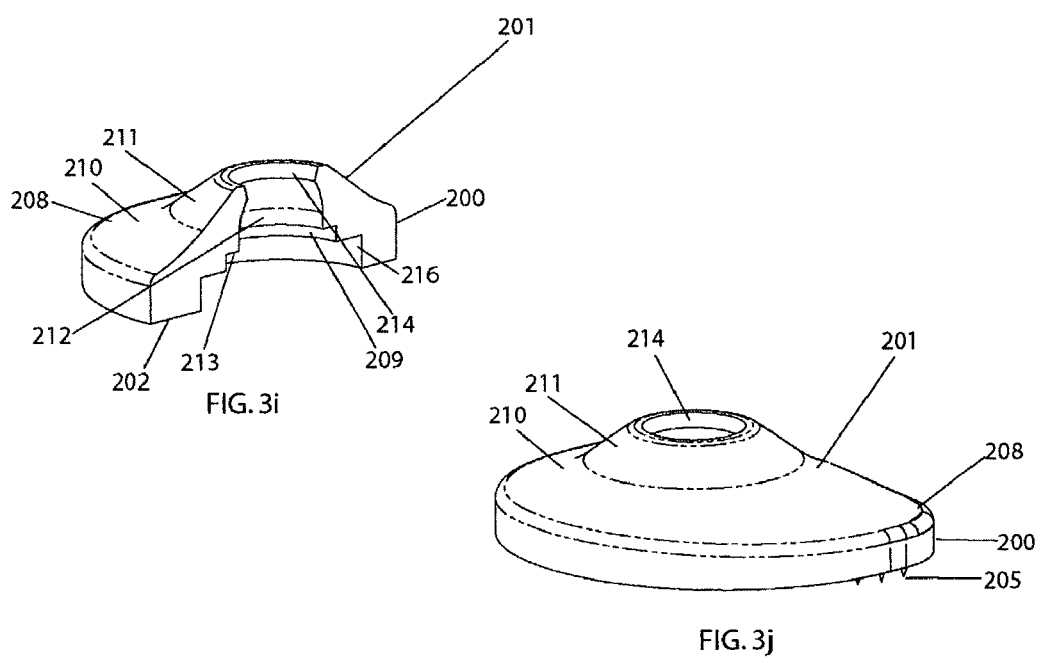

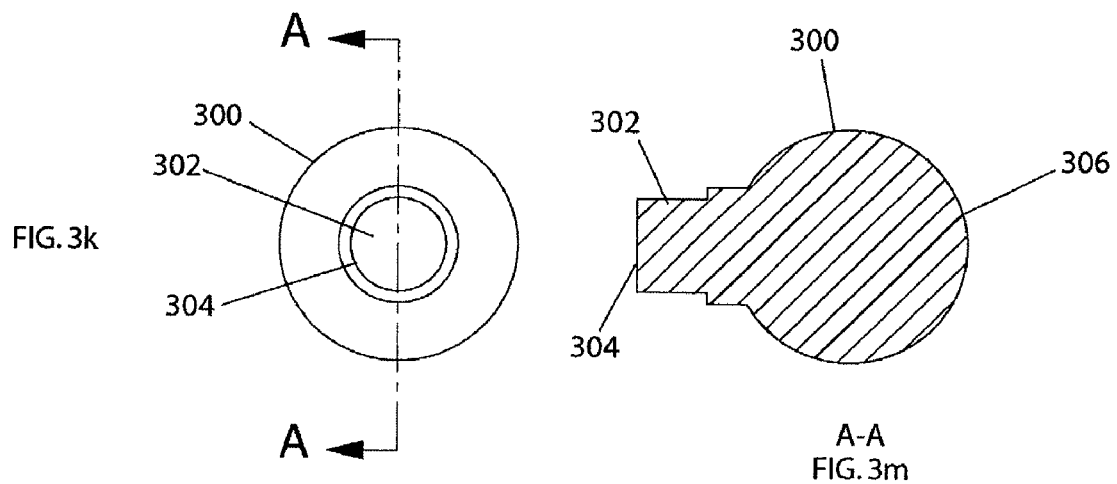
FIG. 3k
A-A
FIG. 3m
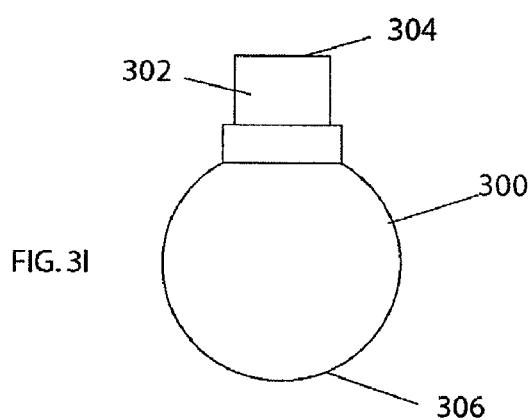
FIG. 3l
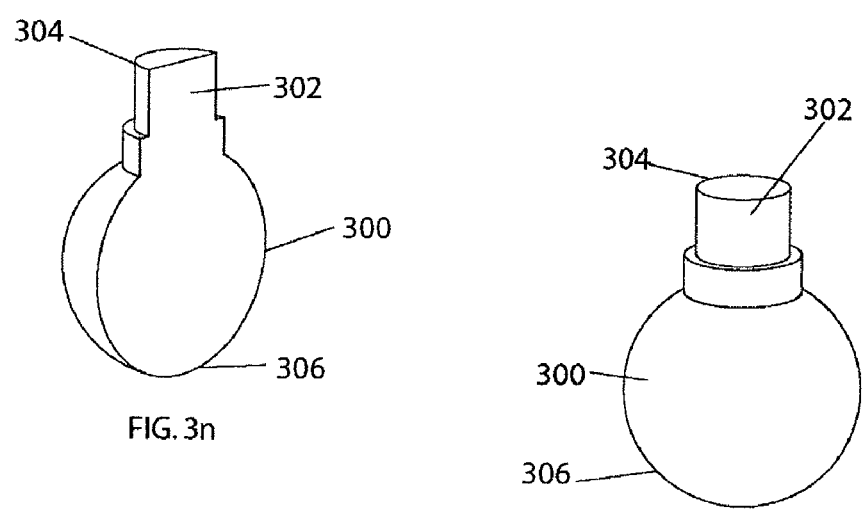
FIG. 3n
FIG. 3o

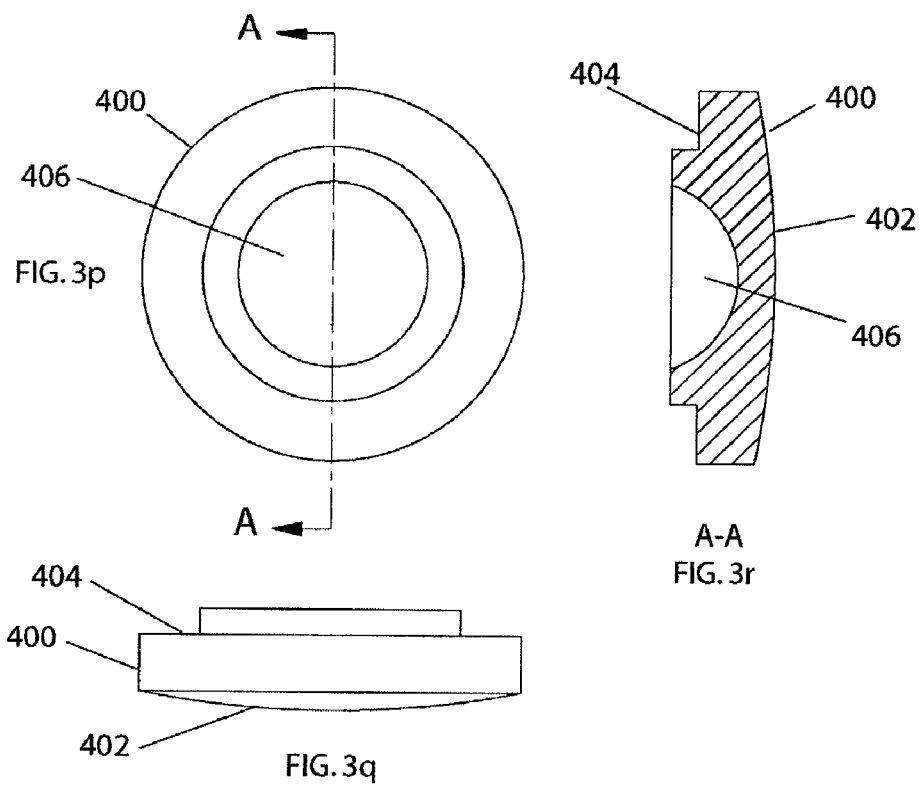
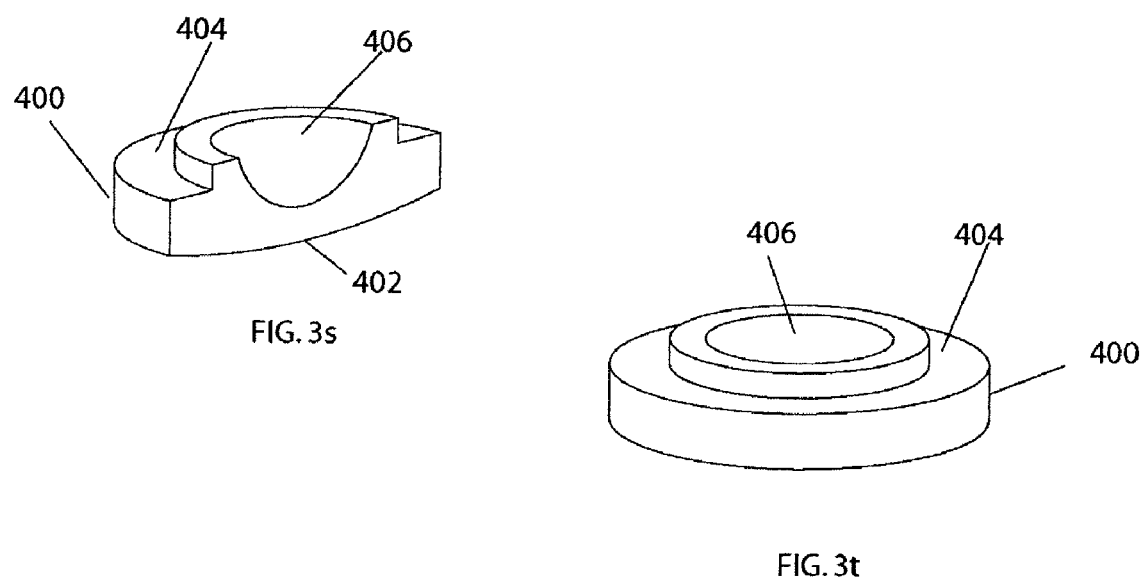

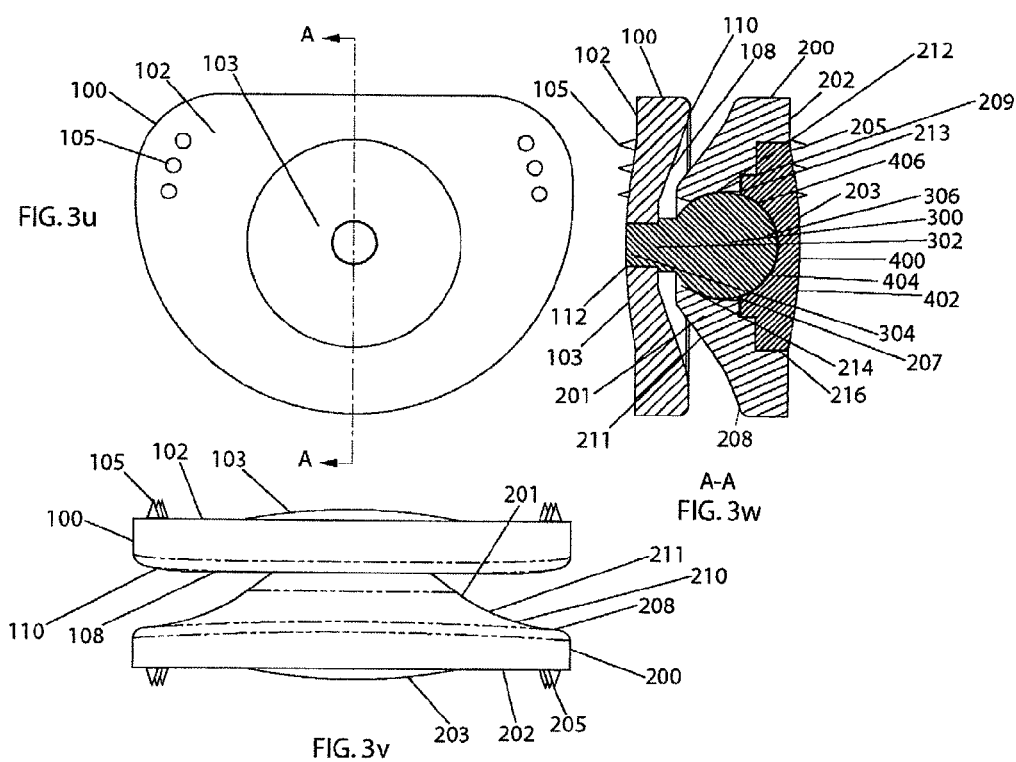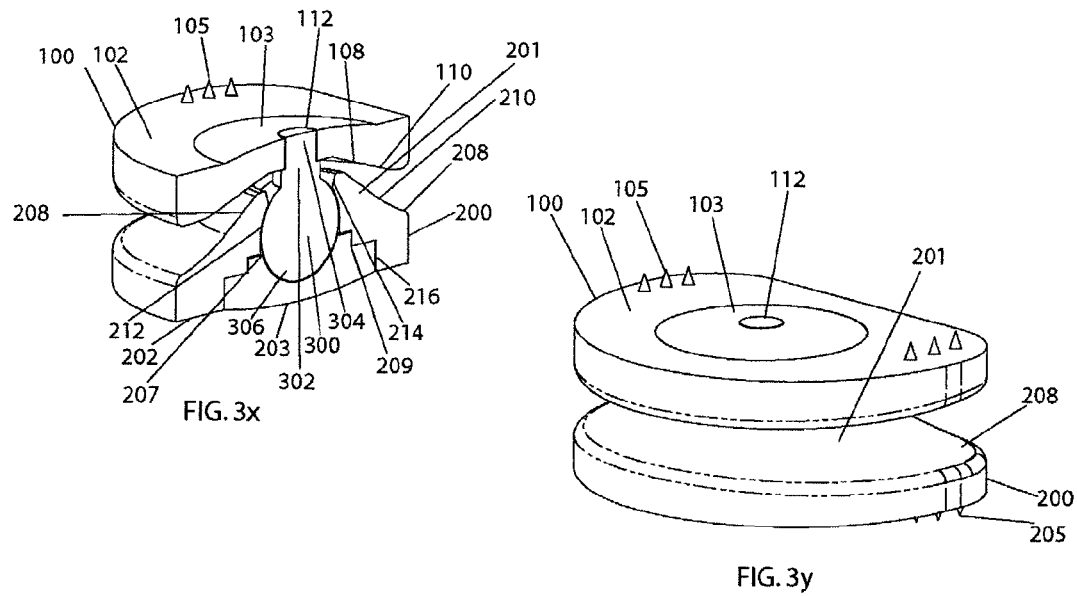

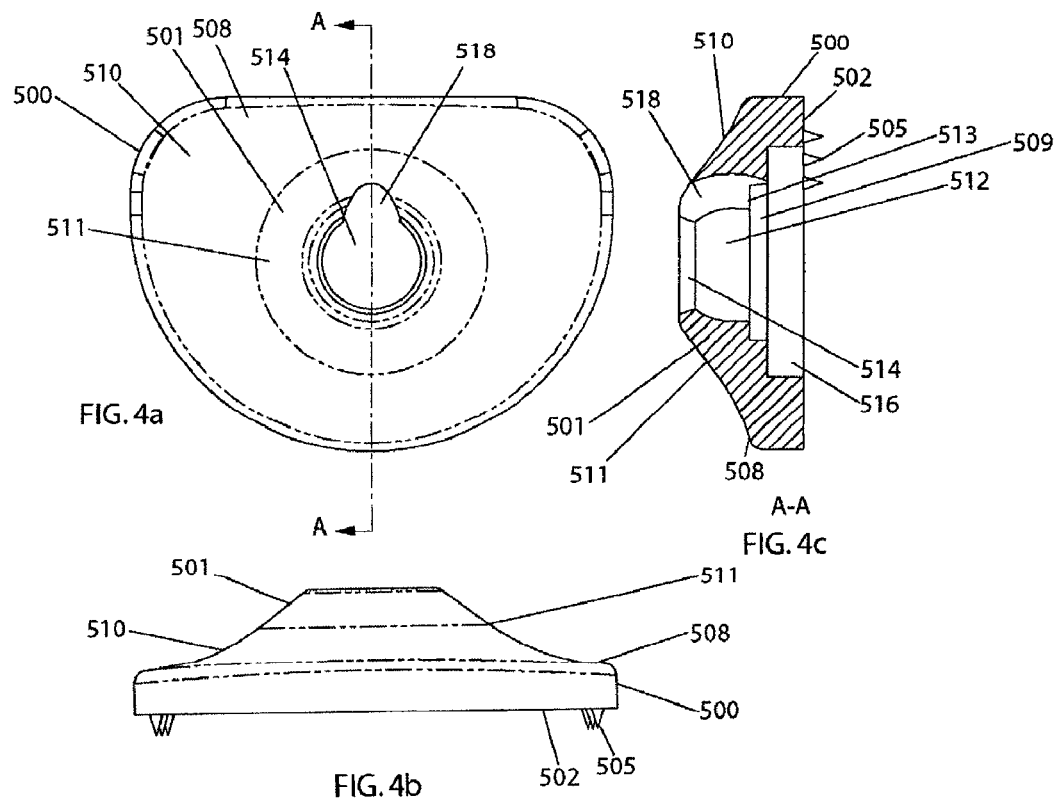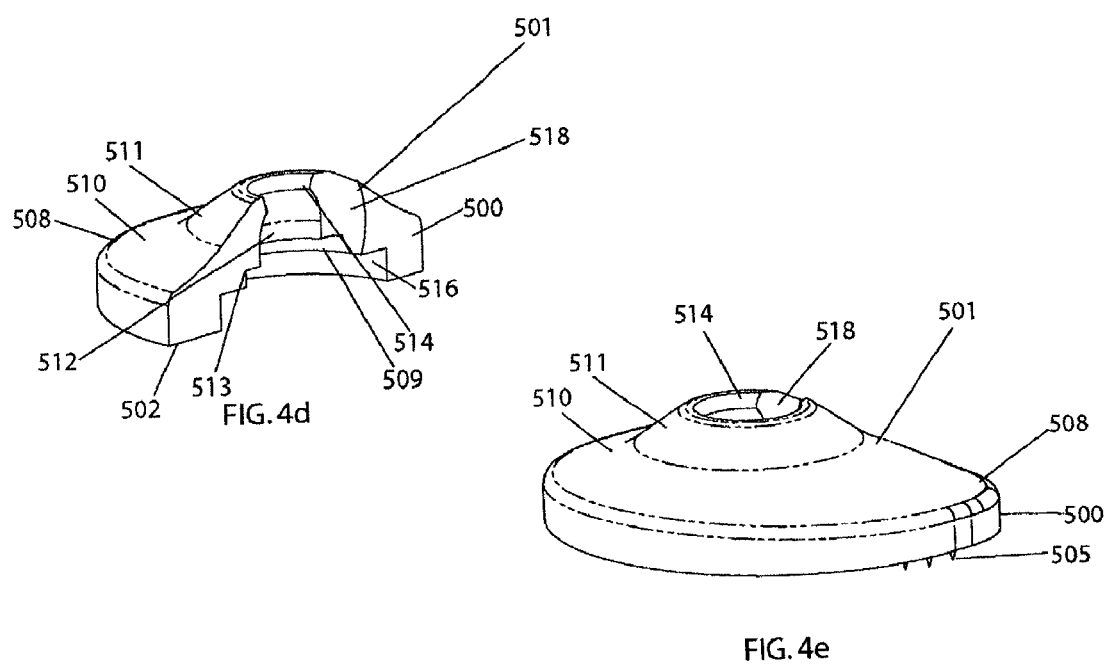

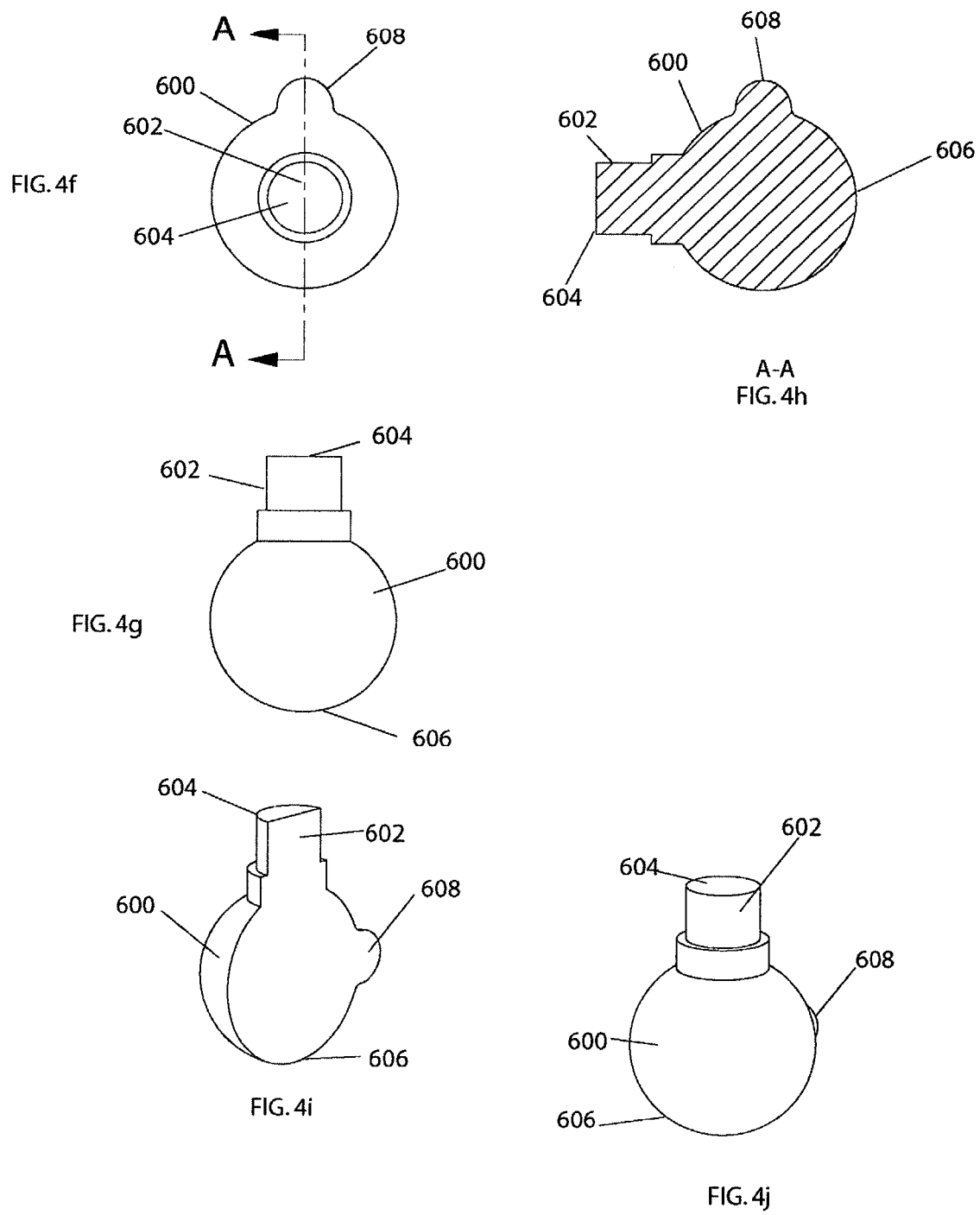

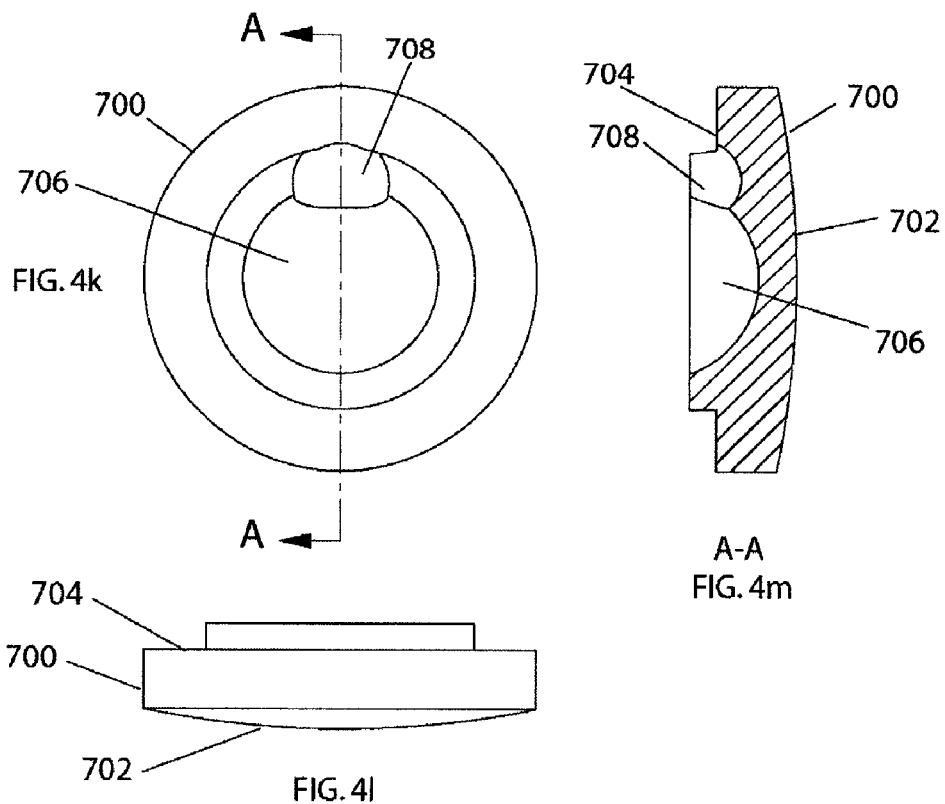
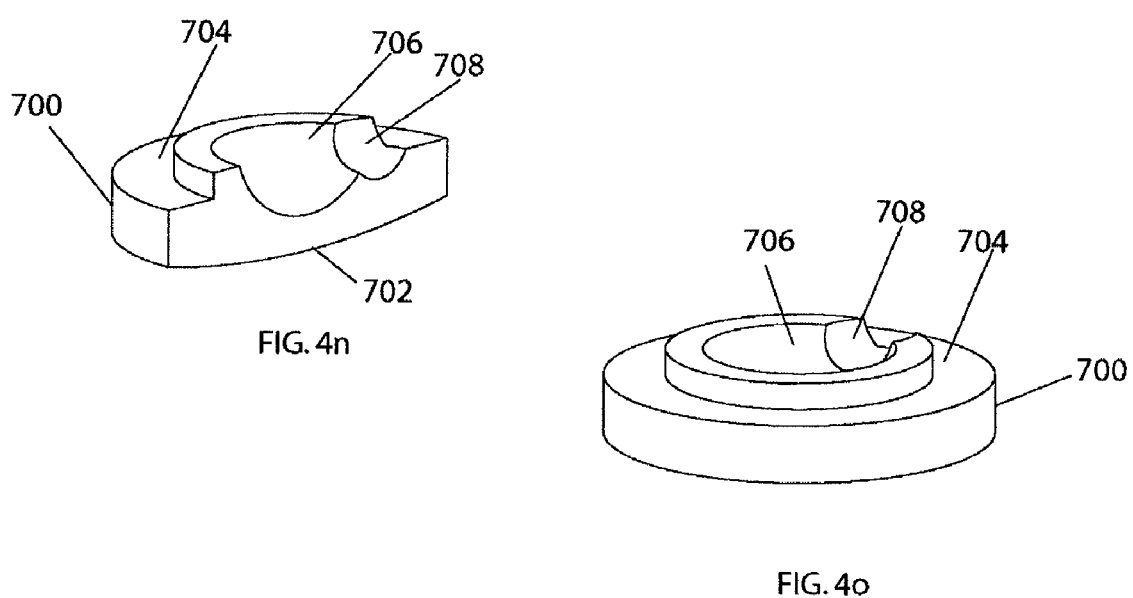
FIG. 4k
FIG. 4l
A-A FIG. 4m
FIG. 4n
FIG. 4o

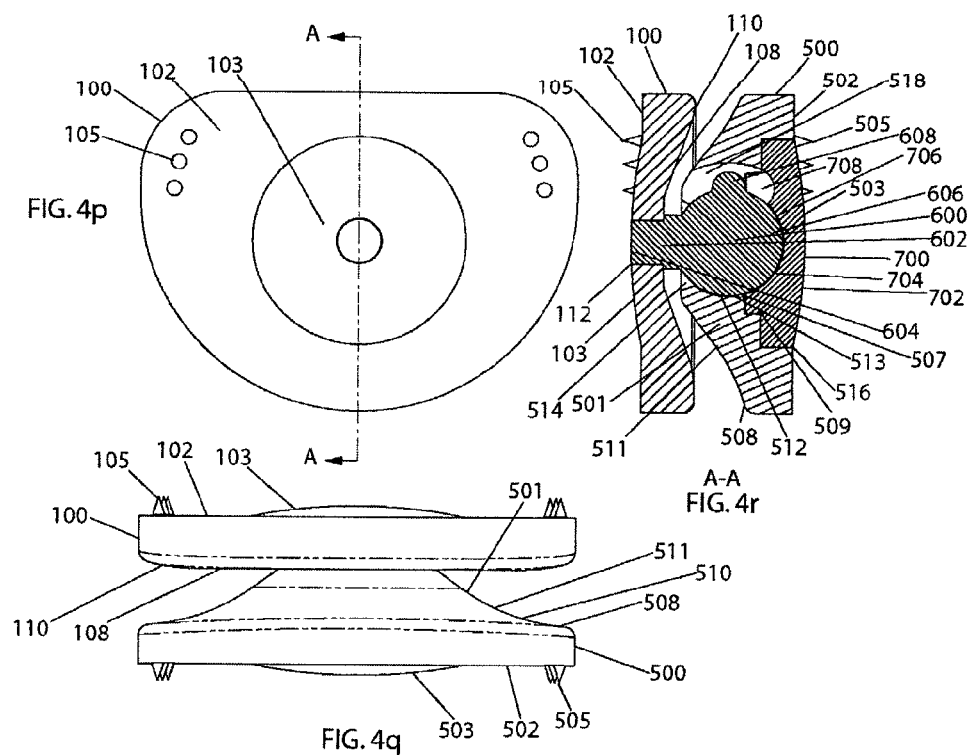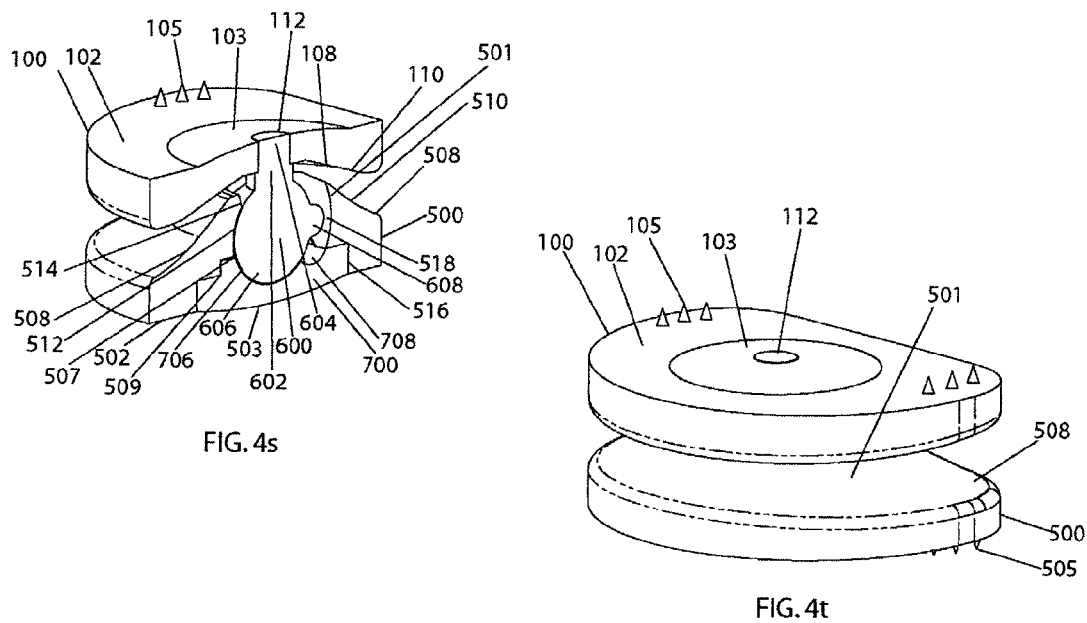

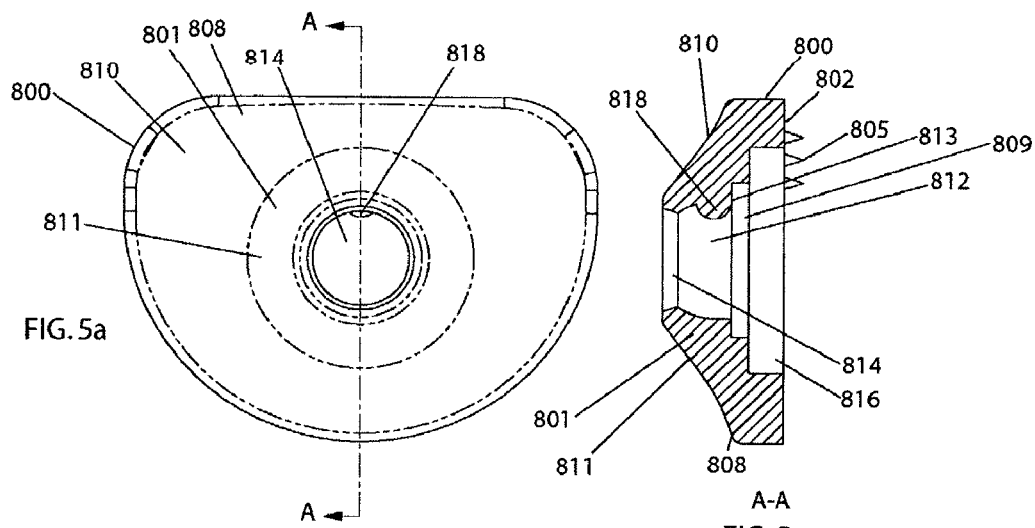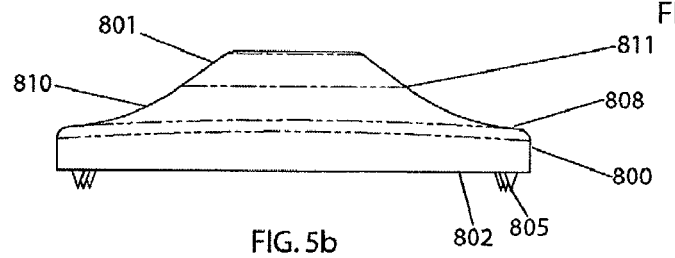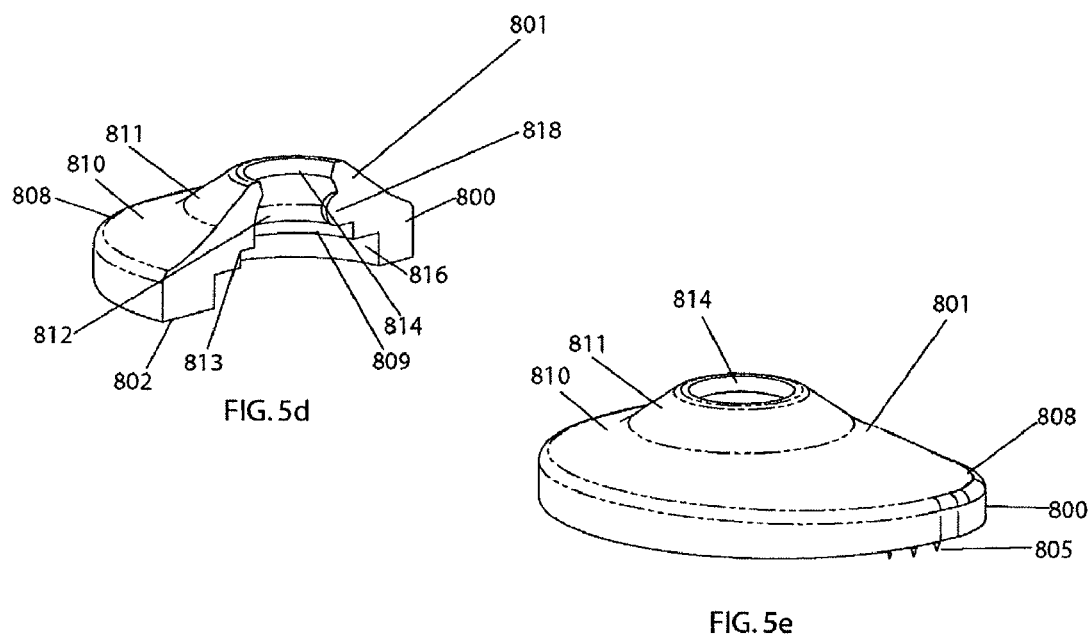

A-A

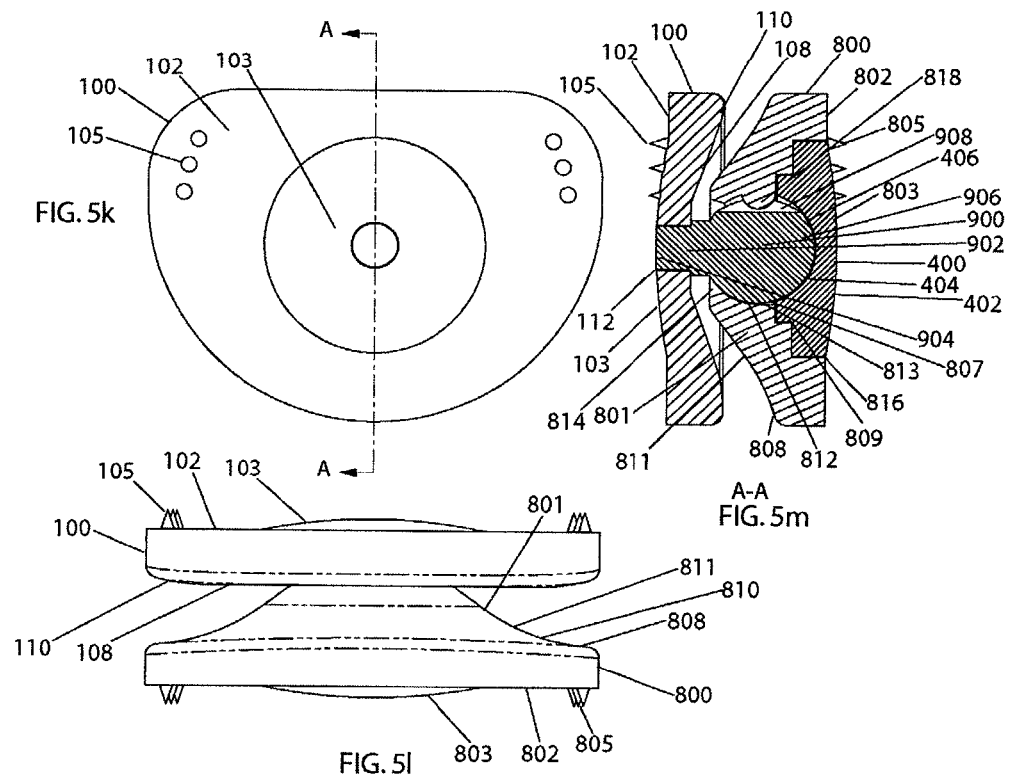
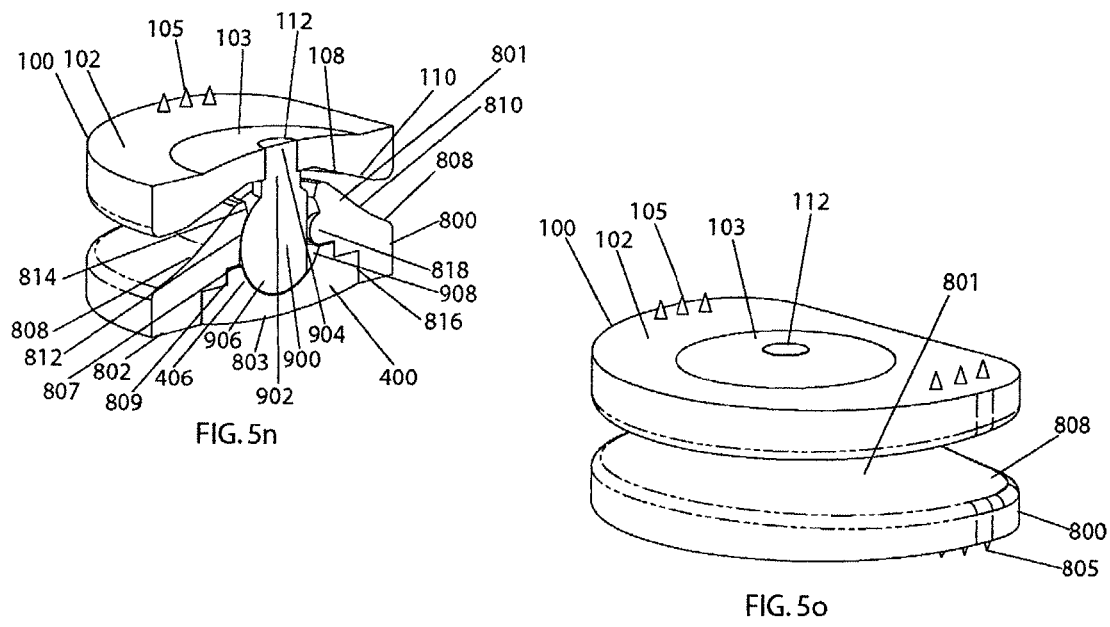

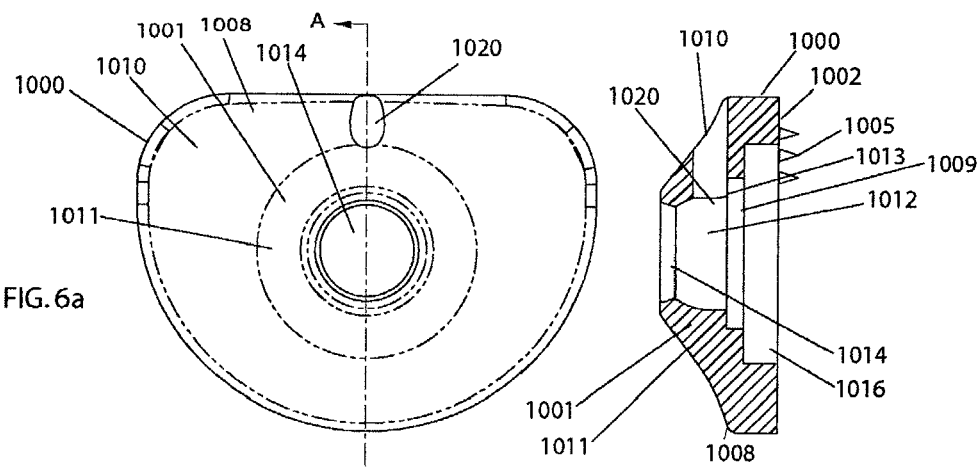
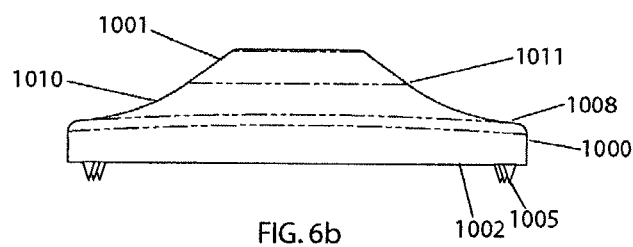
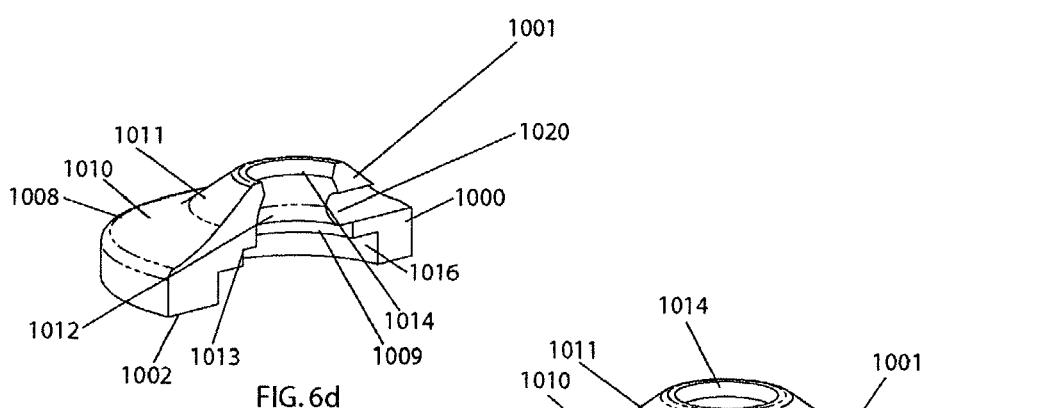
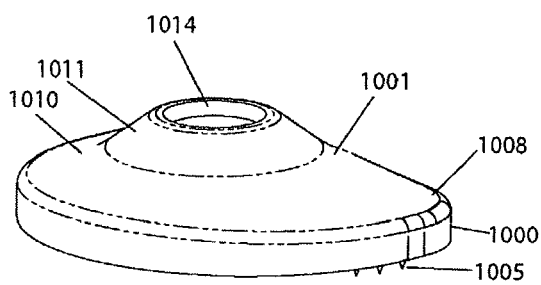

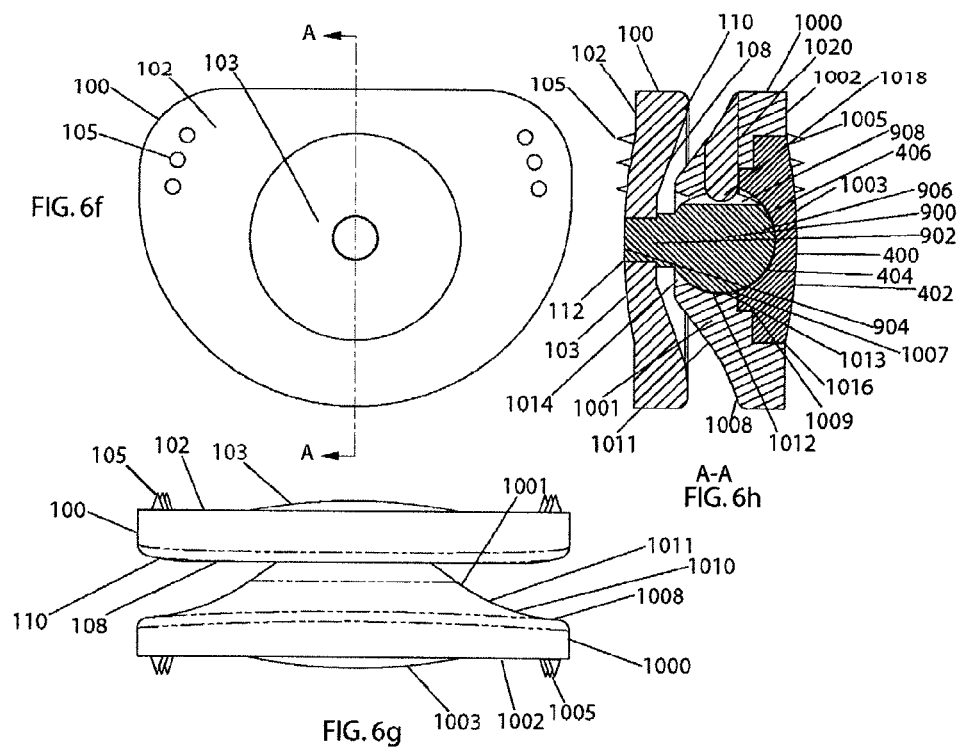
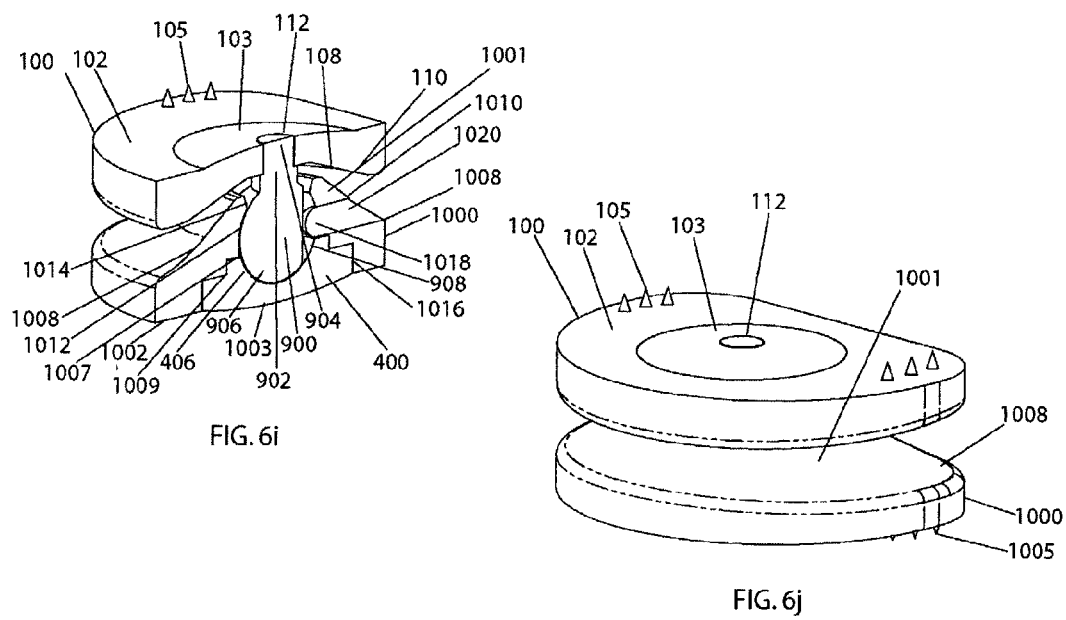

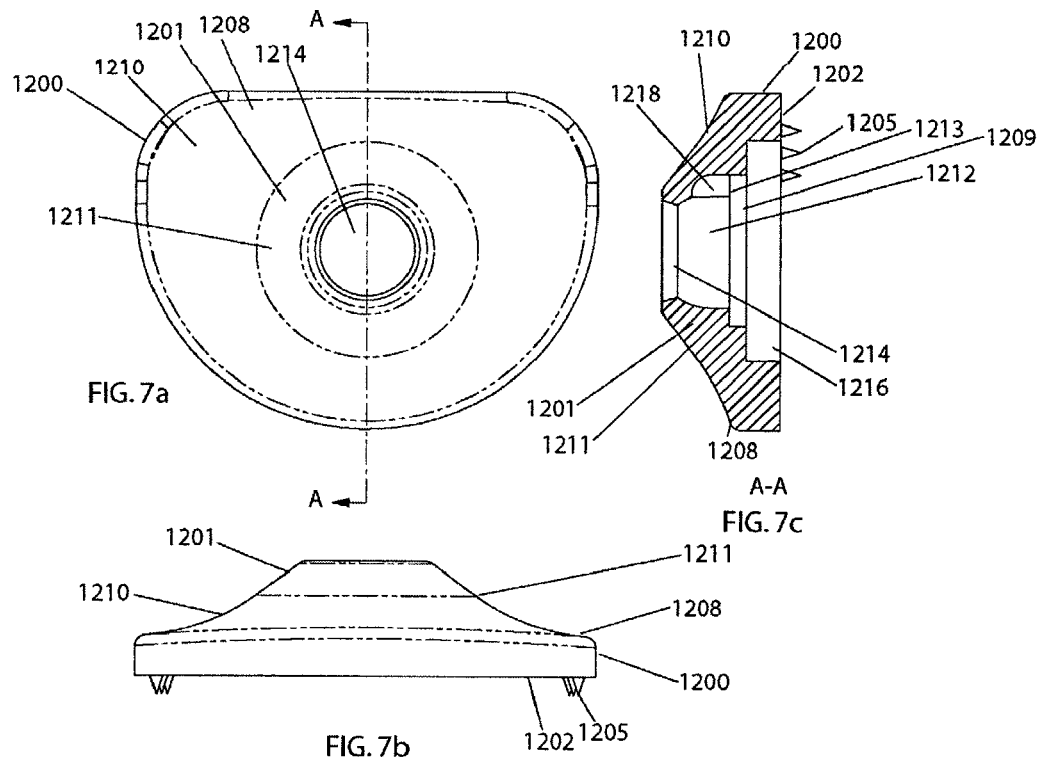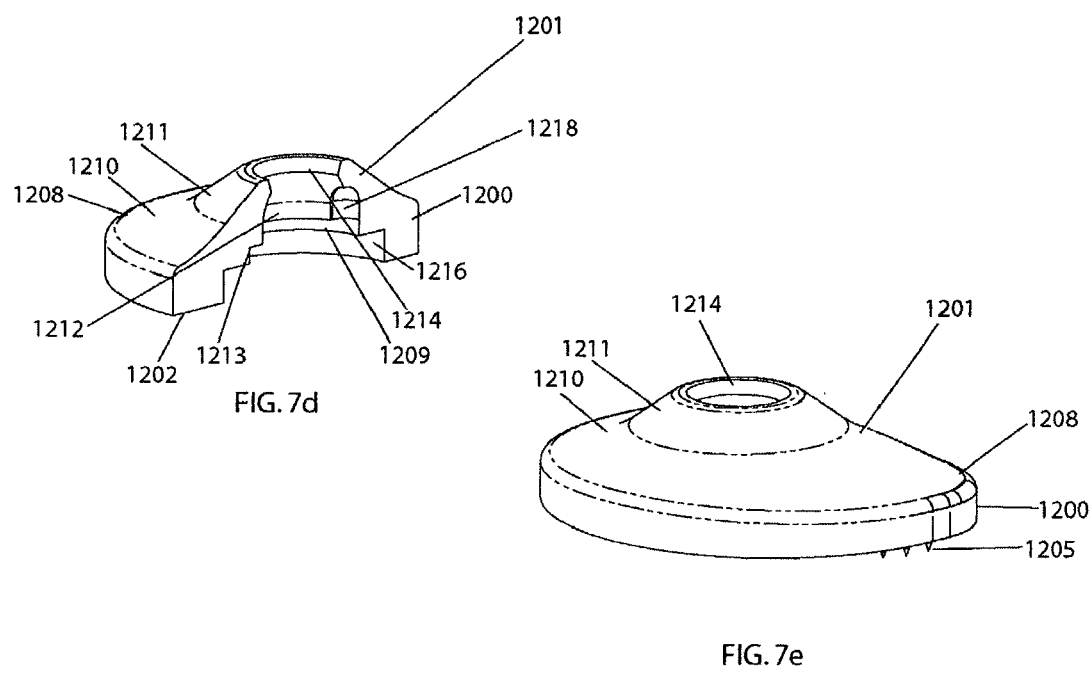

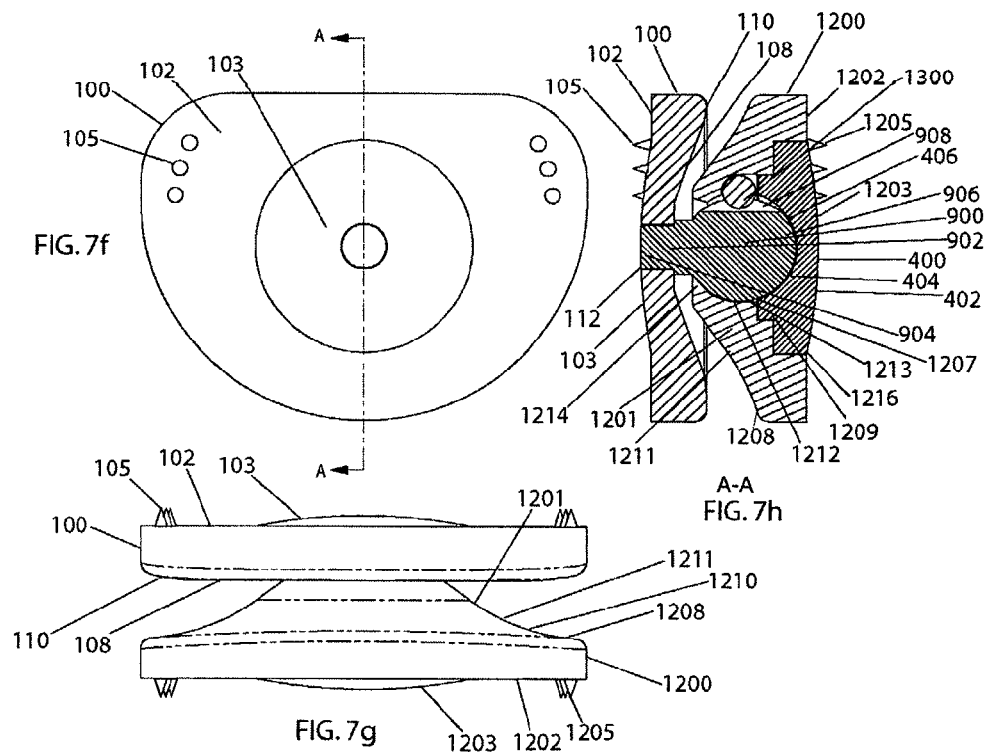
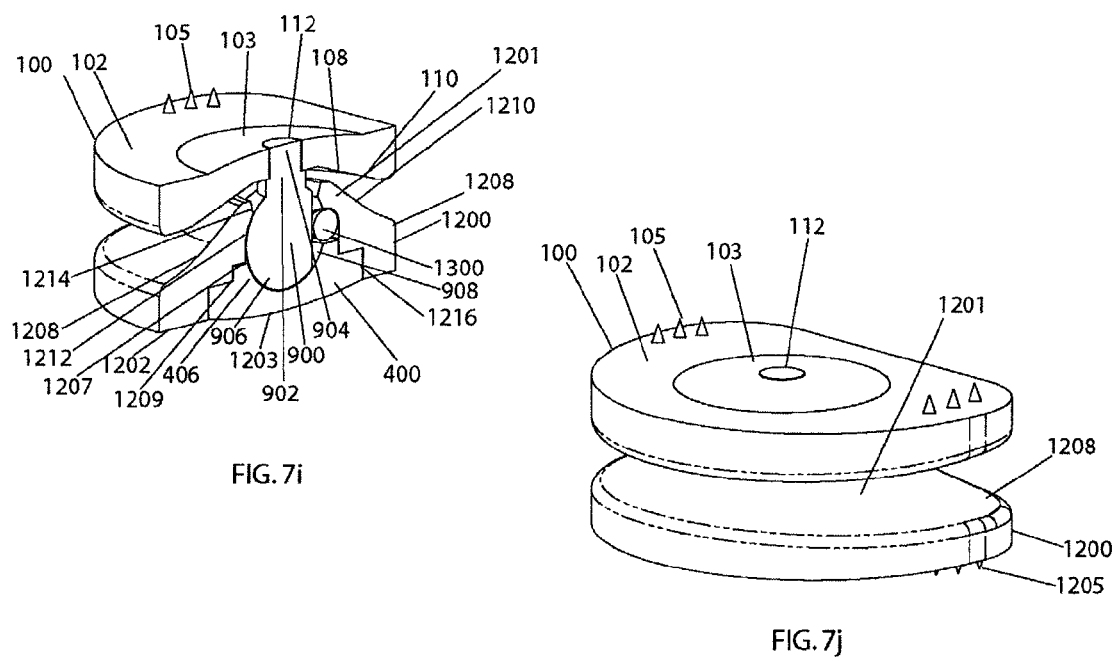

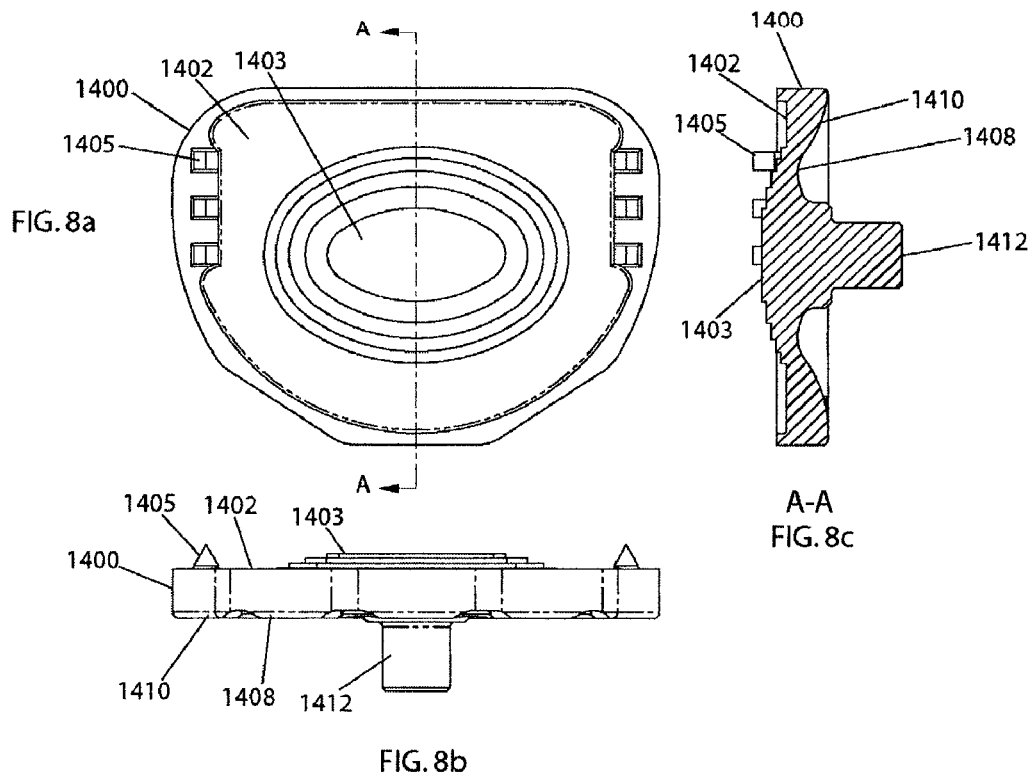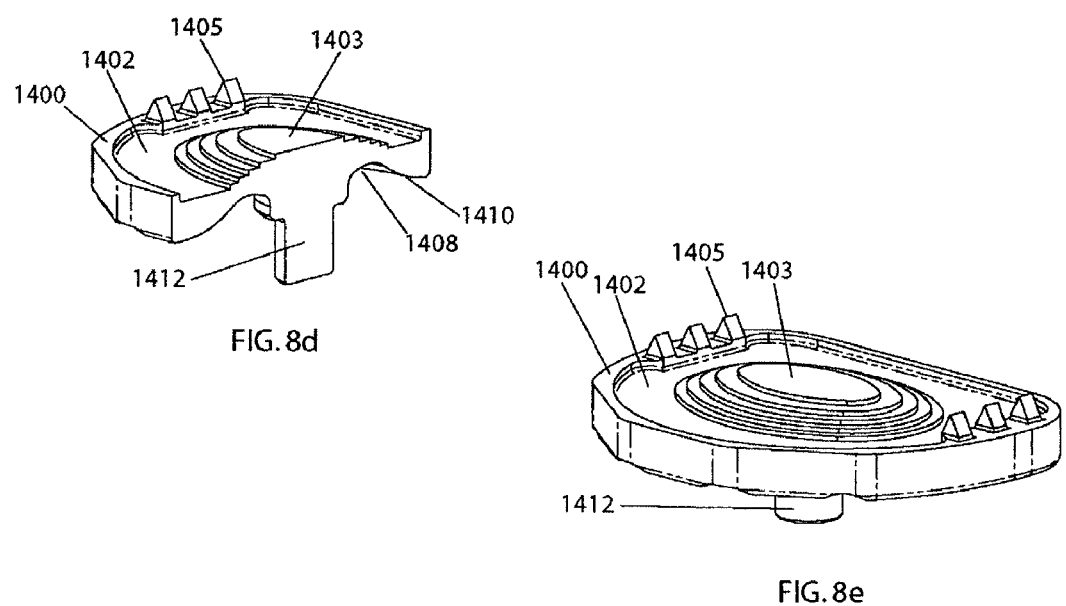

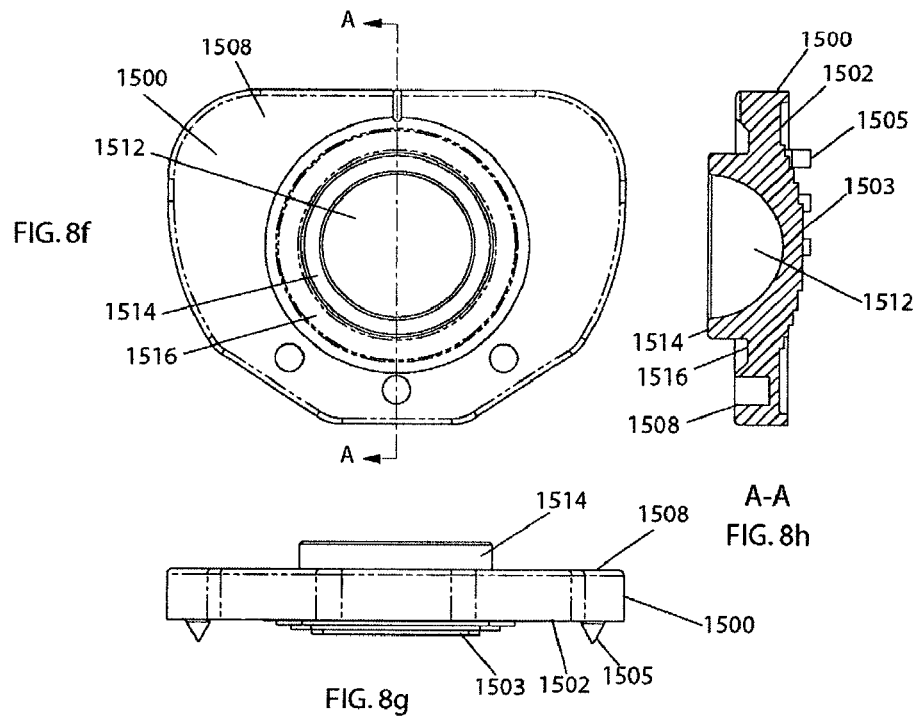
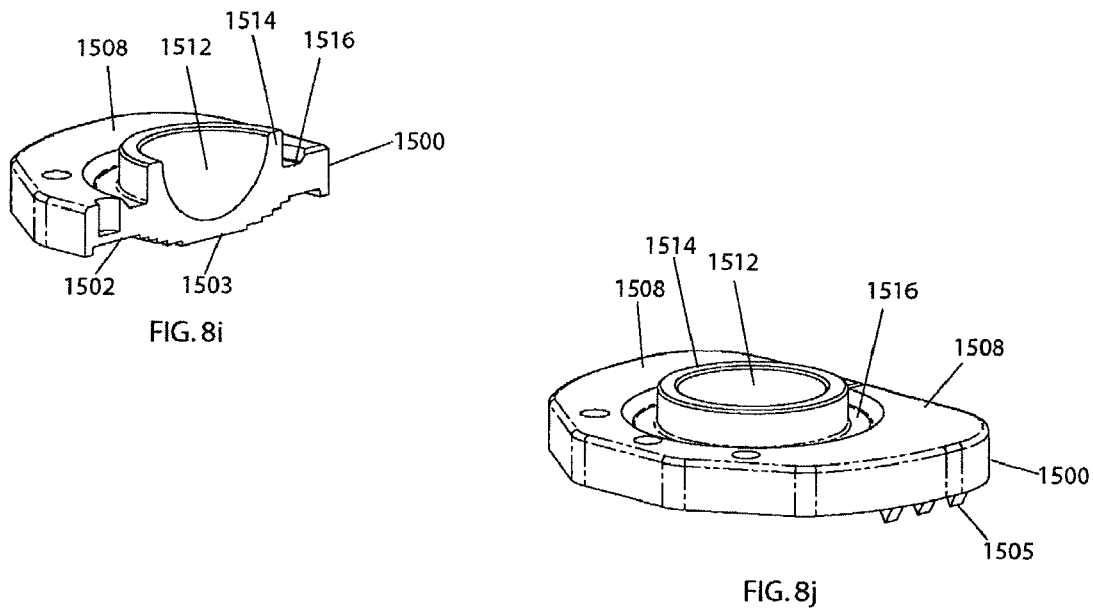

A-A

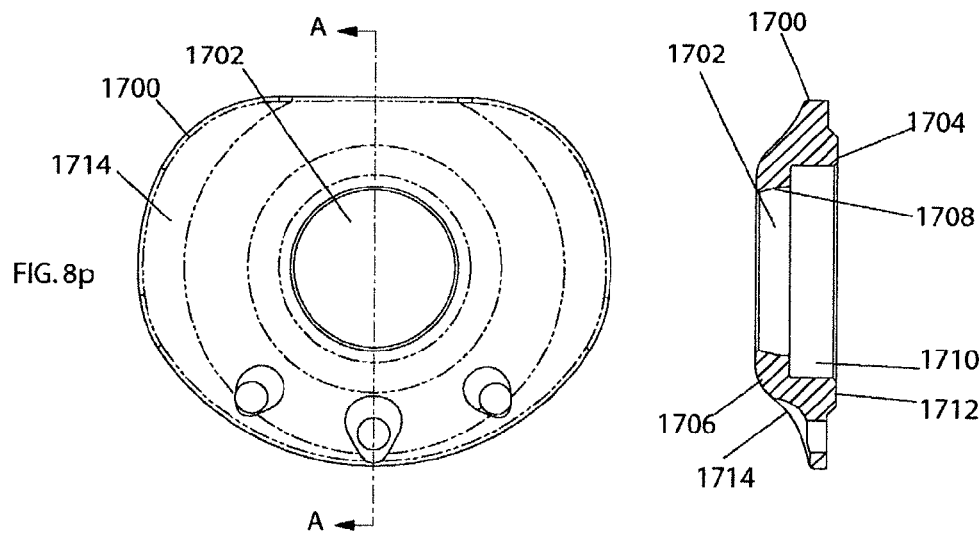
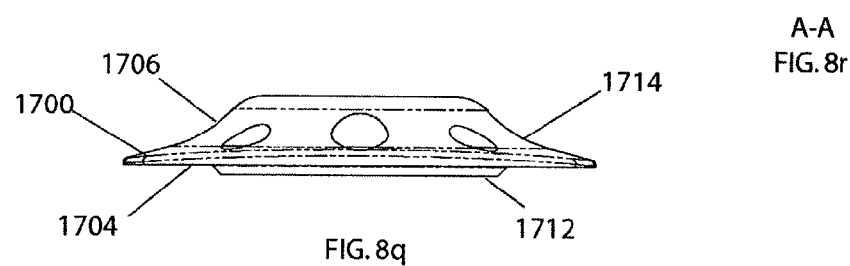
FIG. 8p
FIG. 8q
A-A FIG. 8r
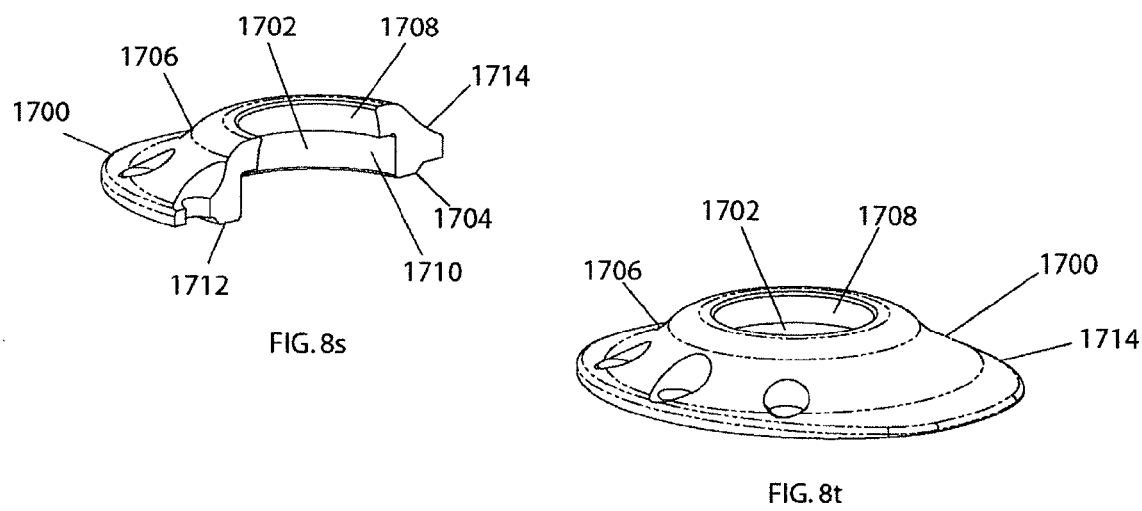
FIG. 8s
FIG. 8t

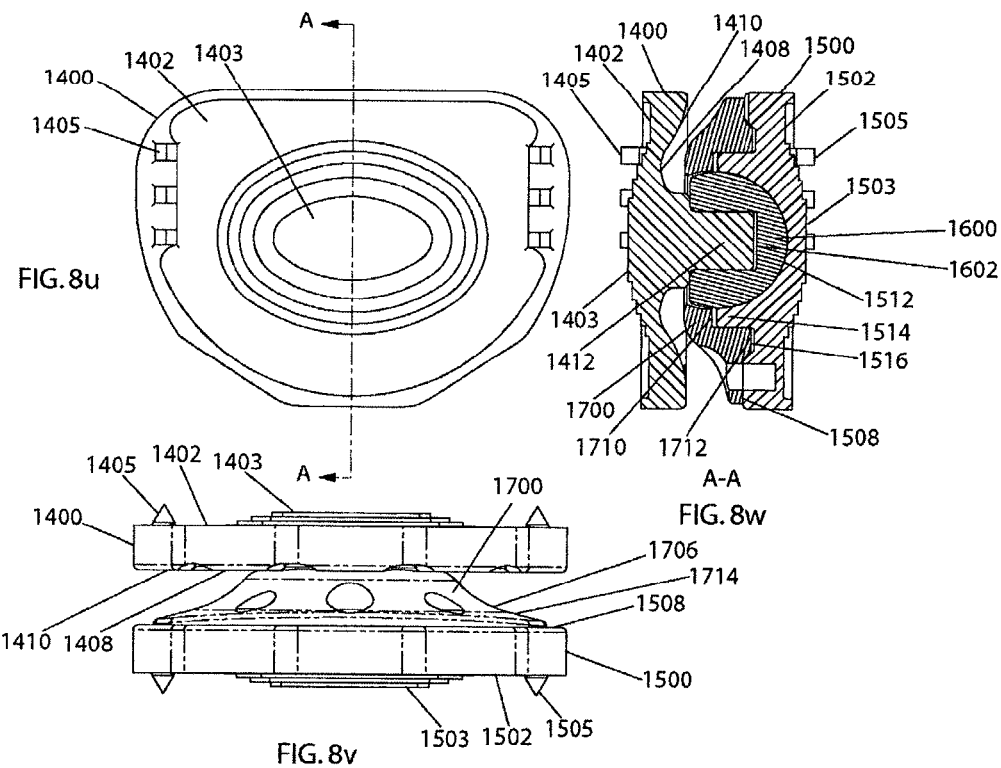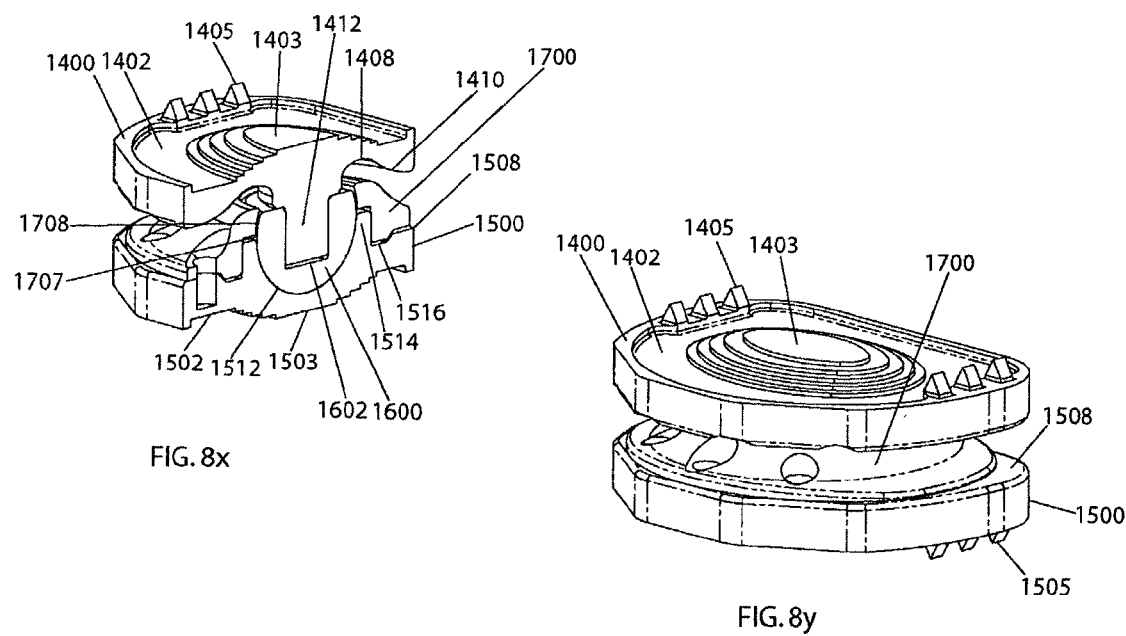

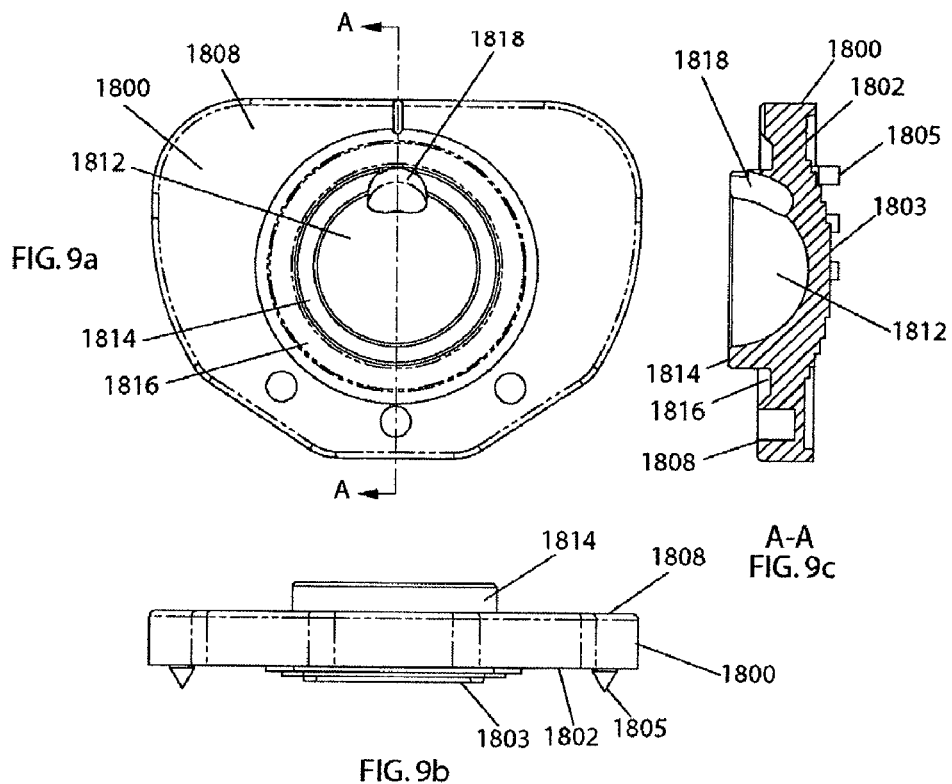
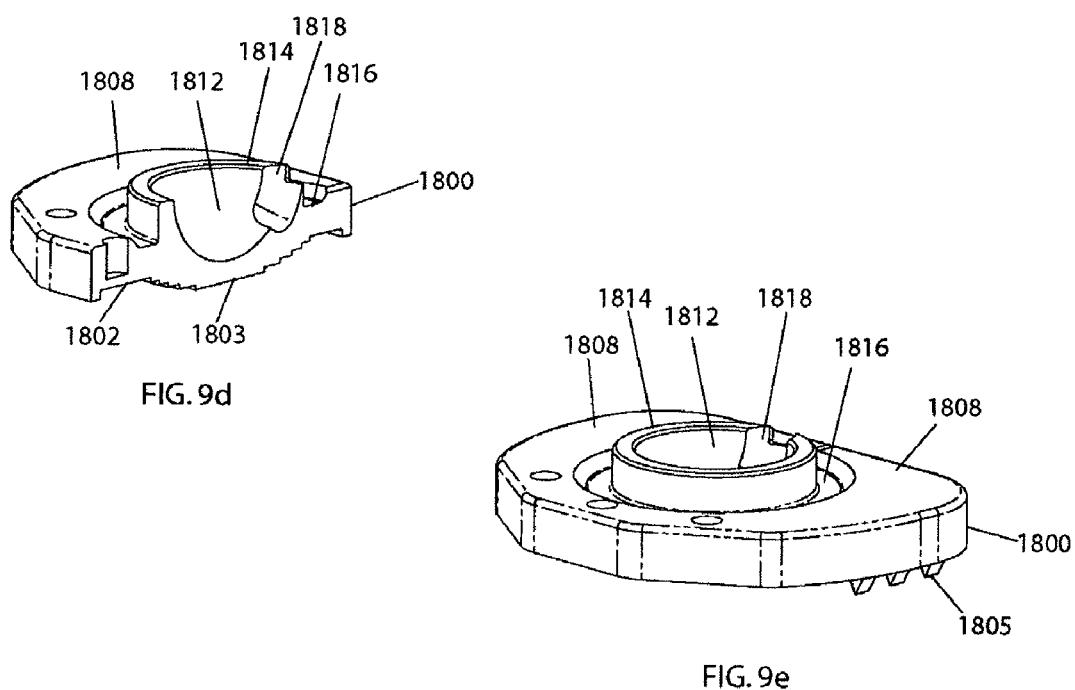

A-A

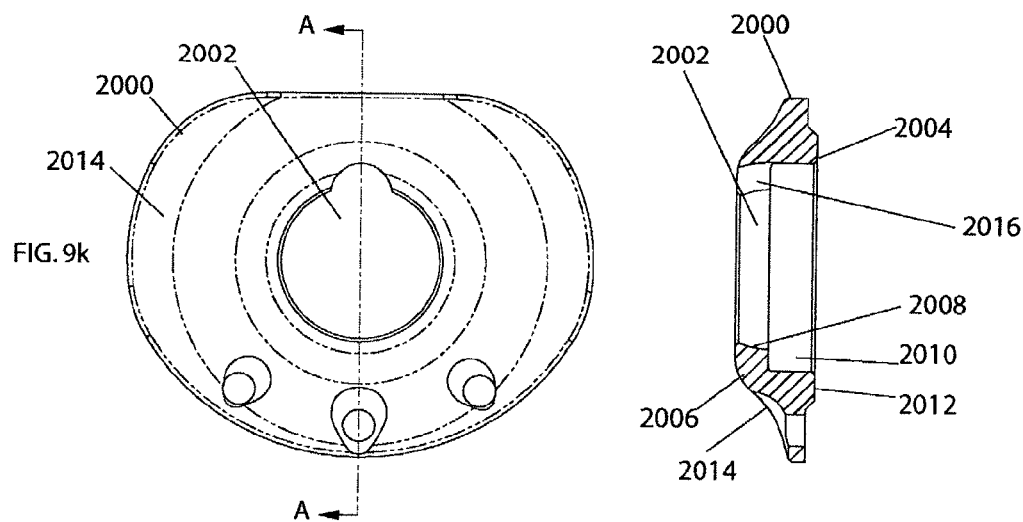
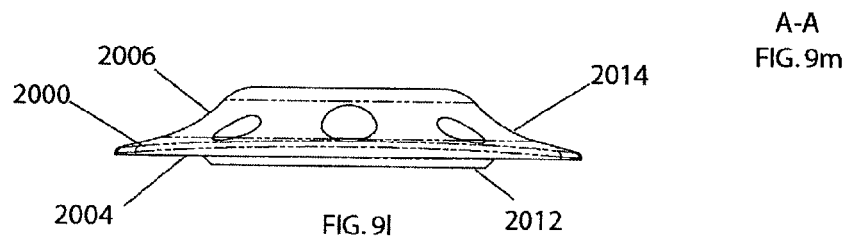
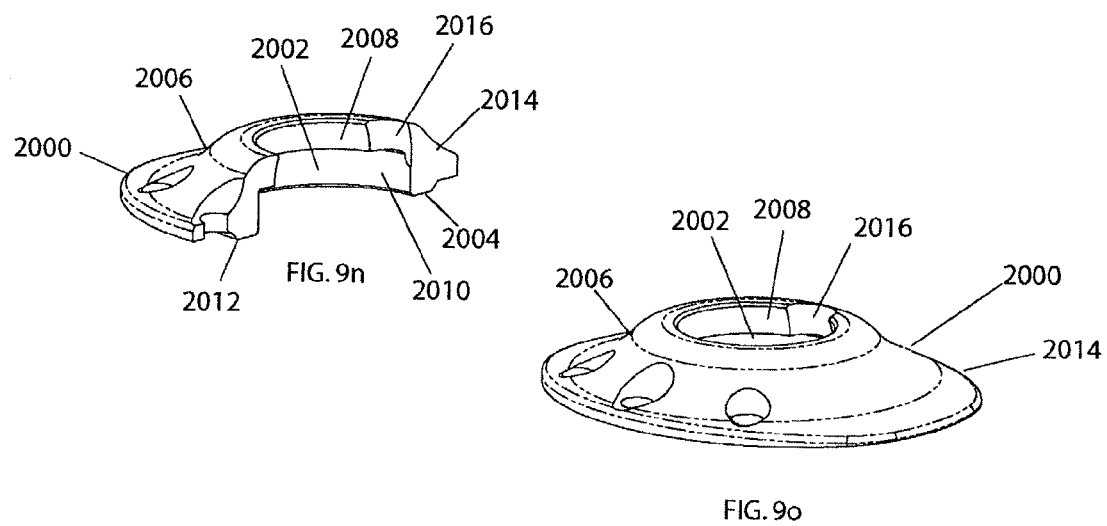

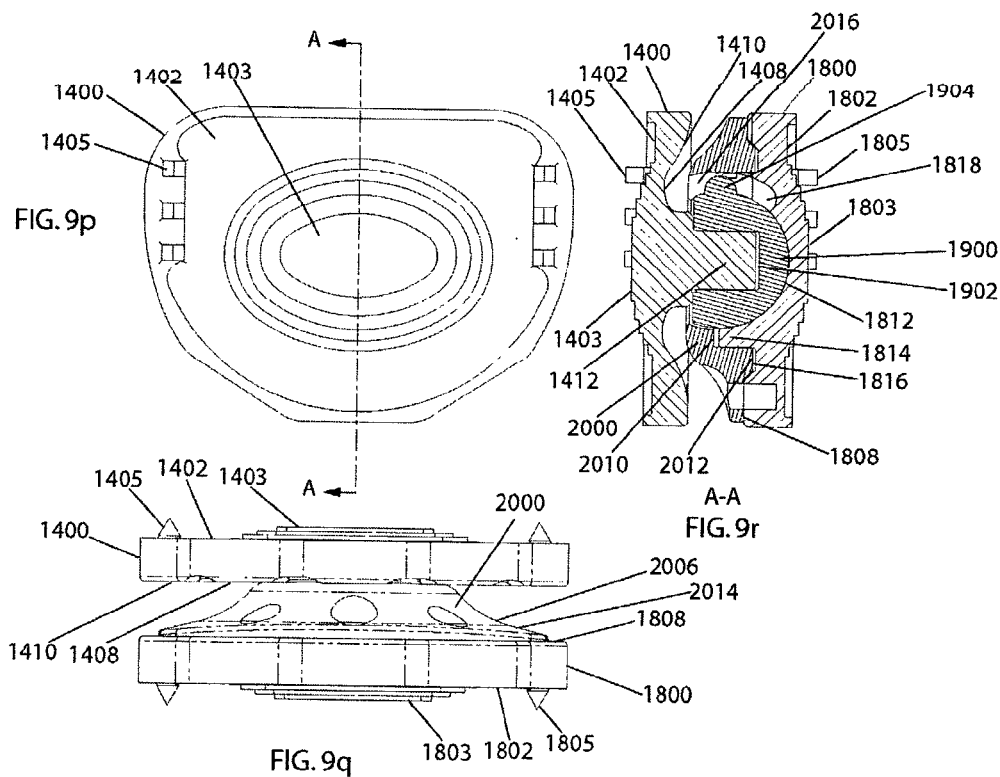
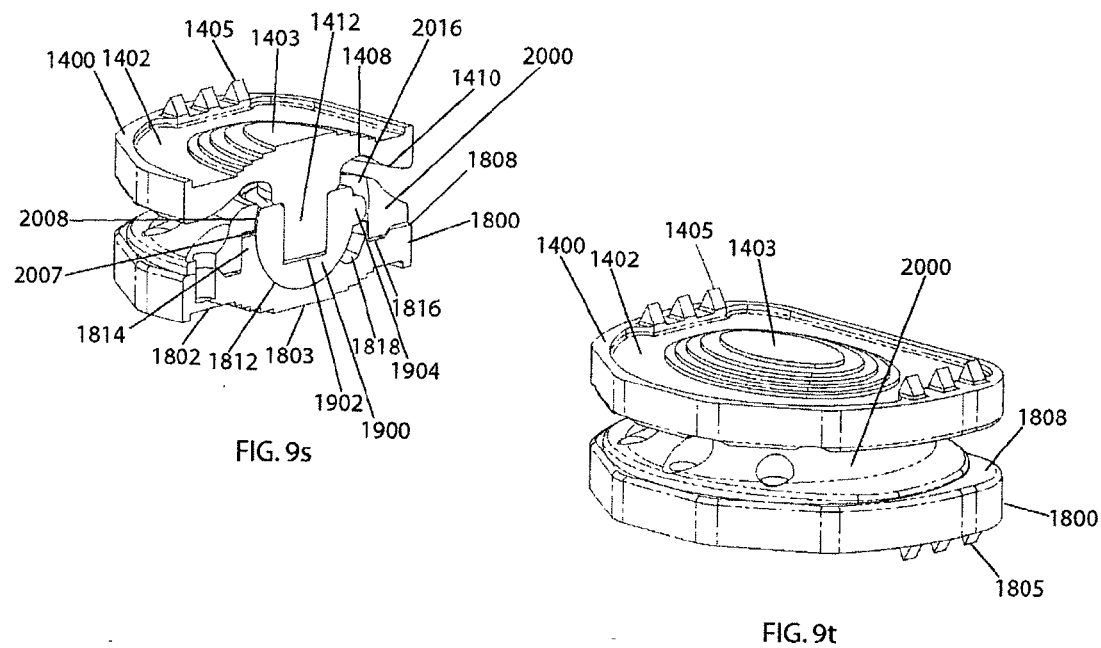

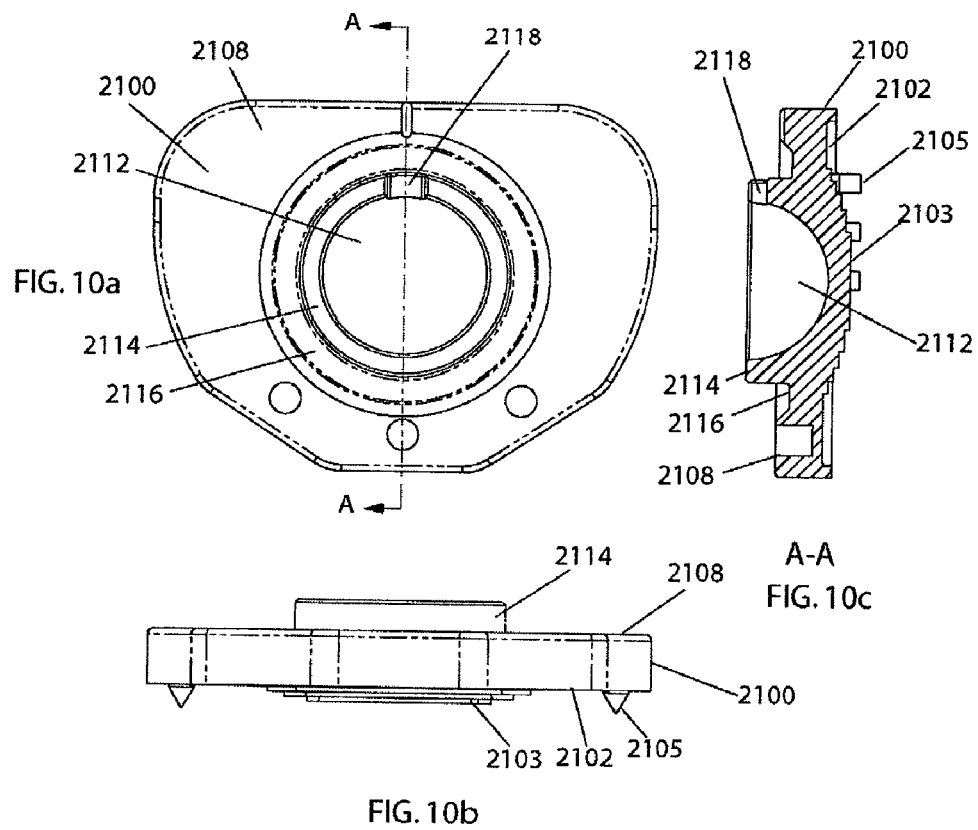
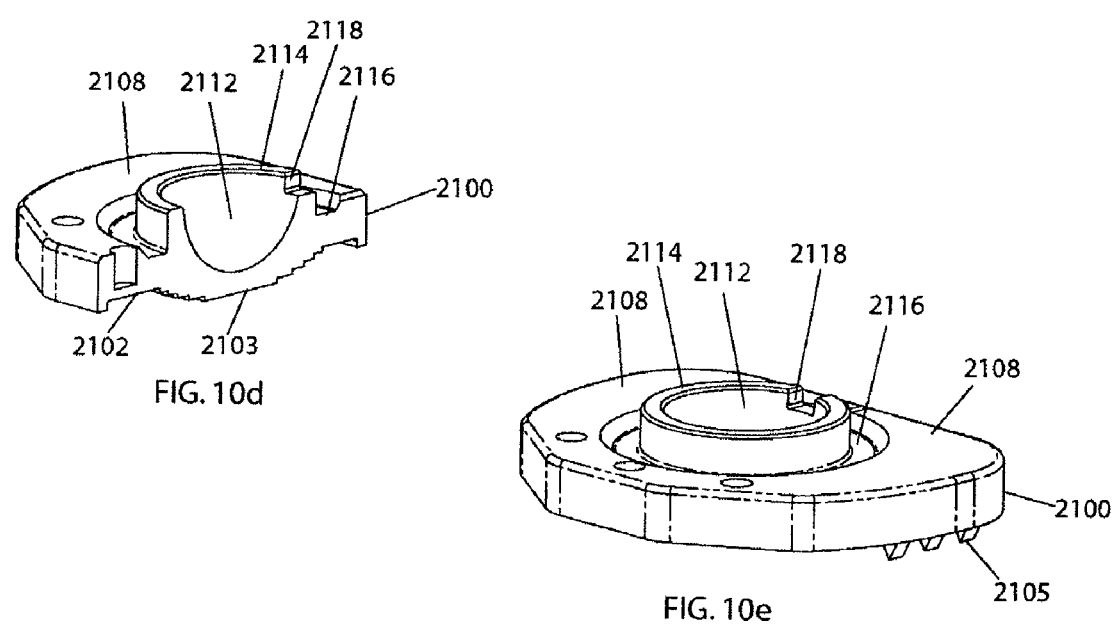

A-A

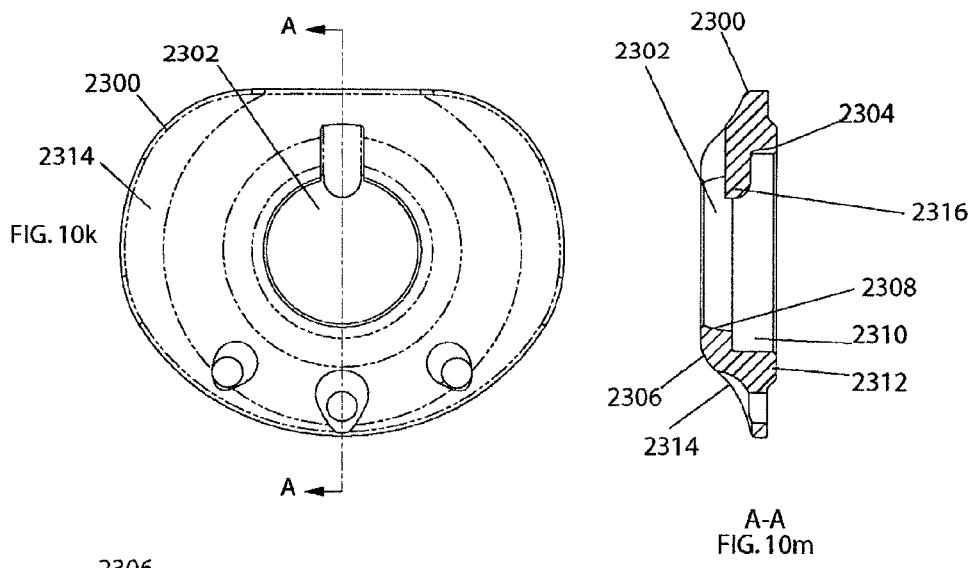
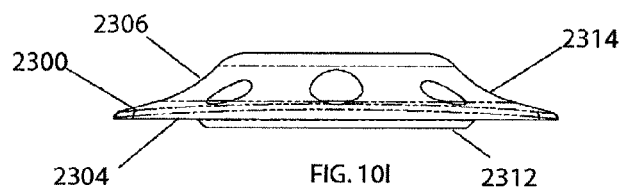
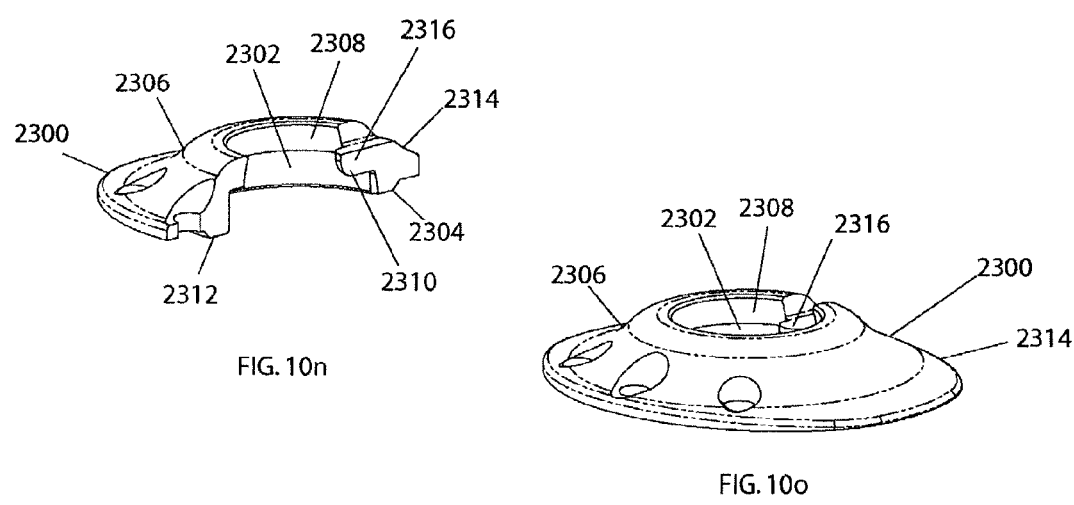

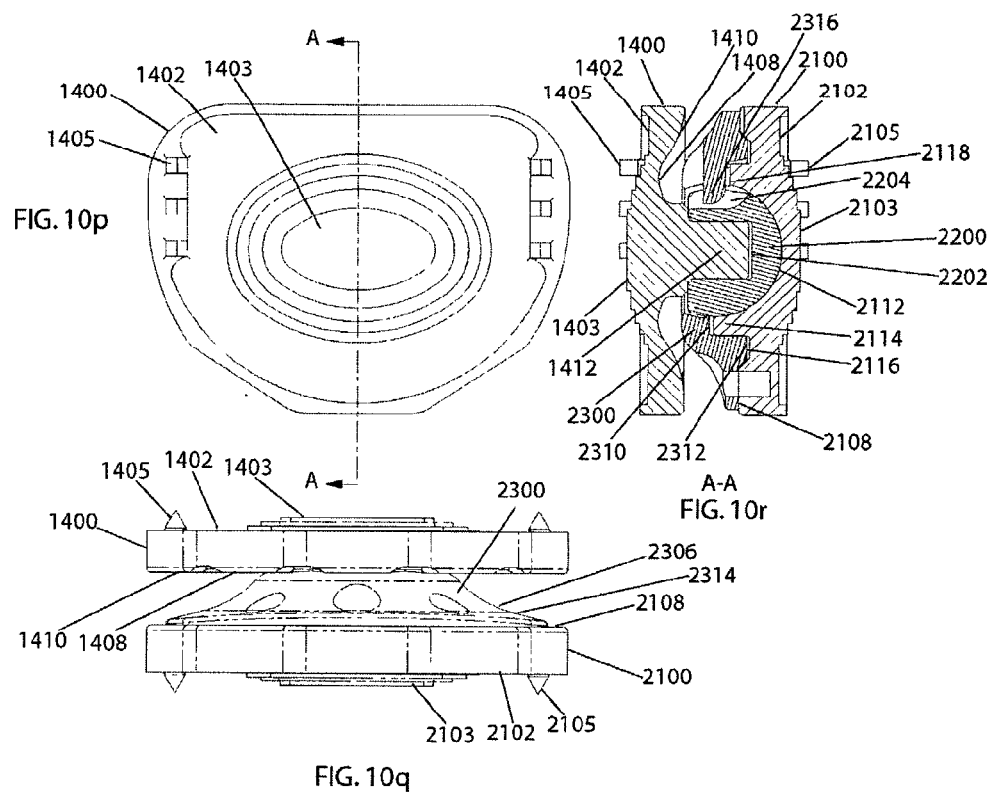
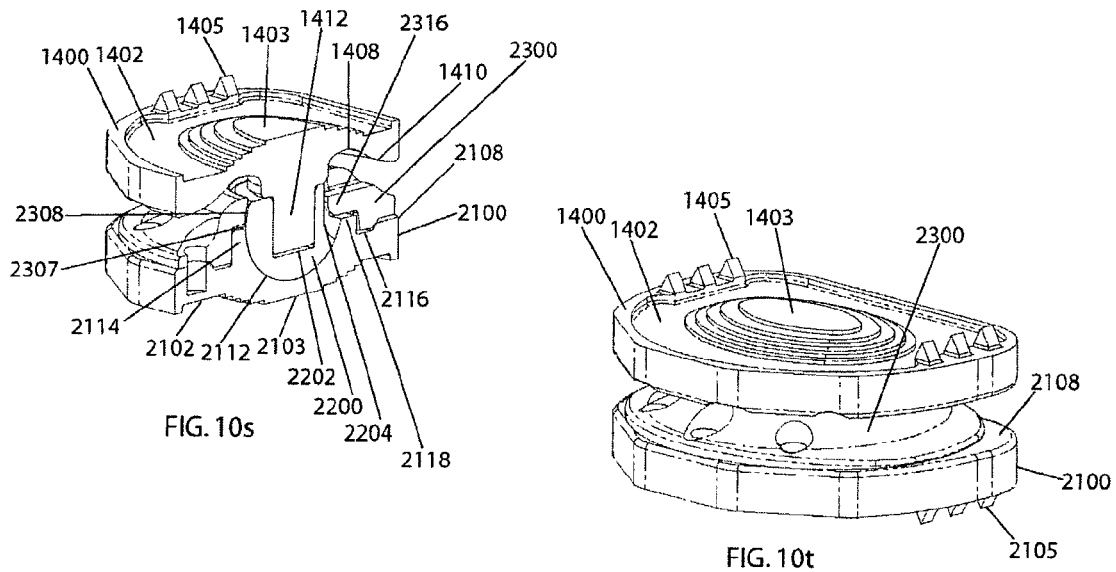

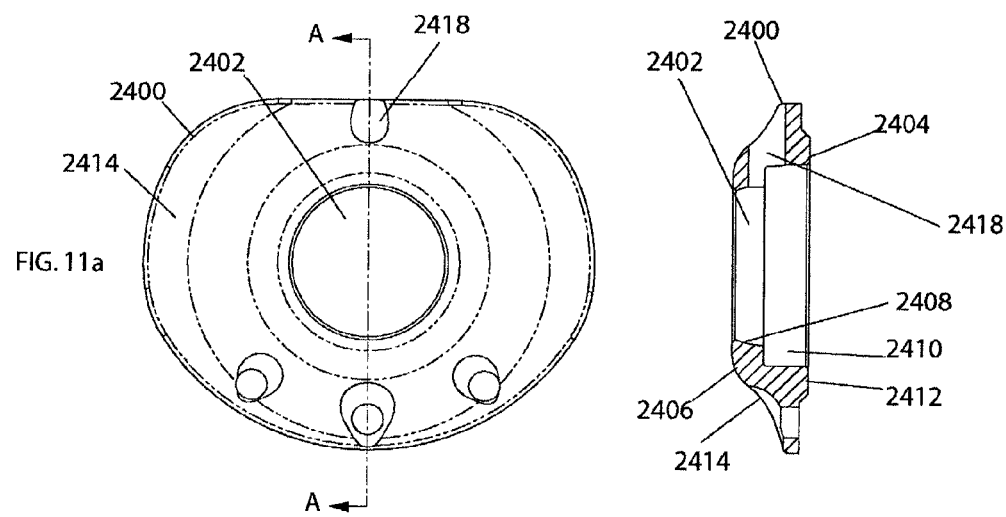
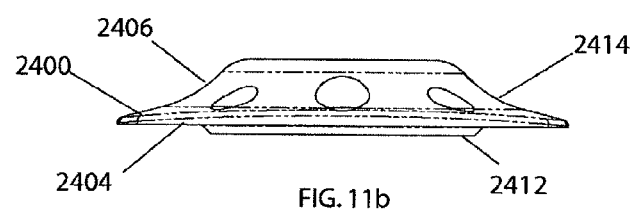
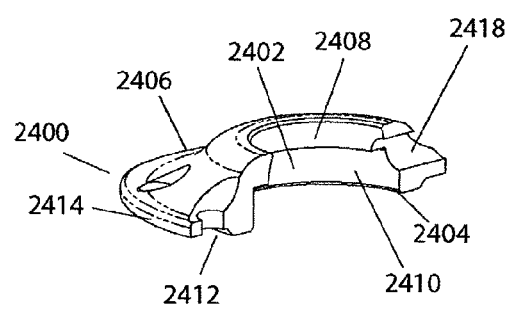
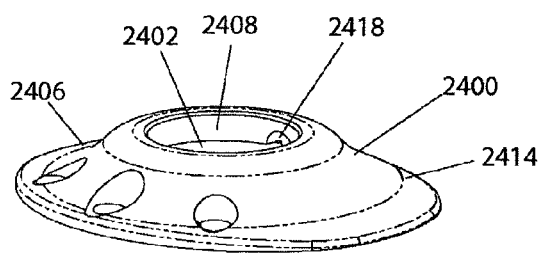
FIG. 11a
FIG. 11b
FIG. 11c A-A
FIG. 11d
FIG. 11e

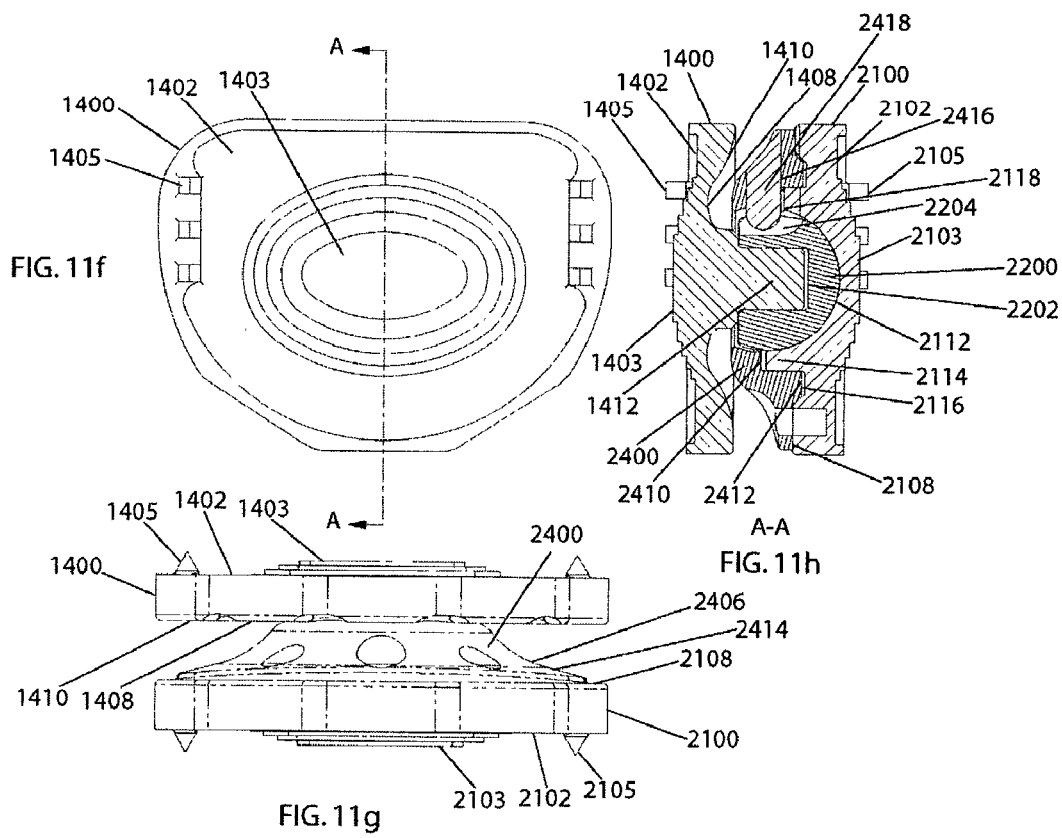
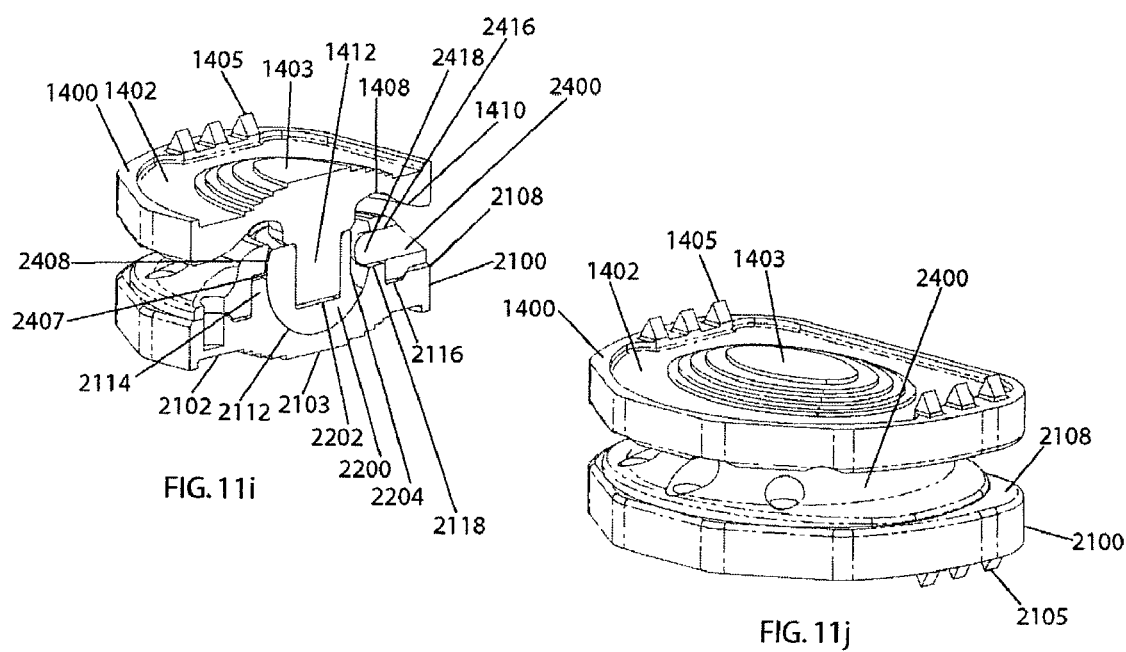

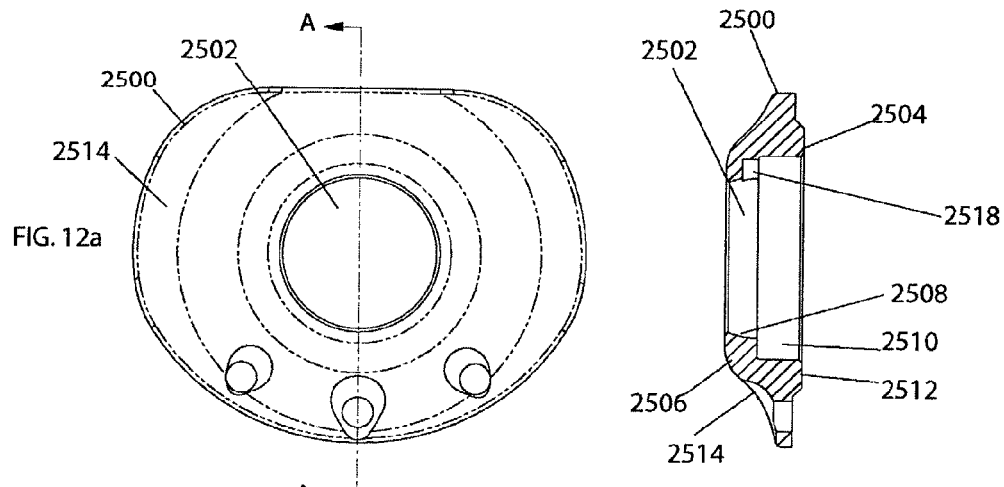
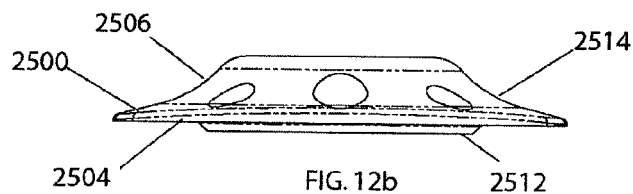
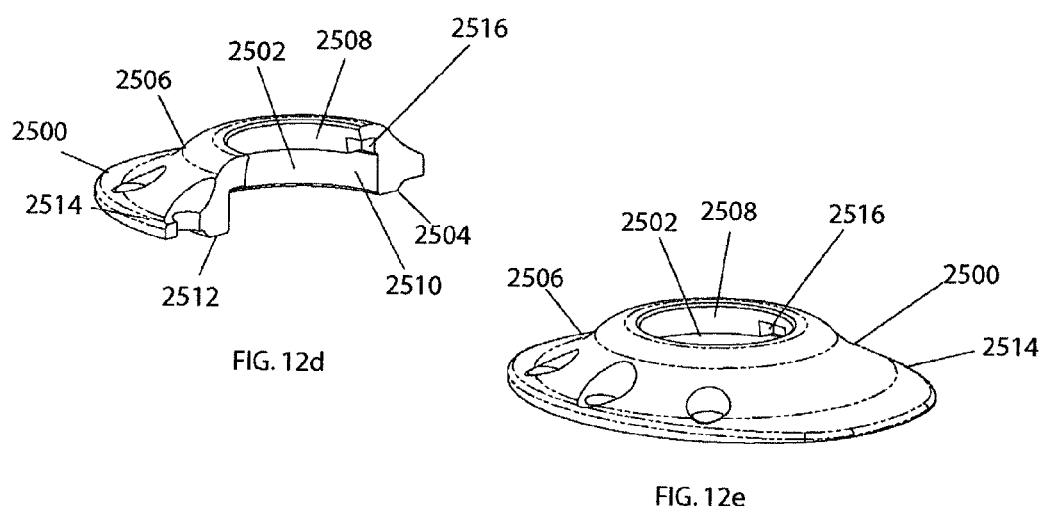

A-A

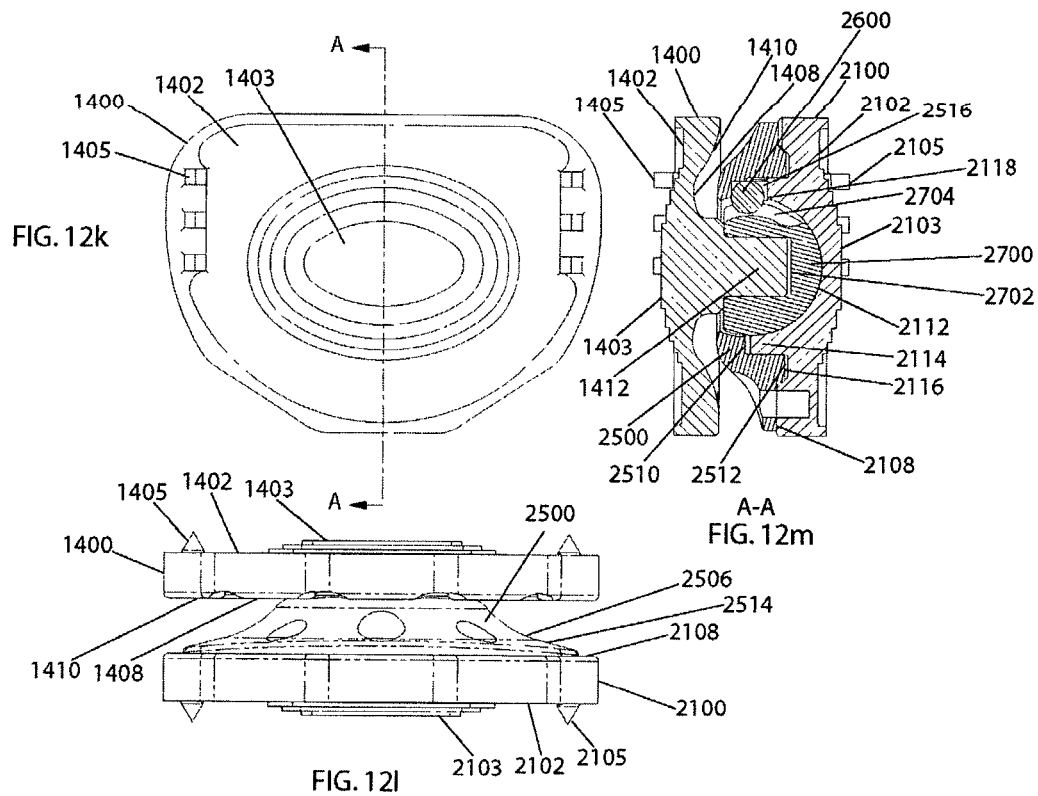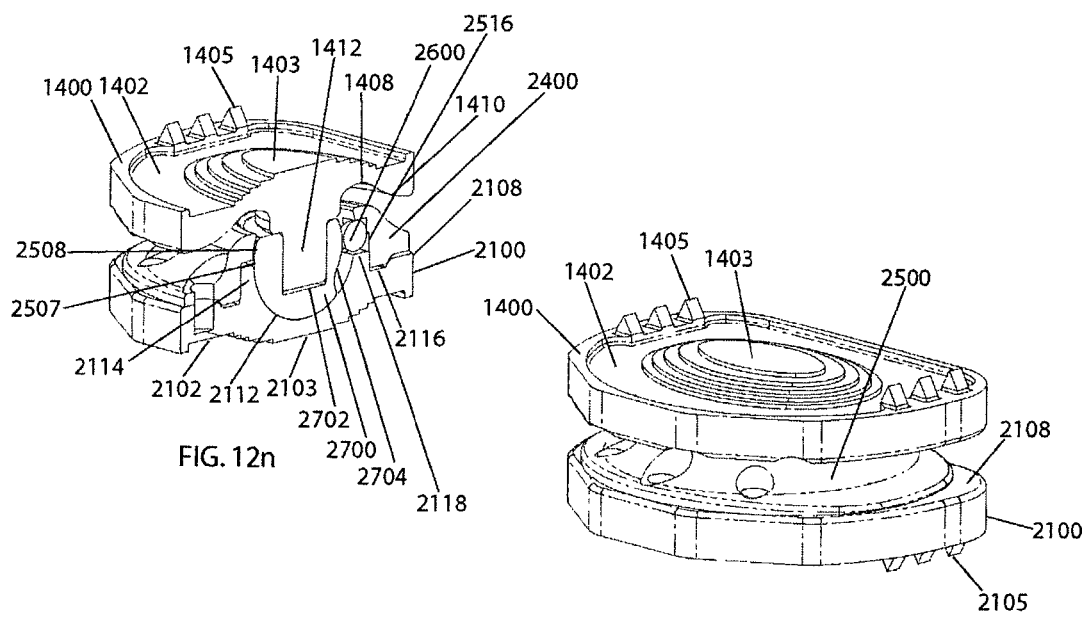

ARTIFICIAL INTERVERTEBRAL DISC HAVING A CAPTURED BALL AND SOCKET JOINT WITH A SOLID BALL AND RETAINING CAP

CROSS-REFERENCE TO RELATED APPLICATIONS

The present application is a continuation application of U.S. patent application Ser. No. 10/256,160 (filed Sep. 26, 2002) entitled "Artificial Intervertebral Disc Having Limited Rotation Using a Captured Ball and Socket Joint With a Solid Ball and Compression Locking Post", which is a continuation-in-part application of U.S. patent application Ser. No. 10/175,417 (filed Jun. 19, 2002) entitled "Artificial Intervertebral Disc Utilizing a Ball Joint Coupling", which is a continuation-in-part application of U.S. patent application Ser. No. 10/151,280 (filed May 20, 2002) entitled "Tension Bearing Artificial Disc Providing a Centroid of Motion Centrally Located Within an Intervertebral Space", which is a continuation-in-part application of both U.S. patent application Ser. No. 09/970,479 (filed Oct. 4, 2001) entitled "Intervertebral Spacer Device Utilizing a Spirally Slotted Belleville Washer Having Radially Extending Grooves" now U.S. Pat. No. 6,669,730 as well as U.S. patent application Ser. No. 10/140,153 (filed May 7, 2002) entitled "Artificial Intervertebral Disc Having a Flexible Wire Mesh Vertebral Body Contact Element", the former being a continuation-in-part application of U.S. patent application Ser. No. 09/968,046 (filed Oct. 1, 2001) entitled "Intervertebral Spacer Device Utilizing a Belleville Washer Having Radially Extending Grooves" now abandoned and the latter being a continuation-in-part application of both U.S. patent application Ser. No. 09/970,479 now U.S. Pat. No. 6,669,730 (detailed above) as well as U.S. patent application Ser. No. 10/128,619 (filed Apr. 23, 2002) entitled "Intervertebral Spacer Having a Flexible Wire Mesh Vertebral Body Contact Element" now U.S. Pat. No. 6,863,689, which is a continuation-in-part application of both U.S. patent application Ser. No. 09/906,119 (filed Jul. 16, 2001) and entitled "Trial Intervertebral Distraction Spacers" now U.S. Pat. No. 6,607,559 as well as U.S. patent application Ser. No. 09/982,148 (filed Oct. 18, 2001) and entitled "Intervertebral Spacer Device Having Arch Shaped Spring Elements" now U.S. Pat. No. 6,673,113. All of the above mentioned applications are hereby incorporated by reference herein in their respective entireties.

BACKGROUND OF THE INVENTION

This invention relates generally to a spinal implant assembly for implantation into the intervertebral space between adjacent vertebral bones to simultaneously provide stabilization and continued flexibility and proper anatomical motion, and more specifically to such a device that has a captured ball and socket joint with a solid ball and retaining cap.

The bones and connective tissue of an adult human spinal column consists of more than twenty discrete bones coupled sequentially to one another by a tri-joint complex that consists of an anterior disc and the two posterior facet joints, the anterior discs of adjacent bones being cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine, up to the base of the skull, includes the first seven vertebrae. The intermediate twelve bones are the thoracic vertebrae, and connect to the lower spine comprising the five lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column is highly complex in that it includes these more than twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. A variety of systems have been disclosed in the art that achieve immobilization and/or fusion of adjacent bones by implanting artificial assemblies in or on the spinal column. The region of the back that needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 13–14, in which a side perspective view of an intervertebral body cage and an anterior perspective view of a post implantation spinal column are shown, respectively, a more complete description of these devices of the prior art is herein provided. These cages 1 generally comprise tubular metal body 2 having an external surface threading 3. They are inserted transverse to the axis of the spine 4, into preformed cylindrical holes at the junction of adjacent vertebral bodies (in FIG. 14 the pair of cages 1 are inserted between the fifth lumbar vertebra (L5) and the top of the sacrum (S1)). Two cages 1 are generally inserted side by side with the external threading 4 tapping into the lower surface of the vertebral bone above (L5), and the upper surface of the vertebral bone (S1) below. The cages 1 include holes 5 through which the adjacent bones are to grow. Additional materials, for example autogenous bone graft materials, may be inserted into the hollow interior 6 of the cage 1 to incite or accelerate the growth of the bone into the cage. End caps (not shown) are often utilized to hold the bone graft material within the cage 1.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which mimics the biomechanical action of the natural disc cartilage, thereby permitting continued normal motion and stress distribution.

It is, therefore, an object of the invention to provide an intervertebral spacer that stabilizes the spine without promoting a bone fusion across the intervertebral space.

It is further an object of the invention to provide an implant device that stabilizes the spine while still permitting normal motion.

It is further an object of the invention to provide a device for implantation into the intervertebral space that does not promote the abnormal distribution of biomechanical stresses on the patient's spine.

It is further an object of the invention to provide an artificial disc that provides free rotation of the baseplates relative to one another.

It is further an object of the invention to provide an artificial disc that provides limited rotation of the baseplates relative to one another.

It is further an object of the invention to provide an artificial disc that supports compression loads.

It is further an object of the invention to provide an artificial disc that permits the baseplates to axially compress toward one another under a compressive load.

It is further an object of the invention to provide an artificial disc that permits the baseplates to axially compress toward one another under a compressive load and restore to their original uncompressed relative positions when the compressive load is relieved.

It is further an object of the invention to provide an artificial disc that supports tension loads.

It is further an object of the invention to provide an artificial disc that prevents lateral translation of the baseplates relative to one another.

It is further an object of the invention to provide an artificial disc that provides a centroid of motion centrally located within the intervertebral space.

It is further an object of the invention to provide an artificial disc baseplate attachment device (for attaching the baseplates of the artificial disc to the vertebral bones between which the disc is implanted) with superior gripping and holding strength upon initial implantation and thereafter.

It is further an object of the invention to provide an artificial disc baseplate attachment device that deflects during insertion of the artificial disc between vertebral bodies.

It is further an object of the invention to provide an artificial disc baseplate attachment device that conforms to the concave surface of a vertebral body.

It is further an object of the invention to provide an artificial disc baseplate attachment device that does not restrict the angle at which the artificial disc can be implanted.

It is further an object of the invention to provide an implant attachment device (for attaching the implant to bone) with superior gripping and holding strength upon initial implantation and thereafter.

It is further an object of the invention to provide an implant attachment device that is deflectable.

It is further an object of the invention to provide an implant attachment device that conforms to a concave bone surface.

Other objects of the invention not explicitly stated will be set forth and will be more clearly understood in conjunction with the descriptions of the preferred embodiments disclosed hereafter.

SUMMARY OF THE INVENTION

The preceding objects are achieved by the invention, which is an artificial intervertebral disc or intervertebral spacer device comprising a pair of support members (e.g., spaced apart baseplates), each with an outwardly facing surface. Because the artificial disc is to be positioned between the facing endplates of adjacent vertebral bodies, the baseplates are arranged in a substantially parallel planar alignment (or slightly offset relative to one another in accordance with proper lordotic angulation) with the outwardly facing surfaces facing away from one another. The baseplates are to mate with the vertebral bodies so as to not rotate relative thereto, but rather to permit the spinal segments to bend (and in some embodiments, axially compress) relative to one another in manners that mimic the natural motion of the spinal segment. This natural motion is permitted by the performance of a ball and socket joint (and in some embodiments, a spring member) disposed between the secured baseplates, and the securing of the baseplates to the vertebral bone is achieved through the use of a vertebral body contact element attached to the outwardly facing surface of each baseplate.

Preferable vertebral body contact elements include, but are not limited to, one or more of the following: a convex mesh, a convex solid dome, and one or more spikes. The convex mesh is preferably secured at its perimeter to the outwardly facing surface of the respective baseplate. This can be accomplished in any effective manner, however, laser welding and plasma coating burying are two preferred methods when the mesh is comprised of metal. While domed in its initial undeflected conformation, the mesh deflects as necessary during insertion of the artificial disc between vertebral bodies, and, once the artificial disc is seated between the vertebral bodies, the mesh deforms as necessary under anatomical loads to reshape itself to the concave surface of the vertebral endplate. Thus, the mesh is deformably reshapeable under anatomical loads such that it conformably deflects against the concave surface to securably engage the vertebral body endplate. Stated alternatively, because the mesh is convexly shaped and is secured at its perimeter to the baseplate, the mesh is biased away from the baseplate but moveable toward the plate (under a load overcoming the bias; such a load is present, for example, as an anatomical load in the intervertebral space) so that it will securably engage the vertebral body endplate when disposed in the intervertebral space. This affords the baseplate having the mesh substantially superior gripping and holding strength upon initial implantation, as compared with other artificial disc products. The convex mesh further provides an osteoconductive surface through which the bone may ultimately grow. The mesh preferably is comprised of titanium, but can also be formed from other metals and/or non-metals. Inasmuch as the mesh is domed, it does not restrict the angle at which the artificial disc can be implanted. It should be understood that while the flexible dome is described herein preferably as a wire mesh, other meshed or solid flexible elements can also be used, including flexible elements comprised of non-metals and/or other metals. Further, the flexibility, deflectability and/or deformability need not be provided by a flexible material, but can additionally or alternatively be provided mechanically or by other means.

It should be understood that the convex mesh attachment devices and methods described herein can be used not only with the artificial discs and artificial disc baseplates described or referred to herein, but also with other artificial discs and artificial disc baseplates, including, but not limited to, those currently known in the art. Therefore, the description of the mesh attachment devices and methods being used with the artificial discs and artificial disc baseplates described or referred to herein should not be construed as limiting the application and/or usefulness of the mesh attachment device.

To enhance the securing of the baseplates to the vertebral bones, each baseplate further comprises a porous area, which at least extends in a ring around the lateral rim of each outwardly facing surface. The porous area may be, for example, a sprayed deposition layer, or an adhesive applied beaded metal layer, or another suitable porous coating known in the art. The porous ring permits the long-term ingrowth of vertebral bone into the baseplate, thus permanently securing the prosthesis within the intervertebral space. The porous layer may extend beneath the domed mesh as well, but is more importantly applied to the lateral rim of the outwardly facing surface of the baseplate that seats directly against the vertebral body.

Some of the embodiments described herein uses two baseplates each having the above described convex mesh on its outwardly facing surface, while other embodiments use two baseplates each having a convex solid dome in combination with a plurality of spikes on the lateral rim of the outwardly facing surface of the baseplates. It should be understood, however, that the various attachments devices or methods described herein (as well as any other attachment devices or methods, such as, for example, keels) can be used individually or in combination in any permutation, without departing from the scope of the present invention.

The ball and socket joint disposed between the baseplates permits rotation and angulation of the two baseplates relative to one another about a centroid of motion centrally located between the baseplates. A wide variety of embodiments are contemplated, some in which the ball and socket joint permits free relative rotation of the baseplates, and others in which the ball and socket joint limits relative rotation of the baseplates to a certain range. Further in some embodiments, the ball and socket joint is used in conjunction with a spring member to additionally permit the two baseplates to axially compress relative to one another. Further in each of the embodiments, the assembly will not separate under tension loading, and prevents lateral translation of the baseplates during rotation and angulation.

More particularly, four embodiment families are described herein as examples of the present invention, with a preferred embodiment for the first embodiment family, a preferred embodiment for the second embodiment family, five preferred embodiments for the third embodiment family, and five embodiments for the fourth embodiment family, each being described in detail. However, it should be understood that the described embodiments and embodiment families are merely examples that illustrate aspects and features of the present invention, and that other embodiments and embodiment families are possible without departing from the scope of the invention.

Each of the embodiments in the four embodiment families discussed herein share the same basic elements, some of which retain identical functionality and configuration across the embodiments, and some of which gain or lose functionality and/or configuration across the embodiments to accommodate mechanical and/or manufacturing necessities. More specifically, each of the embodiments includes two baseplates joined to one another by a ball and socket joint that is established centrally between the baseplates. Each ball and socket joint is established by a socket being formed at the peak (or in the peak) of a convex structure extending from the second baseplate, and by a ball being secured to the first baseplate and being captured in the socket so that when the joint is placed under a tension or compression force, the ball remains rotatably and angulatably secure in the socket. However, the convex structure is configured differently in each of the embodiment families, and the manner in which the ball is captured in the socket is different in each of the embodiment families. Each of these two variations (the configuration of the convex structure and the manner of capturing the ball in the socket) among the embodiments families is summarized immediately below, and will be understood further in light of the additional descriptions of the embodiments herein. It should be noted that although each of the embodiment families uses a preferred shape for the convex structure (e.g., in the first and second embodiment families, the preferred shape is frusto-conical, and in the third and fourth embodiment families, the preferred shape is a shape having a curved taper), the convex structure in each of the embodiment families is not limited to a particular shape. For example, shapes including, but not limited to, frusto-conical, hemispherical or semispherical shapes, shapes having sloped tapers or curved tapers, or shapes having non-uniform, irregular or dimensionally varying tapers or contours, would also be suitable in any of the embodiment families.

With regard to the first embodiment family, the convex structure is configured as a flexible element and functions as a spring element that provides axial cushioning to the device. The convex structure has the socket of the ball and socket joint at its peak. In order to permit the flexible convex structure to flex under compressive loads applied to the device, it is separated from the second baseplate. In the preferred embodiment, the flexible convex structure is a belleville washer that has a frusto-conical shape. Other flexible convex structures are also contemplated as being suitable, such as, for example, convex structures that flex because of the resilience of the material from which they are made, because of the shape into which they are formed, and/or or because of the mechanical interaction between sub-elements of an assembly forming the convex structure. Although the convex structure is a separate element from the second baseplate in this embodiment family (because it must be allowed to flex), it is preferably maintained near the second baseplate so that the device does not separate in tension. Therefore, an extension of the second baseplate is provided (in the form of a shield element) to cover enough of the convex structure to so maintain it. Stated alternatively, the shield is a separate element from the second baseplate to ease manufacturing (during assembly, the flexible convex structure is first placed against the second baseplate, and then the shield is placed over the convex structure and secured to the second baseplate so that the convex structure is maintained between the second baseplate and the shield), but once the device is assembled, the second baseplate and the shield are effectively one element. That is, the second baseplate and shield can be considered to be a single integral housing within which the separate flexible convex structure flexes, because but for the sake of achieving desirable manufacturing efficiencies, the second baseplate and shield would be one piece.

Also with regard to the first embodiment family, the manner of capturing the ball in the socket is effected by the ball being selectively radially compressible. That is, the ball is radially compressible to fit into the socket and thereafter receives a deflection preventing element to prevent subsequent radial compression, so that the ball remains captured in the socket. A more detailed description of the preferred manner in which this is accomplished is described below. Because the socket is formed at the peak of the flexible convex structure discussed immediately above, the capturing of the ball in the socket in this manner allows the ball to remain securely held for rotation and angulation even though the socket moves upward and downward with the flexing of the convex structure. The second baseplate preferably includes an access hole that facilitates the capture of the ball in the socket; in this embodiment family, it facilitates the capture by accommodating placement of the deflection preventing element, so that the same can be applied to the ball after the ball is fitted into the socket. Accordingly, the ball is maintained in the socket.

With regard to the second embodiment family, the convex structure is configured as a non-flexible element that is integral with the second baseplate, and has the socket of the ball and socket joint at its peak. More clearly stated, the devices of this second embodiment family do not feature a flexible convex structure, and therefore (and also because of the manner in which the ball is captured in this second embodiment family, discussed immediately below) there is no need for the convex structure to be a separate element from the second baseplate. (By contrast, in the first embodiment family, as discussed above, because the convex structure is flexible, it is a separate element than the second baseplate so that it is able to flex.) In the preferred embodiment, the convex structure has a frusto-conical shape. The manner of capturing the ball in the socket in this second embodiment family is identical to that of the first embodiment family.

With regard to the third embodiment family, the convex structure is configured as a non-flexible element that is integral with the second baseplate, and has the socket of the ball and socket joint in its peak, similar to the configuration of the convex structure in the second embodiment family. In the preferred embodiment, the convex structure is shaped to have a curved taper. The manner of capturing the ball in the socket of this third embodiment family is effected through the use of a solid ball. In order to permit the seating of the ball into the socket, the second baseplate has an access hole that facilitates the capture of the ball in the socket; in this embodiment family, the access hole facilitates the capture in that it has a diameter that accommodates the diameter of the ball, and leads to the interior of the peak, which interior is formed as a concavity having an opening diameter that accommodates the diameter of the ball. (Preferably, the concavity has a curvature closely accommodating the contour of the ball, and the concavity is either hemispherical or less-than-hemispherical so that the ball can easily be placed into it.) Further, in order to maintain the ball in the socket, an extension of the second baseplate (in the form of a cap element) is provided for sealing the access hole in the second baseplate (or reducing the opening diameter of the access hole to a size that does not accommodate the diameter of the ball). The cap has an interior face that preferably has a concavity (that has a curvature that closely accommodates the contour of the ball) to complete the socket. The peak of the convex structure also has a bore that accommodates a post to which the ball and the first baseplate are attached (one to each end of the post), but does not accommodate the ball for passage through the bore. Accordingly, the ball is maintained in the socket.

With regard to the fourth embodiment family, the convex structure is configured as a non-flexible element that is a separate element from, but attached to, the second baseplate, and has the socket of the ball and socket joint in its peak. In the preferred embodiment, the convex structure is shaped to have a curved taper, similar to the configuration of the convex structure in the third embodiment family. The convex structure in this fourth embodiment family is separate from the second baseplate during assembly of the device, for reasons related to the manner in which the ball is captured in the socket, but is attached to the second baseplate by the time assembly is complete. The manner of capturing the ball in the socket of this fourth embodiment family is effected through the use of a solid ball. The ball is first seated against the central portion of the second baseplate (which central portion preferably has a concavity that has a curvature that closely accommodates the contour of the ball), and then the convex structure is placed over the ball to seat the ball in the socket formed in the interior of the peak of the convex structure (the interior is preferably formed as a concavity that is either hemispherical or less-than-hemispherical so that the ball can easily fit into it). After the convex structure is placed over the ball, the convex structure is attached to the second baseplate to secure the ball in the socket. As in the third embodiment family, the peak of the convex structure also has a bore that accommodates a post to which the ball and the first baseplate are attached (one to each end of the post), but does not accommodate the ball for passage through the bore. Accordingly, the ball is maintained in the socket.

It should be understood that each of the features of each of the embodiments described herein, including, but not limited to, formations and functions of convex structures, manners of capturing the ball in the socket, types of spring elements, and manners of limiting rotation of the baseplates relative to one another, can be included in other embodiments, individually or with one or more others of the features, in other permutations of the features, including permutations that are not specifically described herein, without departing from the scope of the present invention.

Each of the embodiment families will now be summarized in greater detail.

In the first embodiment family, the ball and socket joint includes a radially compressible ball (which, in some embodiments, is shaped as a semisphere), mounted to protrude from an inwardly facing surface of a first baseplate, and a curvate socket formed at a peak of a flexible convex structure that is flexibly maintained near a second baseplate, within which curvate socket the ball is capturable for free rotation and angulation therein. Because the convex structure is flexible, it functions as a force restoring element (e.g., a spring) that provides axial cushioning to the device, by deflecting under a compressive load and restoring when the load is relieved. The flexible convex structure is preferably a belleville washer that has a frusto-conical shape. In general, a belleville washer is one of the strongest configurations for a spring, and is highly suitable for use as a restoring force providing element in an artificial intervertebral disc which must endure considerable cyclical loading in an active human adult.

Belleville washers are washers that are generally bowed in the radial direction (e.g., have a hemispherical or semispherical shape) or sloped in the radial direction (e.g., have a frusto-conical shape). Bowed belleville washers have a radial convexity (i.e., the height of the washer is not linearly related to the radial distance, but may, for example, be parabolic in shape). In a sloped belleville washer, the height of the washer is linearly related to the radial distance. Of course, other shape variations of belleville washers are suitable (such as, but not limited to, belleville washers having non-uniform tapers or irregular overall shapes). The restoring force of a belleville washer is proportional to the elastic properties of the material. In addition, the magnitude of the compressive load support and the restoring force provided by the belleville washer may be modified by providing slots and/or grooves in the washer. The belleville washer utilized as the force restoring member in the illustrated embodiment is spirally slotted, with the slots initiating on the periphery of the washer and extending along arcs that are generally radially inwardly directed a distance toward the center of the bowed disc, and has radially extending grooves that decrease in width and depth from the outside edge of the washer toward the center of the washer. As a compressive load is applied to a belleville washer, the forces are directed into a hoop stress that tends to radially expand the washer. This hoop stress is counterbalanced by the material strength of the washer, and the strain of the material causes a deflection in the height of the washer. Stated equivalently, a belleville washer responds to a compressive load by deflecting compressively, but provides a restoring force that is proportional to the elastic modulus of the material in a hoop stressed condition. With slots and/or grooves formed in the washer, it expands and restores itself far more elastically than a solid washer.

In order to permit the flexible convex structure to flex under compressive loads applied to the device, it is a separate element from the second baseplate in the preferred embodiment. To provide room for the flexible convex structure to expand in unrestricted fashion when it is compressed, while generally maintaining the flexible convex structure within a central area near the second baseplate, the wide end of the flexible convex structure is housed in the second baseplate through the use of an extension of the second baseplate structure (in the form of a shield element that is secured to the second baseplate). More particularly, a circular recess is provided on an inwardly facing surface of the second baseplate, and the wide end of the flexible convex structure is seated into the recess. The extension of the second baseplate (e.g., a shield) is placed over the flexible convex structure to cover enough of the convex structure to prevent it from escaping the recess, and then is attached to the second baseplate. As stated above, the shield is a separate element from the second baseplate to ease manufacturing, but once the device is assembled, the second baseplate and the shield are effectively one element. That is, the second baseplate and shield can be considered to be a single integral housing within which the separate flexible convex structure flexes, because but for the sake of achieving desirable manufacturing efficiencies, the second baseplate and shield would be one piece.

More particularly with regard to the ball, the ball includes a series of slots that render it radially compressible and expandable in correspondence with a radial pressure. The ball further includes an axial bore that accepts a deflection preventing element (e.g., a rivet). Prior to the insertion of the rivet, the ball can deflect radially inward because the slots will narrow under a radial pressure. The insertion of the rivet eliminates the capacity for this deflection. Therefore, the ball, before receiving the rivet, can be compressed to pass into, and thereafter seat in, the curvate socket of the second baseplate. (The curvate socket has an opening diameter that accommodates passage therethrough of the ball in a radially compressed state (but not in an uncompressed state), and a larger inner diameter that accommodates the ball in the uncompressed state.) Once the ball has been seated in the curvate socket, the rivet can be inserted into the axial bore to ensure that the ball remains held in the curvate socket. The second baseplate preferably includes an access hole that accommodates placement of the deflection preventing element, so that the same can be applied to the ball after the ball is fitted into the socket.

The curvate socket defines a spherical contour that closely accommodates the ball for free rotation and angulation in its uncompressed state. Therefore, when seated in the curvate socket, the ball can rotate and angulate freely relative to the curvate socket through a range of angles, thus permitting the opposing baseplates to rotate and angulate freely relative to one another through a corresponding range of angles equivalent to the fraction of normal human spine rotation and angulation (to mimic normal disc rotation and angulation). The flexible convex structure serving as a force restoring device further provides spring-like performance with respect to axial compressive loads, as well as long cycle life to mimic the axial biomechanical performance of the normal human intervertebral disc. Because the ball is held within the curvate socket by a rivet in the axial bore preventing radial compression of the protuberance, the artificial disc can withstand tension loading of the baseplates—the assembly does not come apart under normally experienced tension loads. Thus, in combination with the securing of the baseplates to the adjacent vertebral bones via the mesh domes, the disc assembly has an integrity similar to the tension-bearing integrity of a healthy natural intervertebral disc. Also because the ball is laterally captured in the curvate socket, lateral translation of the baseplates relative to one another is prevented during rotation and angulation, similar to the performance of healthy natural intervertebral disc. Because the baseplates are made angulatable relative to one another by the ball being rotatably and angulatably coupled in the curvate socket, the disc assembly provides a centroid of motion within the sphere defined by the ball. Accordingly, the centroid of motion of the disc assembly remains centrally located between the vertebral bodies, similar to the centroid of motion in a healthy natural intervertebral disc.

In the second embodiment family, the ball and socket joint includes a radially compressible ball (or in some embodiments, a semisphere) mounted to protrude from an inwardly facing surface of a first baseplate, and a curvate socket formed at a peak of a non-flexible convex structure that is integral with a second baseplate, within which curvate socket the ball is capturable for free rotation and angulation therein. Because the convex structure is not flexible, it does not serve as a force restoring element (e.g., a spring). In the preferred embodiment, the convex structure has a frusto-conical shape. The formation of the curvate socket, the configuration of the ball for use therewith, and the manner in which the ball is captured in the socket, are preferably identical to that of the first embodiment family. Accordingly, the embodiments of the second embodiment family enjoy the characteristics and performance features of the embodiments of the first embodiment family, except for the axial cushioning.

In the third embodiment family, the ball and socket joint includes a solid ball (which, in some embodiments, is shaped as a semisphere) mounted to protrude from an inwardly facing surface of a first baseplate, and a curvate socket formed in a peak of a non-flexible convex structure that is integral with a second baseplate, within which curvate socket the ball is capturable for free rotation and angulation therein. In the preferred embodiment, the convex structure is shaped to have a curved taper. With regard to the mounting of the ball, the mounting includes a central post. A tail end of the post is (as a final step in the preferred assembly process) secured within a bore through the first baseplate, from the inwardly facing surface of the first baseplate to its outwardly facing surface. The ball is mounted at a head end of the post. The curvate socket defines a spherical contour, and is formed by opposing curvate pockets, one formed on a central portion of an outwardly facing surface of the convex structure and one formed on an inwardly facing surface of an extension of the second baseplate (the extension being in the form of a cap element) that secures to the outwardly facing surface of the second baseplate. When the cap is secured to the outwardly facing surface of the second baseplate, the opposing curvate pockets together form the curvate socket within which the ball freely rotates and angulates. Each curvate pocket is semispherically (preferably hemispherically) contoured to closely accommodate the spherical contour defined by the ball, so that the ball can freely rotate in the socket about the longitudinal axis of the post, and can freely angulate in the socket about a centroid of motion located at the center of the sphere defined by the ball.

In order to enable the seating of the ball into the curvate socket, the access hole in the second baseplate leading to the outwardly facing surface of the convex structure has a diameter that accommodates the diameter of the ball, and the curvate pocket on the outwardly facing surface of the convex structure has an opening diameter that accommodates the ball for seating in the pocket. Thus, the ball can be placed through the access hole and into the curvate pocket. Thereafter, the cap is applied to seal the access hole in the second baseplate (or reduce the diameter of the access hole to a size that does not accommodate the diameter of the ball). With regard to the attachment of the post to the first baseplate, the peak of the convex structure has a central bore that accommodates the diameter of the post, but not the diameter of the ball. Therefore, as the ball is being placed into the curvate pocket on the outwardly facing surface of the convex structure, the post fits through the bore, but the ball does not. After the cap is secured, the tail end of the post that is protruding from the bore is secured to the inwardly facing surface of the first baseplate by the tail end of the post preferably compression locking into a central bore in the first baseplate.

In some embodiments of the third embodiment family, the cap element includes a spring member, preferably disposed on the curvate pocket or between the curvate pocket and the remaining structure of the cap element. The spring member can be attached to the curvate pocket and/or the remaining structure of the cap element, or the spring member can be a separate element that is captured or maintained at least in part between the curvate pocket and the remaining structure of the cap element (in which embodiment the cap element may include multiple pieces). While not limited to any particular structure, assembly, or material, a spring member providing shock absorption preferably includes an elastomeric material, such as, for example, polyurethane or silicon, and a spring member providing shock dampening preferably includes a plastic material, such as, for example, polyethylene. It should be understood that metal springs may alternatively or additionally be used. Accordingly, in such embodiments, part or all of a compressive load applied to the baseplates will be borne by the spring member, which will dampen the load and/or absorb the load and preferably help return the baseplates to their original uncompressed relative positions.

Accordingly, the baseplates are rotatable relative to one another because the ball rotates freely within the socket, and angulatable relative to one another because the ball angulates freely within the socket. (In the embodiments further having the spring member, the baseplates are also axially compressible relative to one another.) Because the ball is held within the socket by the securing of the tail end of the post to the first baseplate and the securing of the cap to the second baseplate, the artificial disc can withstand tension loading of the baseplates—the assembly does not come apart under normally experienced tension loads. Thus, in combination with the securing of the baseplates to the adjacent vertebral bones, the disc assembly has an integrity similar to the tension-bearing integrity of a healthy natural intervertebral disc. Also because the ball is laterally captured in the socket, lateral translation of the baseplates relative to one another is prevented during rotation and angulation, similar to the performance of healthy natural intervertebral disc. Because the baseplates are made angulatable relative to one another by the ball being rotatably and angulatably coupled in the socket, the disc assembly provides a centroid of motion within the ball. Accordingly, the centroid of motion of the disc assembly remains centrally located between the vertebral bodies, similar to the centroid of motion in a healthy natural intervertebral disc.

Some embodiments in the third embodiment family limit the rotation (but preferably not the angulation) of the ball in the socket. Each embodiment accomplishes this in a different manner, but each embodiment utilizes interference between a protrusion and a recess to limit the rotation. In some embodiments, the protrusion is preferably hemispherical, and the recess preferably has a semicylindrical contour within which the protrusion fits. In other embodiments, the protrusion is preferably hemispherical, and the recess preferably has a curvate contour that is not semicylindrical. (It should be understood that the described formations of the recess and the protrusion are merely preferred, and that alternate formations, curvate or otherwise, for each are contemplated by the present invention; a particular shape or location of recess or a particular shape or location of protrusion is not required; any shape can be used so long as the recess and protrusion interact as desired.) The boundaries of the recess define the limits of rotation of the ball within the socket, by allowing movement of the protrusion relative to the recess as the ball rotates through a certain range in the socket, but providing interference with the protrusion to prevent rotation of the ball beyond that range in the socket. At the same time, the boundaries of the recess preferably do not limit the angulation of the ball within the socket, at least until the perimeter regions of the inwardly facing surfaces meet.

More particularly with respect to the manner in which these embodiments limit rotation, in some embodiments the ball has a protrusion that interferes with a recess adjacent the socket, the recess being formed by a curvate recess adjacent the curvate pocket on the central portion of the outwardly facing surface of the convex structure and a curvate recess adjacent the curvate pocket on the cap. In other embodiments, the housing (e.g., the second baseplate/convex structure and/or the cap) has a protrusion (e.g., a hemispherical protrusion or a hemispherical head of a pin secured in a pin hole in the housing) that interferes with a recess on the ball. In still other embodiments, each of the housing (e.g., the second baseplate/convex structure and/or the cap) and the ball has a recess, and a ball bearing fits within the recesses, so that the ball bearing functions as a protrusion that interferes with one or both of the recesses.

Therefore, when assembled, these embodiments of the third embodiment family enable angulation and limited rotation of the baseplates relative to one another about a centroid of motion that remains centrally located between the baseplates (at the center of the sphere defined by the ball), similar to the centroid of motion in a healthy natural intervertebral disc that is limited in its rotation by surrounding body structures. A benefit of limiting the relative rotation of the baseplates is that relative rotation beyond a certain range in a healthy natural disc is neither needed nor desired, because, for example, excess strain can be placed on the facet joints or ligaments thereby. As described with the rotationally free embodiments of the second embodiment family, the construction also prevents translation and separation of the baseplates relative to one another during rotation and angulation.

In the fourth embodiment family, the ball and socket joint includes a solid ball (which, in some embodiments, is shaped as a semisphere) mounted to protrude from an inwardly facing surface of a first baseplate, and a curvate socket formed in a peak of a non-flexible convex structure that is attached to an inwardly facing surface of a second baseplate, within which curvate socket the ball is capturable for free rotation and angulation therein. In the preferred embodiment, the convex structure is shaped to have a curved taper. With regard to the mounting of the ball, the mounting includes a central post that extends from the inwardly facing surface of the first baseplate. The ball is (as a final step in the preferred assembly process) mounted at a head end of the post, by the head end preferably compression locking into a central bore in the ball. The curvate socket defines a spherical contour, and is formed by opposing curvate pockets, one formed on an inwardly facing surface of the second baseplate, and one formed as a curvate tapered lip of a central bore that passes through a central portion of the convex structure from the convex structure's outwardly facing surface (having the curvate tapered lip) to its inwardly facing surface. When the convex structure is secured to the inwardly facing surface of the second baseplate, the opposing curvate pockets together form the curvate socket within which the ball freely rotates and angulates. Each curvate pocket is semispherically (preferably hemispherically) contoured to closely accommodate the spherical contour defined by the ball, so that the ball can freely rotate in each pocket about the longitudinal axis of the post, and can freely angulate in each pocket about a centroid of motion located at the center of the sphere defined by the ball.

In order to enable the seating of the ball into the curvate socket, the curvate pocket on the inwardly facing surface of the second baseplate has an opening diameter that accommodates the ball for seating in the pocket. Thus, the ball can be placed into the curvate pocket before the convex structure is attached to the second baseplate. Thereafter, the convex structure is attached to the inwardly facing surface of the second baseplate with the convex structure's curvate pocket (the curvate tapered lip of the convex structure's central bore) fitting against the ball to complete the ball and socket joint. With regard to completing the assembly, the central bore of the convex structure has a diameter that accommodates the diameter of the post, but not the diameter of the ball. Therefore, after the ball is secured in the curvate socket, the post fits through the bore so that the head end of the post can be compression locked to the ball, but the ball is prevented from escaping the socket through the central bore of the convex structure.

In some embodiments of the fourth embodiment family, the second baseplate includes a spring member, preferably disposed on the curvate pocket or between the curvate pocket and the remaining structure of the second baseplate. The spring member can be attached to the curvate pocket and/or the remaining structure of the second baseplate, or the spring member can be a separate element that is captured or maintained at least in part between the curvate pocket and the remaining structure of the second baseplate (in which embodiment the second baseplate may include multiple pieces). While not limited to any particular structure, assembly, or material, a spring member providing shock absorption preferably includes an elastomeric material, such as, for example, polyurethane or silicon, and a spring member providing shock dampening preferably includes a plastic material, such as, for example, polyethylene. It should be understood that metal springs may alternatively or additionally be used. Accordingly, in such embodiments, part or all of a compressive load applied to the baseplates will be borne by the spring member, which will dampen the load and/or absorb the load and preferably help return the baseplates to their original uncompressed relative positions.

Accordingly, the baseplates are rotatable relative to one another because the ball rotates freely within the socket, and angulatable relative to one another because the ball angulates freely within the socket. (In the embodiments further having the spring member, the baseplates are also axially compressible relative to one another.) Because the ball is held within the socket by the securing of the central post of the first baseplate to the ball and the securing of the convex structure to the second baseplate, the artificial disc can withstand tension loading of the baseplates—the assembly does not come apart under normally experienced tension loads. Thus, in combination with the securing of the baseplates to the adjacent vertebral bones, the disc assembly has an integrity similar to the tension-bearing integrity of a healthy natural intervertebral disc. Also because the ball is laterally captured in the socket, lateral translation of the baseplates relative to one another is prevented during rotation and angulation, similar to the performance of healthy natural intervertebral disc. Because the baseplates are made angulatable relative to one another by the ball being rotatably and angulatably coupled in the socket, the disc assembly provides a centroid of motion within the sphere defined by the ball. Accordingly, the centroid of motion of the disc assembly remains centrally located between the vertebral bodies, similar to the centroid of motion in a healthy natural intervertebral disc.

Some embodiments in the fourth embodiment family limit the rotation (but preferably not the angulation) of the ball in the socket formed by the curvate taper of the convex structure and the hemispherical contour of the curvate pocket of the second baseplate. Each embodiment accomplishes this in a different manner, but each embodiment utilizes interference between a protrusion and a recess to limit the rotation, similar to the manner in which such interference is utilized in the third embodiment family. In some embodiments, the protrusion is preferably hemispherical, and the recess preferably has a semicylindrical contour within which the protrusion fits. In other embodiments, the protrusion is preferably hemispherical, and the recess preferably has a curvate contour that is not semicylindrical. (It should be understood that the described formations of the recess and the protrusion are merely preferred, and that alternate formations, curvate or otherwise, for each are contemplated by the present invention; a particular shape or location of recess or a particular shape or location of protrusion is not required; any shape can be used so long as the recess and protrusion interact as desired.) The boundaries of the recess define the limits of rotation of the ball within the socket, by allowing movement of the protrusion relative to the recess as the ball rotates through a certain range in the socket, but providing interference with the protrusion to prevent rotation of the ball beyond that range in the socket. At the same time, the boundaries of the recess preferably do not limit the angulation of the ball within the socket, at least until the perimeter regions of the inwardly facing surface of the convex structure and the inwardly facing surface of the first baseplate meet.

More particularly with respect to the manner in which these embodiments limit rotation, in some embodiments the ball has a protrusion that interferes with a recess adjacent the socket, the recess being formed by a curvate recess adjacent the curvate pocket on the second baseplate and a curvate recess adjacent the curvate taper on the convex structure. In other embodiments, the housing (e.g., the second baseplate and/or the convex structure) has a protrusion (e.g., a hemispherical protrusion or a hemispherical head of a pin secured in a pin hole in the housing) that interferes with a recess on the ball. In still other embodiments, each of the housing (e.g., the second baseplate and/or the convex structure) and the ball has a recess, and a ball bearing fits within the recesses, so that the ball bearing functions as a protrusion that interferes with one or both of the recesses.

Therefore, when assembled, these embodiments of the fourth embodiment family enable angulation and limited rotation of the baseplates relative to one another about a centroid of motion that remains centrally located between the baseplates (at the center of the sphere defined by the ball), similar to the centroid of motion in a healthy natural intervertebral disc that is limited in its rotation by surrounding body structures. A benefit of limiting the relative rotation of the baseplates is that relative rotation beyond a certain range in a healthy natural disc is neither needed nor desired, because, for example, excess strain can be placed on the facet joints or ligaments thereby. As described with the rotationally free embodiments of the third embodiment family, the construction also prevents translation and separation of the baseplates relative to one another during rotation and angulation.

BRIEF DESCRIPTION OF THE DRAWINGS

FIGS. 3f–j show top (FIG. 3f), side (FIG. 3g), side cutaway (FIG. 3h), perspective cutaway (FIG. 3i) and perspective (FIG. 3j) views of a first type of a second baseplate of the third embodiment family, the first type of second baseplate having a convex structure of the third embodiment family integrated therewith.

FIGS. 3k–o show top (FIG. 3k), side (FIG. 3l), side cutaway (FIG. 3m), perspective cutaway (FIG. 3n) and perspective (FIG. 3o) views of a first type of a ball of the third embodiment family.

FIGS. 3p–t show top (FIG. 3p), side (FIG. 3q), side cutaway (FIG. 3r), perspective cutaway (FIG. 3s) and perspective (FIG. 3t) views of a first type of a cap of the third embodiment family.

FIGS. 3u–y show top (FIG. 3u), side (FIG. 3v), side cutaway (FIG. 3w), perspective cutaway (FIG. 3x) and perspective (FIG. 3y) views of an assembled first preferred embodiment of the third embodiment family.

FIGS. 4a–e show top (FIG. 4a), side (FIG. 4b), side cutaway (FIG. 4c), perspective cutaway (FIG. 4d) and perspective (FIG. 4e) views of a second type of the second baseplate of the third embodiment family, the second type of the second baseplate having the convex structure integrated therewith and also having a curvate recess.

FIGS. 4f–j show top (FIG. 4f), side (FIG. 4g), side cutaway (FIG. 4h), perspective cutaway (FIG. 4i) and perspective (FIG. 4j) views of a second type of the ball of the third embodiment family, the second type of the ball having a protrusion.

FIGS. 4k–o show top (FIG. 4k), side (FIG. 4l), side cutaway (FIG. 4m), perspective cutaway (FIG. 4n) and perspective (FIG. 4o) views of a second type of a cap of the third embodiment family, the second type of cap having a curvate recess.

FIGS. 4p–t show top (FIG. 4p), side (FIG. 4q), side cutaway (FIG. 4r), perspective cutaway (FIG. 4s) and perspective (FIG. 4t) views of an assembled second preferred embodiment of the third embodiment family.

FIGS. 5a–e show top (FIG. 5a), side (FIG. 5b), side cutaway (FIG. 5c), perspective cutaway (FIG. 5d) and perspective (FIG. 5e) views of a third type of the second baseplate of the third embodiment family, the third type of the second baseplate having the convex structure integrated therewith and also having a protrusion.

FIGS. 5k–o show top (FIG. 5k), side (FIG. 5l), side cutaway (FIG. 5m), perspective cutaway (FIG. 5n) and perspective (FIG. 5o) views of an assembled third preferred embodiment of the third embodiment family.

FIGS. 6a–e show top (FIG. 6a), side (FIG. 6b), side cutaway (FIG. 6c), perspective cutaway (FIG. 6d) and perspective (FIG. 6e) views of a fourth type of the second baseplate of the third embodiment family, the fourth type of the second baseplate having the convex structure integrated therewith and also having a pin through hole for housing a pin.

FIGS. 6f–j show top (FIG. 6f), side (FIG. 6g), side cutaway (FIG. 6h), perspective cutaway (FIG. 6i) and perspective (FIG. 6*j*) views of an assembled fourth preferred embodiment of the third embodiment family.

FIGS. 7*a–e* show top (FIG. 7*a*), side (FIG. 7*b*), side cutaway (FIG. 7*c*), perspective cutaway (FIG. 7*d*) and perspective (FIG. 7*e*) views of a fifth type of the second baseplate of the third embodiment family, the fifth type of the second baseplate having the convex structure integrated therewith and also having a recess.

FIGS. 7*f–j* show top (FIG. 7*f*), side (FIG. 7*g*), side cutaway (FIG. 7*h*), perspective cutaway (FIG. 7*i*) and perspective (FIG. 7*j*) views of an assembled fifth preferred embodiment of the third embodiment family.

FIGS. 8*a–e* show top (FIG. 8*a*), side (FIG. 8*b*), side cutaway (FIG. 8*c*), perspective cutaway (FIG. 8*d*) and perspective (FIG. 8*e*) views of a first baseplate of a fourth embodiment family of the present invention.

FIGS. 8*f–j* show top (FIG. 8*f*), side (FIG. 8*g*), side cutaway (FIG. 8*h*), perspective cutaway (FIG. 8*i*) and perspective (FIG. 8*j*) views of a first type of second baseplate of the fourth embodiment family, the first type of the second baseplate having a central curvate pocket of the fourth embodiment family.

FIGS. 8*p–t* show top (FIG. 8*p*), side (FIG. 8*q*), side cutaway (FIG. 8*r*), perspective cutaway (FIG. 8*s*) and perspective (FIG. 8*t*) views of a first type of a convex structure of the fourth embodiment family.

FIGS. 8*u–y* show top (FIG. 8*u*), side (FIG. 8*v*), side cutaway (FIG. 8*w*), perspective cutaway (FIG. 8*x*) and perspective (FIG. 8*y*) views of an assembled first preferred embodiment of the fourth embodiment family.

FIGS. 9*a–e* show top (FIG. 9*a*), side (FIG. 9*b*), side cutaway (FIG. 9*c*), perspective cutaway (FIG. 9*d*) and perspective (FIG. 9*e*) views of a second type of second baseplate of the fourth embodiment family, the second type of the second baseplate having the central curvate pocket and also having a curvate recess.

FIGS. 9*k–o* show top (FIG. 9*k*), side (FIG. 9*l*), side cutaway (FIG. 9*m*), perspective cutaway (FIG. 9*n*) and perspective (FIG. 9*o*) views of a second type of the convex structure of the fourth embodiment family, the second type of the convex structure having a curvate recess.

FIGS. 9*p–t* show top (FIG. 9*p*), side (FIG. 9*q*), side cutaway (FIG. 9*r*), perspective cutaway (FIG. 9*s*) and perspective (FIG. 9*t*) views of an assembled second preferred embodiment of the fourth embodiment family.

FIGS. 10*a–e* show top (FIG. 10*a*), side (FIG. 10*b*), side cutaway (FIG. 10*c*), perspective cutaway (FIG. 10*d*) and perspective (FIG. 10*e*) views of a third type of second baseplate of the fourth embodiment family, the third type of the second baseplate having the central curvate pocket and also having a recess on a circumferential wall around the curvate pocket.

FIGS. 10*k–o* show top (FIG. 10*k*), side (FIG. 10*l*), side cutaway (FIG. 10*m*), perspective cutaway (FIG. 10*n*) and perspective (FIG. 10*o*) views of a third type of the convex structure of the fourth embodiment family, the third type of the convex structure having a protrusion.

FIGS. 10*p–t* show top (FIG. 10*p*), side (FIG. 10*q*), side cutaway (FIG. 10*r*), perspective cutaway (FIG. 10*s*) and perspective (FIG. 10*t*) views of an assembled third preferred embodiment of the fourth embodiment family.

FIGS. 11*a–e* show top (FIG. 11*a*), side (FIG. 11*b*), side cutaway (FIG. 11*c*), perspective cutaway (FIG. 11*d*) and perspective (FIG. 11*e*) views of a fourth type of the convex structure of the fourth embodiment family, the fourth type of the convex structure having a pin through hole for housing a pin.

FIGS. 11*f–j* show top (FIG. 11*f*), side (FIG. 11*g*), side cutaway (FIG. 11*h*), perspective cutaway (FIG. 11*i*) and perspective (FIG. 11*j*) views of an assembled fourth preferred embodiment of the fourth embodiment family.

FIGS. 12*a–e* show top (FIG. 12*a*), side (FIG. 12*b*), side cutaway (FIG. 12*c*), perspective cutaway (FIG. 12*d*) and perspective (FIG. 12*e*) views of a fifth type of the convex structure of the fourth embodiment family, the fifth type of the convex structure having a recess adjacent a curvate taper.

FIGS. 12*k–o* show top (FIG. 12*k*), side (FIG. 12*l*), side cutaway (FIG. 12*m*), perspective cutaway (FIG. 12*n*) and perspective (FIG. 12*o*) views of an assembled fifth preferred embodiment of the fourth embodiment family.

DETAILED DESCRIPTION OF THE PREFERRED EMBODIMENTS

While the invention will be described more fully hereinafter with reference to the accompanying drawings, in which particular embodiments and methods of implantation are shown, it is to be understood at the outset that persons skilled in the art may modify the invention herein described while achieving the functions and results of the invention. Accordingly, the descriptions that follow are to be understood as illustrative and exemplary of specific structures, aspects and features within the broad scope of the invention and not as limiting of such broad scope. Like numbers refer to similar features of like elements throughout.

A preferred embodiment of a first embodiment family of the present invention will now be described.

Figure 1A:
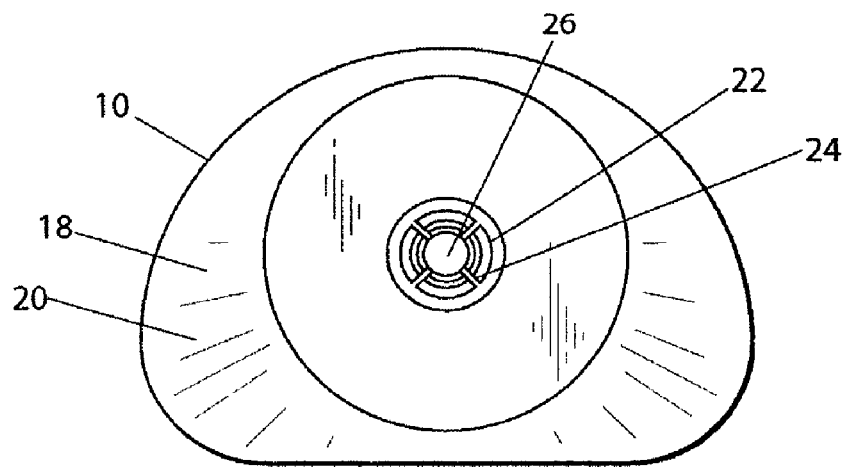
FIGS. 1a–c show top (FIG. 1a), side cutaway (FIG. 1b) and bottom (FIG. 1c) views of a first baseplate of a first embodiment family of the present invention, the first baseplate having an inwardly directed radially compressible ball.
Figure 1B:
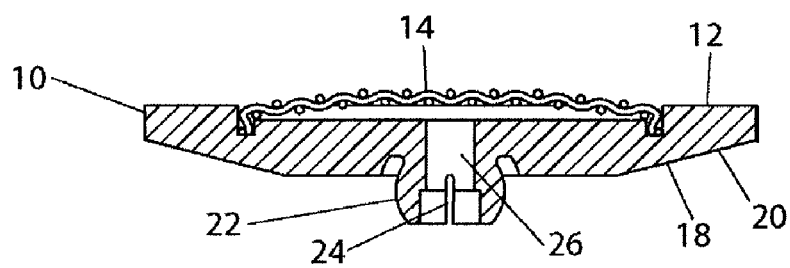
Figure 1C:
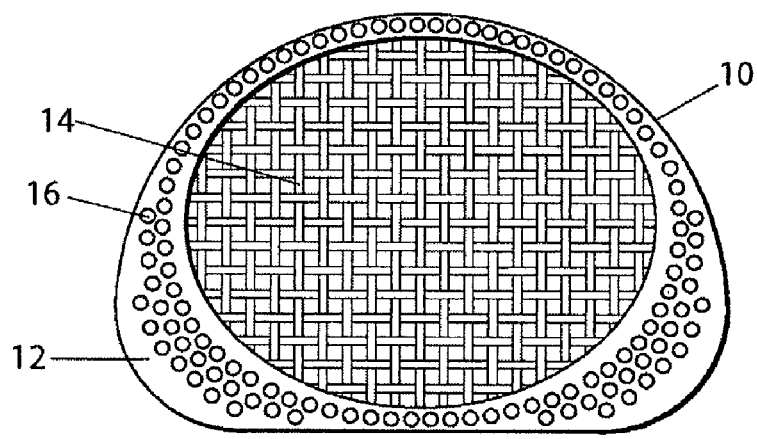
Figure 1D:
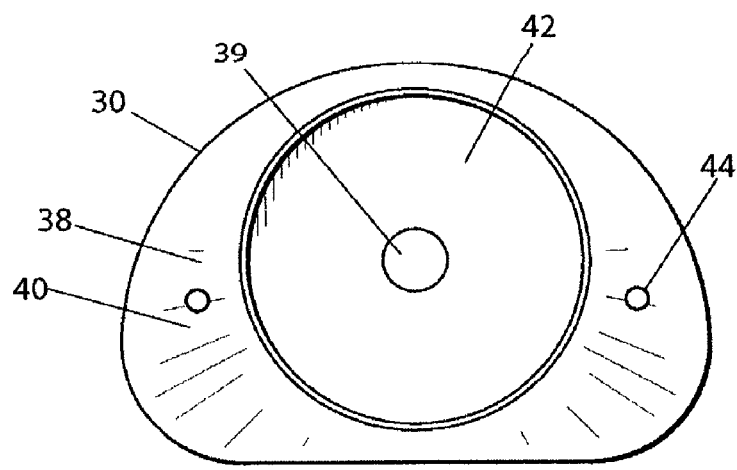
FIGS. 1d–f show top (FIG. 1d), side cutaway (FIG. 1e) and bottom (FIG. 1f) views of a second baseplate of the first embodiment family, the second baseplate having a circular recess within which seats a flexible convex structure.
Figure 1E:
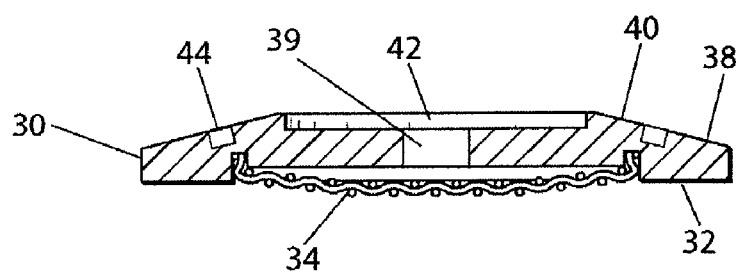
Figure 1F:
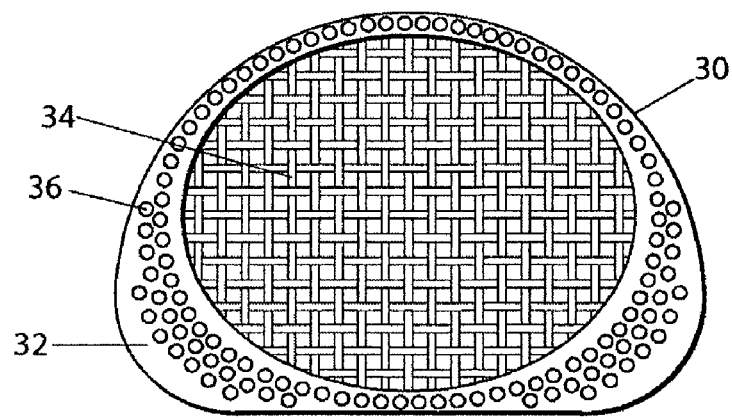

Referring to FIGS. 1*a–c*, a first baseplate 10 of a first embodiment family of the present invention is shown in top (FIG. 1*a*), side cutaway (FIG. 1*b*) and bottom (FIG. 1*c*) views. Also referring to FIGS. 1*d*, a second baseplate 30 of the first embodiment family is shown in top (FIG. 1*d*), side cutaway (FIG. 1*e*) and bottom (FIG. 1*f*) views.

More specifically, each baseplate 10,30 has an outwardly facing surface 12,32. Because the artificial disc of the invention is to be positioned between the facing surfaces of adjacent vertebral bodies, the two baseplates 10,30 used in the artificial disc are disposed such that the outwardly facing surfaces 12,32 face away from one another (as best seen in exploded view in FIG. 1g and in assembly view in FIG. 1h). The two baseplates 10,30 are to mate with the vertebral bodies so as to not rotate relative thereto, but rather to permit the spinal segments to bend relative to one another in manners that mimic the natural motion of the spinal segment. This motion is permitted by the performance of a ball and socket joint disposed between the secured baseplates 10,30. The mating of the baseplates 10,30 to the vertebral bodies and the construction of the ball and socket joint are described below.

More particularly, each baseplate 10,30 is a flat plate (preferably made of a metal such as, for example, cobalt-chromium or titanium) having an overall shape that conforms to the overall shape of the respective endplate of the vertebral body with which it is to mate. Further, each baseplate 10,30 comprises a vertebral body contact element (e.g., a convex mesh 14,34, preferably oval in shape) that is attached to the outwardly facing surface 12,32 of the baseplate 10,30 to provide a vertebral body contact surface. The mesh 14,34 is secured at its perimeter to the outwardly facing surface 12,32 of the baseplate 10,30. The mesh 14,34 is domed in its initial undeflected conformation, but deflects as necessary during insertion of the artificial disc between vertebral bodies, and, once the artificial disc is seated between the vertebral bodies, deforms as necessary under anatomical loads to reshape itself to the concave surface of the vertebral endplate. This affords the baseplate 10,30 having the mesh 14,34 substantially superior gripping and holding strength upon initial implantation as compared with other artificial disc products. The mesh 14,34 further provides an osteoconductive surface through which the bone may ultimately grow. The mesh 14,34 is preferably comprised of titanium, but can also be formed from other metals and/or non-metals without departing from the scope of the invention.

Each baseplate 10,30 further comprises at least a lateral ring 16,36 that is osteoconductive, which may be, for example, a sprayed deposition layer, or an adhesive applied beaded metal layer, or another suitable porous coating. This porous ring 16,36 permits the long-term ingrowth of vertebral bone into the baseplate 10,30, thus permanently securing the prosthesis within the intervertebral space. It shall be understood that this porous layer 16,36 may extend beneath the domed mesh 14,34 as well, but is more importantly applied to the lateral rim of the outwardly facing surface 12,32 of the baseplate 10,30 that seats directly against the vertebral body.

As summarized above, each of the embodiments in the four embodiment families discussed herein share the same basic elements, some of which retain identical functionality and configuration across the embodiments, and some of which gain or lose functionality and/or configuration across the embodiments to accommodate mechanical and/or manufacturing necessities. More specifically, each of the embodiments has the two baseplates joined to one another by a ball and socket joint that is established centrally between the baseplates. Each ball and socket joint is established by a socket being formed at the peak (or, in some embodiments, in the peak) of a convex structure extending from the second baseplate, and by a ball being secured to the first baseplate and being captured in the socket so that when the joint is placed under a tension or compression force, the ball remains rotatably and angulatably secure in the socket. However, the convex structure is configured differently in each of the embodiment families, and the manner in which the ball is captured in the socket is different in each of the embodiment families. Each of these two variations (the configuration of the convex structure and the manner of capturing the ball in the socket) among the embodiments families will be understood further in light of the detailed descriptions hereinbelow. It should be noted that although each of the embodiment families uses a preferred shape for the convex structure (e.g., in the first and second embodiment families, the preferred shape is frusto-conical, and in the third and fourth embodiment families, the preferred shape is a shape having a curved taper), the convex structure in each of the embodiment families is not limited to a particular shape. For example, shapes including, but not limited to, frusto-conical, hemispherical or semispherical shapes, shapes having sloped tapers or curved tapers, or shapes having non-uniform, irregular, or dimensionally varying tapers or contours, would also be suitable in any of the embodiment families.

In this regard, in this first embodiment family, the convex structure is configured as a flexible element and functions as a spring element that provides axial cushioning to the device. The convex structure has the socket of the ball and socket joint at its peak. In order to permit the flexible convex structure to flex under compressive loads applied to the device, it is a separate element from the second baseplate. In the preferred embodiment, the flexible convex structure is a belleville washer that has a frusto-conical shape. Other flexible convex structures are also contemplated as being suitable, such as, for example, convex structures that flex because of the resilience of the material from which they are made, because of the shape into which they are formed, and/or or because of the mechanical interaction between sub-elements of an assembly forming the convex structure. Although the convex structure is a separate element from the second baseplate in this embodiment family (so that it is able to flex), it is preferably maintained near the second baseplate so that the device does not separate in tension. Therefore, an extension of the second baseplate is provided (in the form of a shield element) to cover enough of the convex structure to so maintain it. Stated alternatively, the shield is a separate element from the second baseplate to ease manufacturing (during assembly, the flexible convex structure is first placed against the second baseplate, and then the shield is placed over the convex structure and secured to the second baseplate so that the convex structure is maintained between the second baseplate and the shield), but once the device is assembled, the second baseplate and the shield are effectively one element. That is, the second baseplate and shield can be considered to be a single integral housing within which the separate flexible convex structure flexes, because but for the sake of achieving desirable manufacturing efficiencies, the second baseplate and shield would be one piece.

Also in this regard, in the first embodiment family, the manner of capturing the ball in the socket is effected by the ball being selectively radially compressible. That is, the ball is radially compressed to fit into the socket and thereafter receives a deflection preventing element to prevent subsequent radial compression, so that the ball remains captured in the socket. A more detailed description of the preferred manner in which this is accomplished is described below. Because the socket is formed at the peak of the flexible convex structure discussed immediately above, the capturing of the ball in the socket in this manner allows the ball to remain securely held for rotation and angulation even though the socket moves upward and downward with the flexing of the convex structure. The second baseplate preferably includes an access hole that accommodates placement of the deflection preventing element, so that the same can be applied to the ball after the ball is fitted into the socket. Accordingly, the ball is maintained in the socket.

More specifically, in this preferred embodiment of the first embodiment family, with regard to joining the two baseplates 10,30 with a ball and socket joint, each of the baseplates 10,30 comprises features that, in conjunction with other components described below, form the ball and socket joint. More specifically, the first baseplate 10 includes an inwardly facing surface 18 that includes a perimeter region 20 and a ball 22 mounted to protrude from the inwardly facing surface 18. The ball 22 preferably has a semispherical shape defining a spherical contour. The ball 22 includes a series of slots 24 that render the ball 22 radially compressible and expandable in correspondence with a radial pressure (or a radial component of a pressure applied thereto and released therefrom). The ball 22 further includes an axial bore 26 that accepts a deflection preventing element (e.g., rivet, plug, dowel, or screw; a rivet 28 is used herein as an example) (shown in FIGS. 1*i*–*j*). (Alternatively, the axial bore can be threaded to accept a screw.) Prior to the insertion of the rivet 28, the ball 22 can deflect radially inward because the slots 24 will narrow under a radial pressure. The insertion of the rivet 28 eliminates the capacity for this deflection. Therefore, the ball 22, before receiving the rivet 28, can be compressed to pass into, and thereafter seat in, a central curvate socket of a convex structure (described below). Once the ball 22 has been seated in the curvate socket, the rivet 28 can be inserted into the axial bore 26 to ensure that the ball 22 remains held in the curvate socket. As described below, an access hole is preferably provided in the second baseplate 30 so that the interior of the device may be readily accessed for inserting the rivet 28 into the axial bore 26, or for other purposes.

The second baseplate 30 includes an inwardly facing surface 38 that includes a perimeter region 40 and a central circular recess 42 within which the wide end of the convex structure resides, and a pair of holes 44 through which rivets 46 (shown in FIGS. 1*g*–*h*) may be provided for securing a shield element 48 that is placed over the convex structure, which shield 48 thus serves as an extension of the second baseplate 30 (the shield 48 is more fully set forth below with and shown on FIGS. 1*i*–*j*).

Figure 1G:
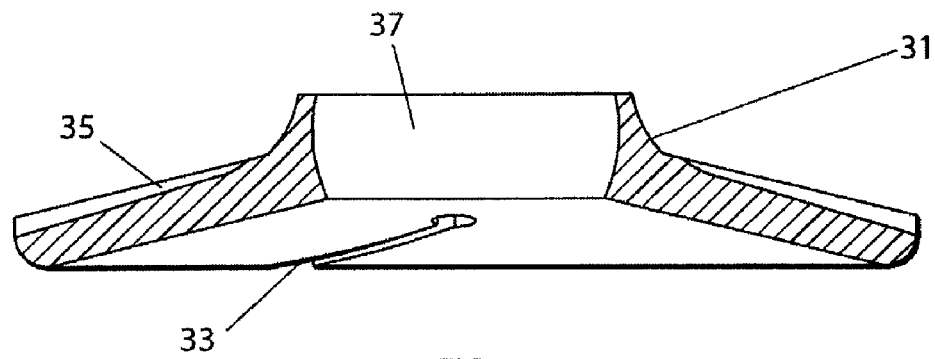
FIGS. 1g–h show side cutaway (FIG. 1g) and top perspective (FIG. 1h) views of a flexible convex structure of the first embodiment family, the flexible convex structure having spiral slots and radially extending grooves.
Figure 1H:
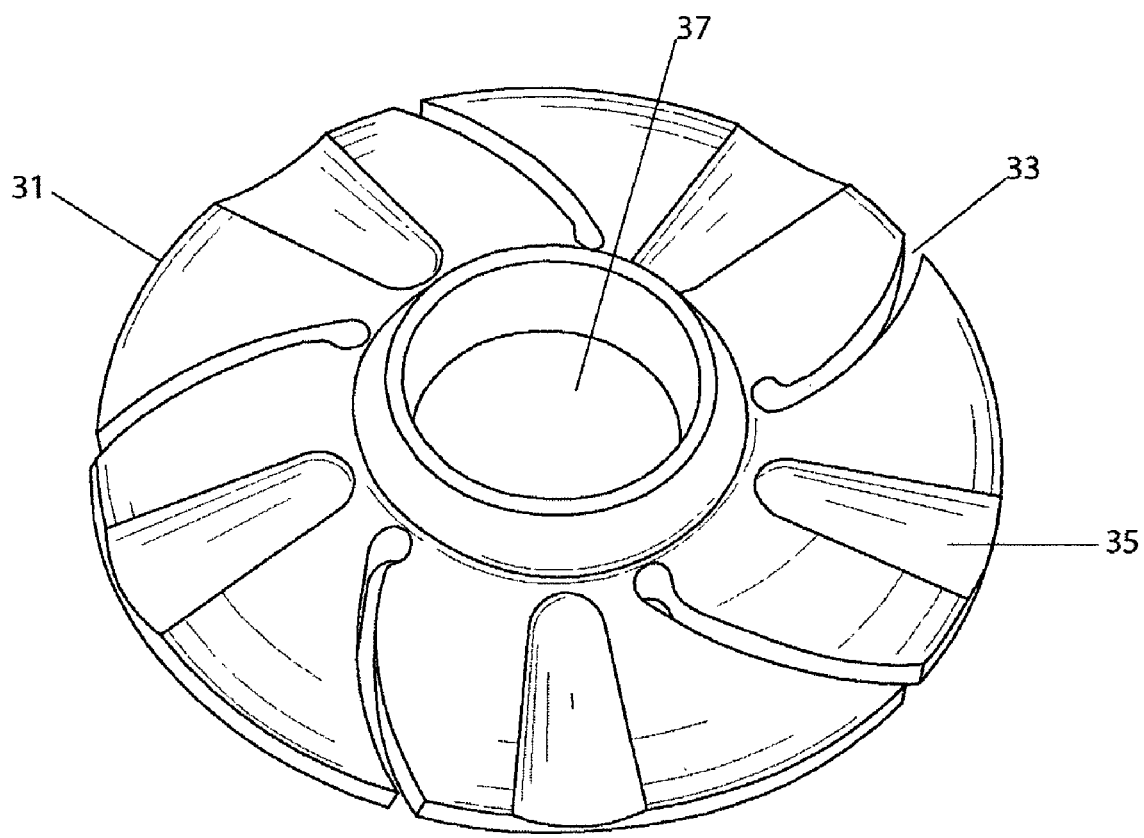

Referring now to FIGS. 1*g*–*h*, the convex structure 31 that resides in the circular recess 42 is shown in side cutaway (FIG. 1*g*) and top perspective (FIG. 1*h*) views. In this embodiment, the convex structure 31 is frusto-conical and is flexible. Because the convex structure 31 is flexible, it functions as a force restoring element (e.g., a spring) that provides axial cushioning to the device, by deflecting under a compressive load and restoring when the load is relieved. The flexible convex structure 31 is preferably, as shown, a belleville washer that has a frusto-conical shape. The belleville washer 31 preferably, as shown, has spiral slots and radially extending grooves. The restoring force of the belleville washer 31 is proportional to the elastic properties of the material or materials from which it is made. It should be understood that belleville washers having the configuration shown can be used with the present invention, but that belleville washers having other conformations, that is, without or without slots and/or grooves, and/or with other groove and slots configurations, including the same or different numbers of grooves and/or slots, can also be used with and are encompassed by the present invention.

The belleville washer 31 comprises a series of spiral slots 33 formed therein. The slots 33 extend from the outer edge of the belleville washer 31, inward along arcs generally directed toward the center of the element. The slots 33 do not extend fully to the center of the element. Preferably, the slots 33 extend anywhere from a quarter to three quarters of the overall radius of the washer 31, depending upon the requirements of the patient, and the anatomical requirements of the device.

The belleville washer 31 further comprises a series of grooves 35 formed therein. The grooves 35 extend radially from the outer edge of the belleville washer 31 toward the center of the element. Preferably, the width and depth of each groove 35 decreases along the length of the groove 35 from the outer edge of the washer 31 toward the center of the washer 31, such that the center of the washer 31 is flat, while the outer edge of the washer 31 has grooves of a maximum groove depth. It should be understood that in other embodiments, one or both of the depth and the width of each groove can be (1) increasing along the length of the groove from the outer edge of the washer toward the center of the washer, (2) uniform along the length of the groove from the outer edge of the washer toward the center of the washer, or (3) varied along the length of each groove from the outer edge of the washer toward the center of the washer, either randomly or according to a pattern. Moreover, in other embodiments, it can be the case that each groove is not formed similarly to one or more other grooves, but rather one or more grooves are formed in any of the above-mentioned fashions, while one or more other grooves are formed in another of the above-mentioned fashions or other fashions. It should be clear that any groove pattern can be implemented without departing from the scope of the present invention, including, but not limited to, at least one radially spaced concentric groove, including, but not limited to, at least one such groove having at least one dimension that varies along the length of the groove. Belleville washers having circumferential extents that radially vary in at least one dimension, are also contemplated by the present invention.

As a compressive load is applied to the belleville washer 31, the forces are directed into a hoop stress which tends to radially expand the washer 31. This hoop stress is counterbalanced by the material strength of the washer 31, and the force necessary to widen the spiral slots 33 and the radial grooves 35 along with the strain of the material causes a deflection in the height of the washer 31. Stated equivalently, the belleville washer 31 responds to a compressive load by deflecting compressively; the spiral slots and/or radial grooves cause the washer to further respond to the load by spreading as the slots and/or the grooves in the washer expand under the load. The spring, therefore, provides a restoring force which is proportional to the elastic modulus of the material in a hoop stressed condition.

With regard to the above discussion regarding the curvate socket that receives the ball 22 of the first baseplate 10, the curvate socket is formed at the peak of the convex structure 31. The curvate socket 37 is provided inasmuch as the central opening of the belleville washer 31 is enlarged. This central opening includes a curvate volume 37 for receiving therein the ball 22 of the first baseplate 10. More particularly, the curvate volume 37 has a substantially constant radius of curvature that is also substantially equivalent to the radius of the ball 22. In this embodiment, the spiral slots 33 of the washer 31 do not extend all the way to the central opening, and approach the opening only as far as the material strength of the washer 31 can handle without plastically deforming under the expected anatomical loading. Further in this embodiment, the depth of each groove 35 of the washer 31 decreases along the length of the groove 35 from the outer edge of the washer 31 toward the center of the washer 31, such that the center of the washer 31 is flat, while the outer edge of the washer 31 has grooves of a maximum groove depth. Therefore, the central opening can be formed from flat edges. It should be understood that this is not required, but rather is preferred for this embodiment.

The curvate socket 37 has an opening diameter that accommodates passage therethrough of the ball 22 in a radially compressed state (but not in an uncompressed state), and a larger inner diameter that accommodates the ball 22 in the uncompressed state. Therefore, the ball 22 can be radially compressed to pass into the curvate socket 37 under force, and then will radially expand to the uncompressed state once in the curvate socket 37. Once the rivet 28 is then secured into the axial bore 26, the rivet 28 prevents the ball 22 from radially compressing, and therefore the ball 22 cannot back out through the opening. An access hole 39 in the second baseplate 30 below the curvate socket 37 has a diameter that accommodates the diameter of the rivet 28 and thereby provides easy access to insert the rivet 28 in the axial bore 26 after the ball 22 has been seated in the curvate socket 37. To prevent the ball 22 from escaping the curvate socket 37 through the second baseplate 30, the diameter of the access hole 39 is smaller than the inner diameter of the curvate socket 37.

The curvate socket 37 defines a spherical contour that closely accommodates the ball 22 for free rotation and angulation in its uncompressed state. Therefore, when seated in the curvate socket 37, the ball 22 can rotate and angulate freely relative to the curvate socket 37 through a range of angles, thus permitting the opposing baseplates 10,30 to rotate and angulate freely relative to one another through a corresponding range of angles equivalent to the fraction of normal human spine rotation and angulation (to mimic normal disc rotation and angulation). Further preferably, the perimeter regions 20,40 have corresponding contours, so that the meeting of the perimeter regions 20,40 as a result of the angulation of the baseplates 10,30 reduces any surface wearing.

Figure 1I:
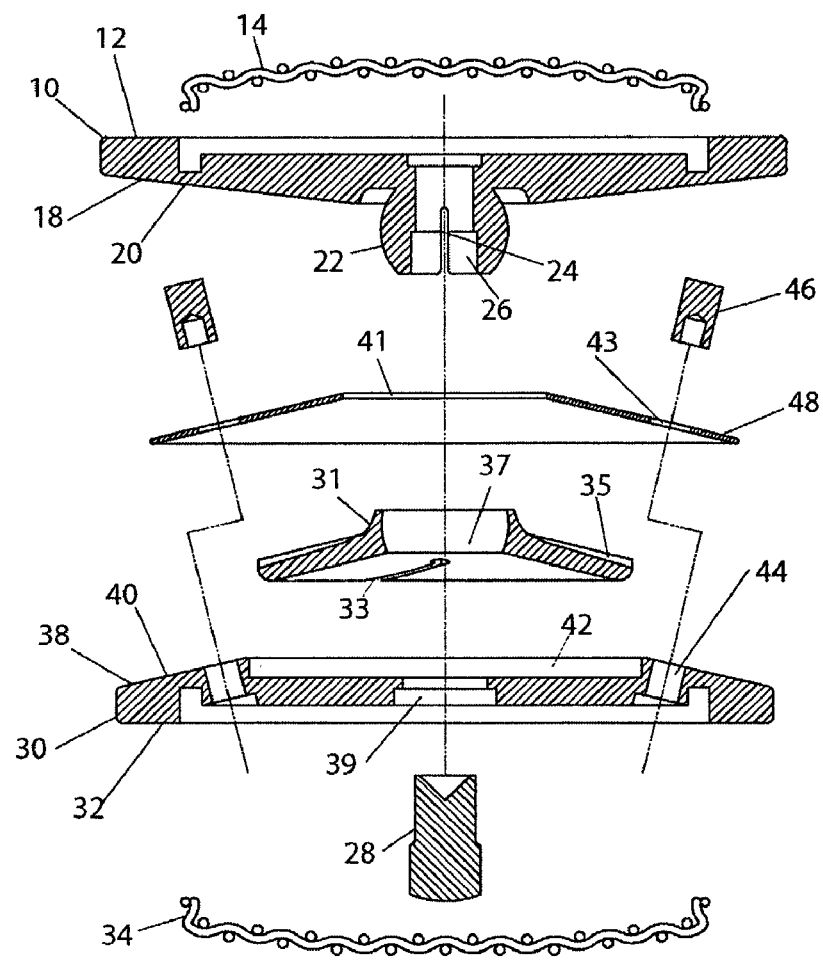
FIGS. 1i–j show exploded (FIG. 1i) and assembled (FIG. 1j) views of a preferred embodiment of the first embodiment family.
Figure 1J:
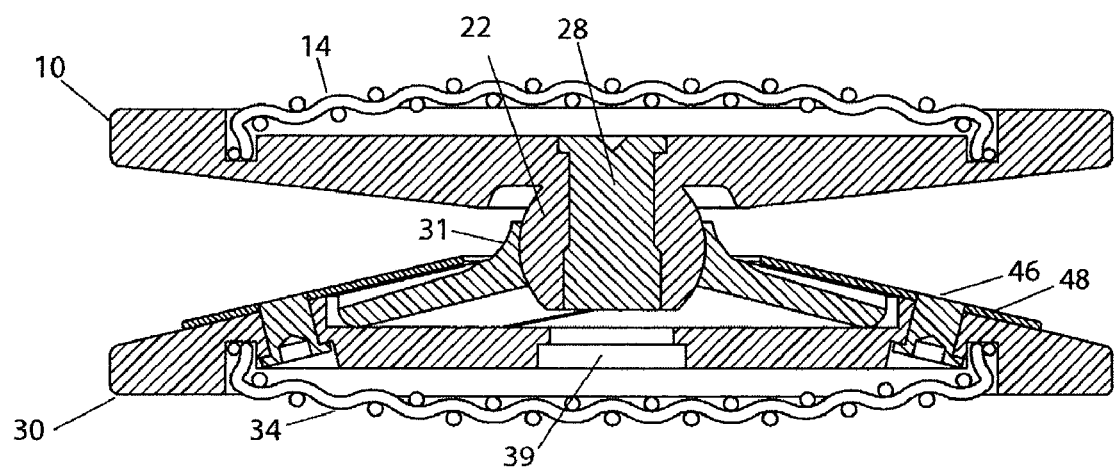

Referring to FIGS. 1*i–j*, exploded (FIG. 1*i*) and assembled (FIG. 1*i*) views of the preferred embodiment of the first embodiment family are shown. Included in these views are the shield 48 and the corresponding rivets 46. More particularly, assembly of the disc is preferably as follows. The first and second baseplates 10,30 are disposed so that their outwardly facing surfaces 12,32 face away from one another and their inwardly facing surfaces 18,38 are directed toward one another. The convex structure 31 is then positioned with its wide end in the circular recess 42 of the second baseplate, so that the curvate socket 37 of the convex structure 31 is aligned with the ball 22 of the first baseplate 10. Then, the shield 48 is secured over the belleville washer 31 (the shield 48 is preferably frusto-conical to follow the shape of the belleville washer 31, although other shield shapes are suitable and contemplated by the present invention) by passing the central hole 41 of the shield 48 over the curvate socket 37 and applying the rivets 46 through rivet holes 43 in the shield 48 and into the rivet holes 44 in the second baseplate 30. Then, the ball 22 is pressed into the curvate socket 37 under a force sufficient to narrow the slots 24 and thereby radially compress the ball 22 until the ball 22 fits through and passes through the opening of the curvate socket 37. Once the ball 22 is inside the curvate socket 37, the ball 22 will radially expand as the slots 24 widen until it has returned to its uncompressed state and the spherical contour defined by the ball 22 is closely accommodated by the spherical contour defined by the curvate socket 37 and the ball 22 can rotate and angulate freely relative to the curvate socket 37. Thereafter, the rivet 28 is passed through the access hole 39 and pressed into the axial bore 26 of the ball 22 to prevent any subsequent radially compression of the ball 22 and therefore any escape from the curvate socket 37 thereby. Because the diameter of the circular recess 42 is greater than the diameter of the wide end of the belleville washer 31, compressive loading of the device (and therefore the belleville washer) can result in an unrestrained radial deflection of the belleville washer 31. The spiral slots 33 and radial grooves 35 of the belleville washer 31 enhance this deflection. When the load is removed, the belleville washer 31 springs back to its original shape.

Accordingly, when the device of the preferred embodiment of the first embodiment family is assembled, the baseplates 10,30 are rotatable relative to one another because the ball 22 rotates freely within the curvate socket 37, and angulatable relative to one another because the ball 22 angulates freely within the socket 37. Because the convex structure 31 is flexible (and is housed in the second baseplate 30 in a manner that permits it to flex), the baseplates 10,30 are also axially compressible relative to one another. Because the ball 22 is held within the curvate socket 37 by a rivet 28 in the axial bore 26 preventing radial compression of the ball 22, the artificial disc can withstand tension loading of the baseplates 10,30. More particularly, when a tension load is applied to the baseplates 10,30, the ball 22 in the curvate socket 37 seeks to radially compress to fit through the opening of the curvate socket 37. However, the rivet 28 in the axial bore 26 of the ball 22 prevents the radial compression, thereby preventing the ball 22 from exiting the curvate socket 37. Therefore, the assembly does not come apart under normally experienced tension loads. This ensures that no individual parts of the assembly will pop out or slip out from between the vertebral bodies when, e.g., the patient stretches or hangs while exercising or performing other activities. Thus, in combination with the securing of the baseplates 10,30 to the adjacent vertebral bones via the mesh domes 14,34, the disc assembly has an integrity similar to the tension-bearing integrity of a healthy natural intervertebral disc. Also, because the ball 22 is laterally captured in the curvate socket 37, lateral translation of the baseplates 10,30 relative to one another is prevented during rotation and angulation, similar to the performance of healthy natural intervertebral disc. Because the baseplates 10,30 are made angulatable relative to one another by the ball 22 being rotatably and angulatably coupled in the curvate socket 37, the disc assembly provides a centroid of motion within the ball 22. Accordingly, the centroid of motion of the disc assembly remains centrally located between the vertebral bodies, similar to the centroid of motion in a healthy natural intervertebral disc.

A preferred embodiment of a second embodiment family of the present invention will now be described.

Figure 2A:
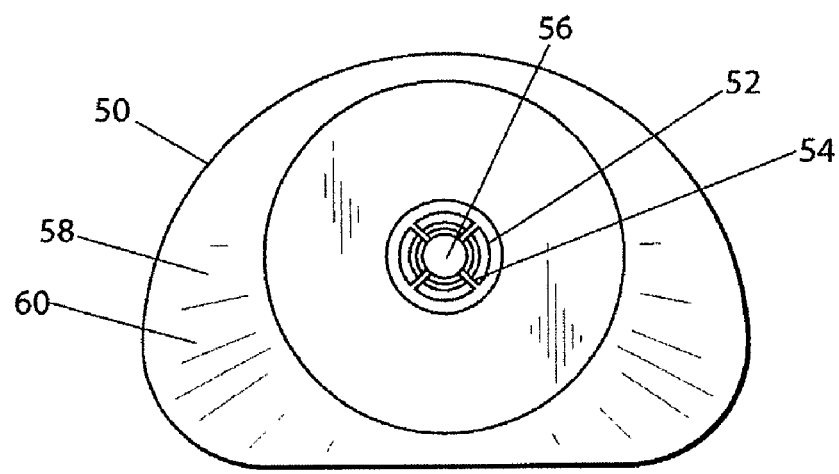
FIGS. 2a–c show top (FIG. 2a), side cutaway (FIG. 2b) and bottom (FIG. 2c) views of a first baseplate of a second embodiment family of the present invention, the first baseplate having an inwardly directed radially compressible ball.
Figure 2B:
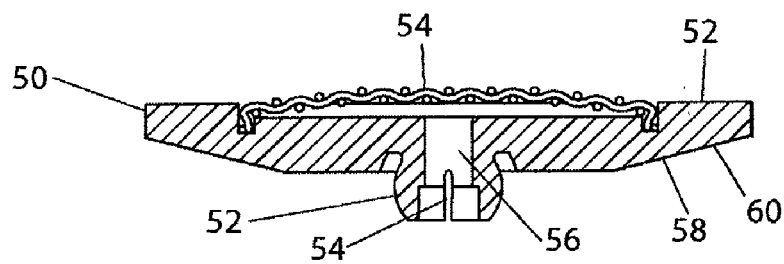
Figure 2C:
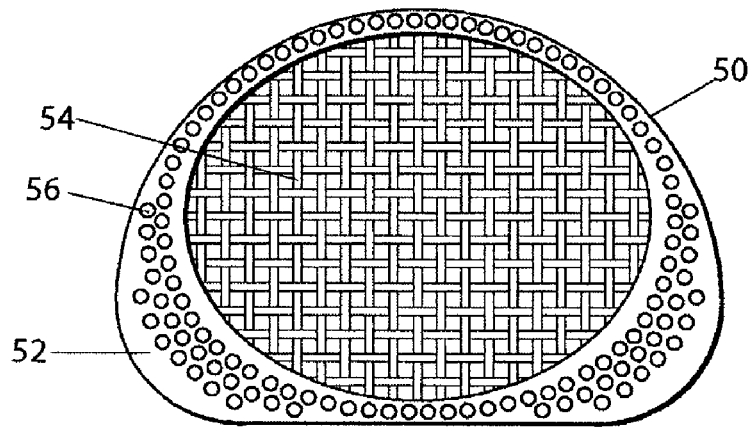
Figure 2D:
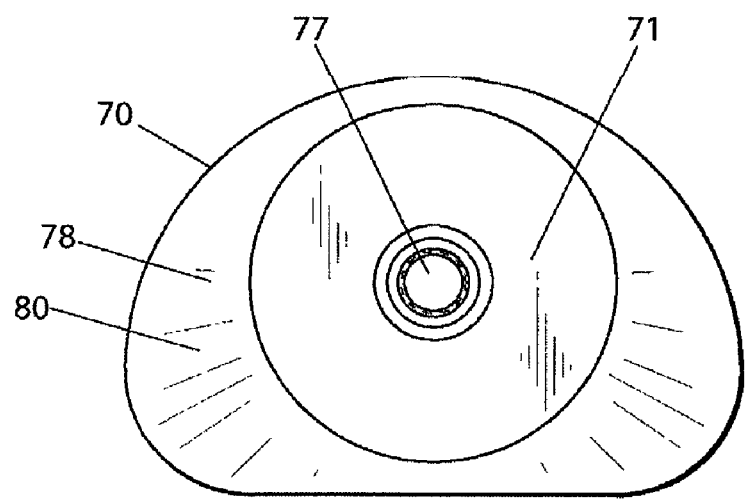
FIGS. 2d–f show top (FIG. 2d), side cutaway (FIG. 2e) and bottom (FIG. 2f) views of a second baseplate of the second embodiment family, the second baseplate having a curvate socket within which the ball is capturable for free rotation and angulation therein.
Figure 2E:
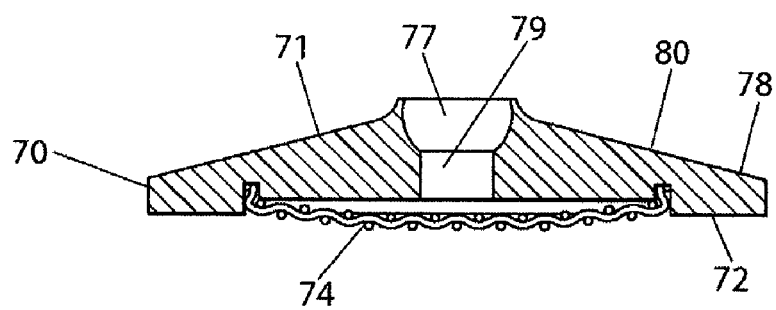
Figure 2F:
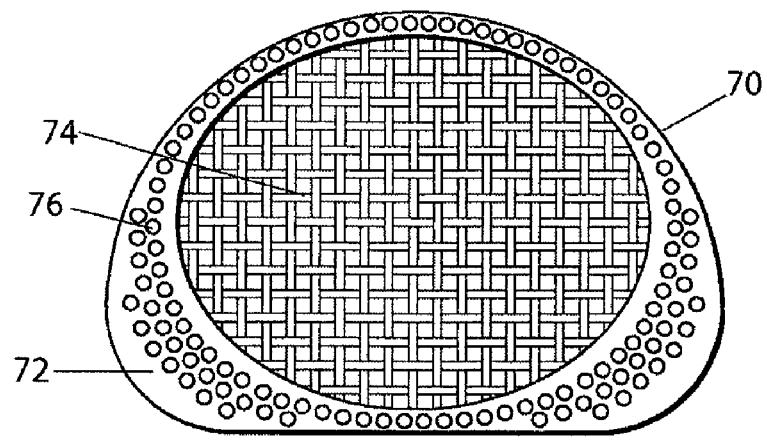

Referring to FIGS. 2*a–c*, a first baseplate 50 of a second embodiment family of the present invention is shown in top (FIG. 2*a*), side cutaway (FIG. 2*b*) and bottom (FIG. 2*c*) views. Also referring to FIGS. 2*d–f*, a second baseplate 70 of the second embodiment family is shown in top (FIG. 2*d*), side cutaway (FIG. 2*e*) and bottom (FIG. 2*f*) views.

With regard to the configuration of the convex structure in this second embodiment family, and the manner in which the ball is captured in the socket in this second embodiment family, the convex structure is configured as a non-flexible element that is integral with the second baseplate, and has the socket of the ball and socket joint at its peak. More clearly stated, the devices of this second embodiment family do not feature a flexible convex structure, and therefore (and also because of the manner in which the ball is captured in this second embodiment family, discussed immediately below) there is no need for the convex structure to be a separate element from the second baseplate. (By contrast, in the first embodiment family, as discussed above, because the convex structure is flexible, it is separated from the second baseplate so that it is able to flex.) In the preferred embodiment, the convex structure has a frusto-conical shape. The manner of capturing the ball in the socket in this second embodiment family is identical to that of the first embodiment family.

More specifically, the first and second baseplates 50,70 are similar to the first and second baseplates 10,30 of the first embodiment family described above with regard to each outwardly facing surface 52,72 having a vertebral body contact element 54,74 and an adjacent osteoconductive ring 56,76, and each inwardly facing surface 58,78 having a perimeter region 60,80, all of which elements in the second embodiment family are, for example, identical to the corresponding elements in the first embodiment family as described above.

Further, as with the first embodiment family, the two baseplates 50,70 are joined with a ball and socket joint, and therefore each of the baseplates 50,70 comprises features that, in conjunction with other components described below, form the ball and socket joint. More specifically, the first baseplate 50 is formed similarly to the first baseplate 10 of the first embodiment family, having a ball 62 mounted to protrude from the inwardly facing surface 58. The ball 62 preferably has a semispherical shape defining a spherical contour. The ball 62 is structurally and functionally identical to the ball 22 of the first embodiment family, and as such is selectively radially compressible in the same manner as the ball 22 of the first embodiment family. As with the ball 22 of the first embodiment family, the ball 62 is capturable in a curvate socket 77 formed at the peak of a convex structure 71 protruding from the second baseplate 70. The curvate socket 77 is functionally and structurally identical to the curvate socket 37 of the first embodiment family. However, in this second embodiment family, the convex structure 77 of the device, rather than being a flexible separate element from the second baseplate as in the first embodiment family, is integral with the second baseplate 70. The convex structure 77 is frusto-conical, but is not flexible, and therefore does not function as a force restoring element as does the flexible convex structure 37 in the first embodiment family. Access to the convex structure 77 for providing easy access to insert the rivet 68 in the axial bore 66 of the ball 62 after the ball 62 has been seated in the curvate socket 77 is provided by an access hole 79 in the second baseplate 70 below and leading to the curvate socket 77. The access hole 79 is otherwise structurally identical to the access hole 39 in the second baseplate 30 of the first embodiment family.

Figure 2G:
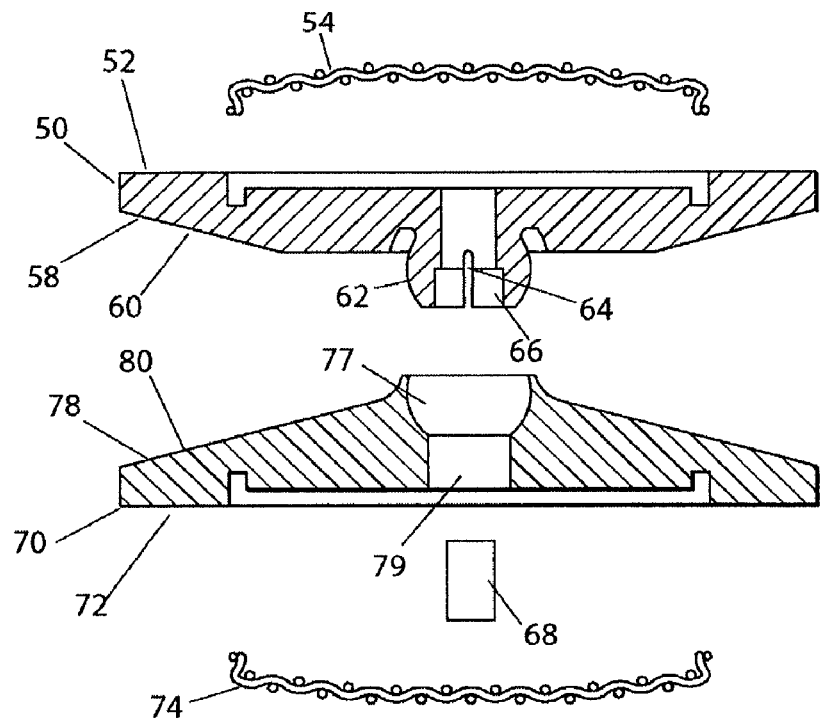
FIGS. 2g–h show exploded (FIG. 2g) and assembled (FIG. 2h) views of a preferred embodiment of the second embodiment family.
Figure 2H:
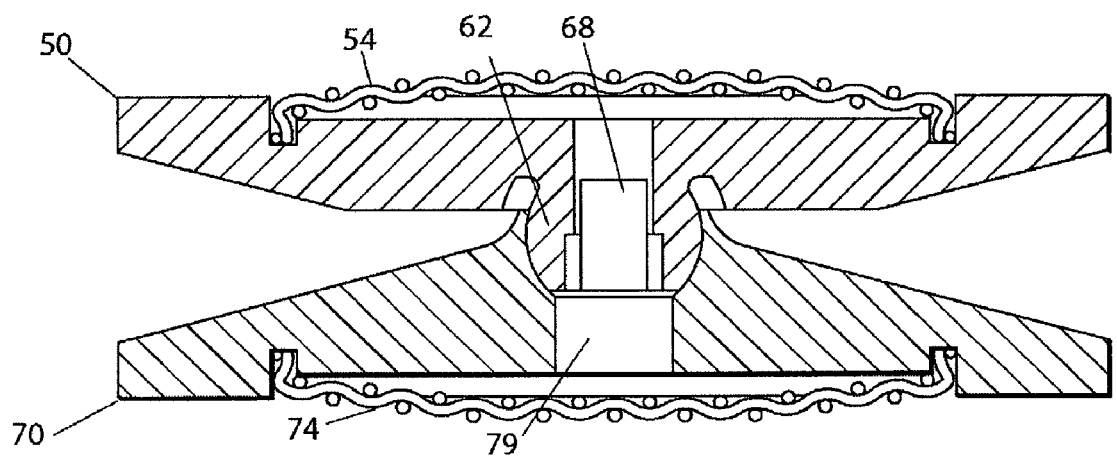
Figure 3A:
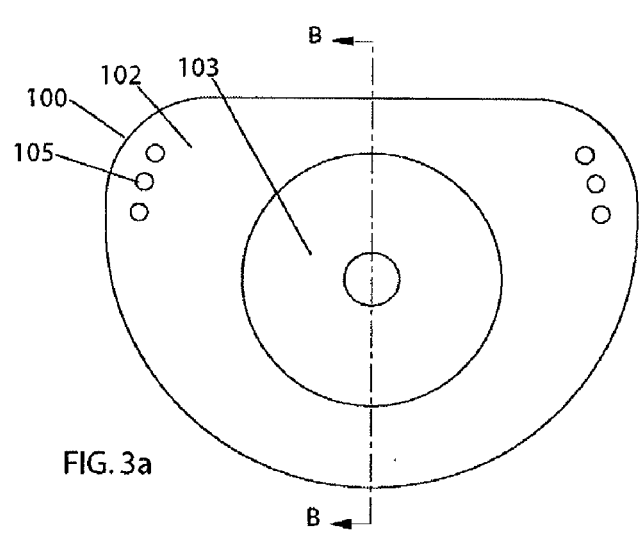
FIGS. 3a–e show top (FIG. 3a), side (FIG. 3b), side cutaway (FIG. 3c), perspective cutaway (FIG. 3d) and perspective (FIG. 3e) views of a first baseplate of a third embodiment family of the present invention.
Figure 3C:
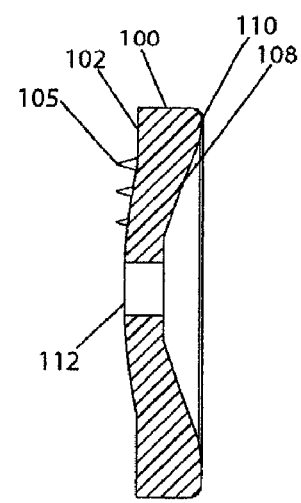
Figure 3B:
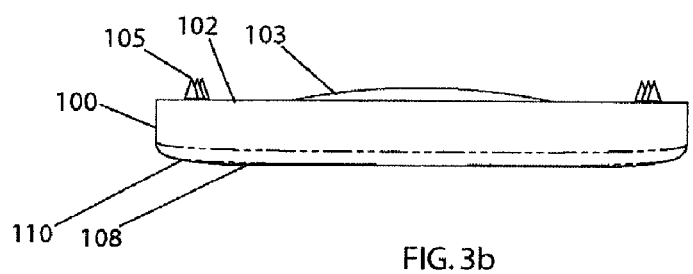
Figure 3D:
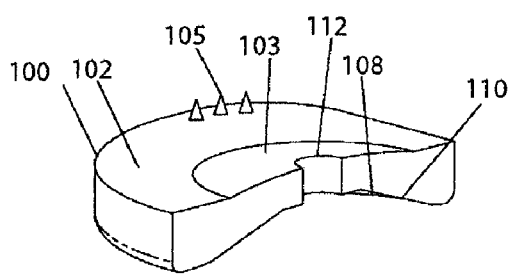
Figure 3E:
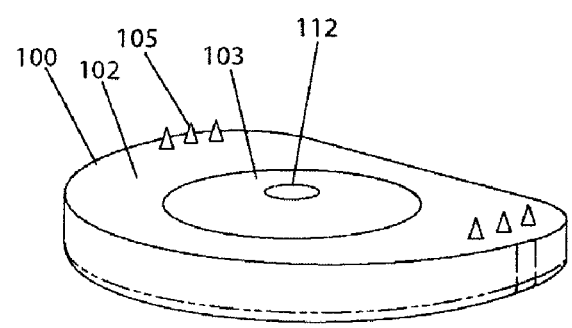
Figure 5F:
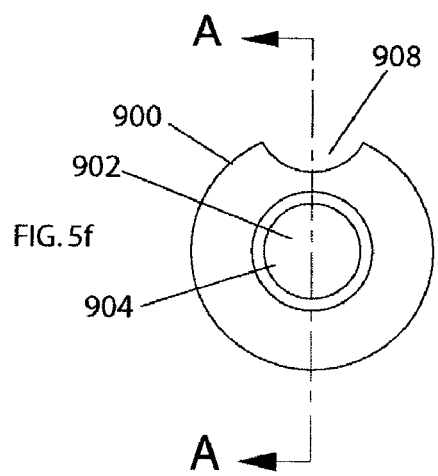
FIGS. 5f–j show top (FIG. 5f), side (FIG. 5g), side cutaway (FIG. 5h), perspective cutaway (FIG. 5i) and perspective (FIG. 5j) views of a third type of the ball of the third embodiment family, the third type of the ball having a curvate recess.
Figure 5H:
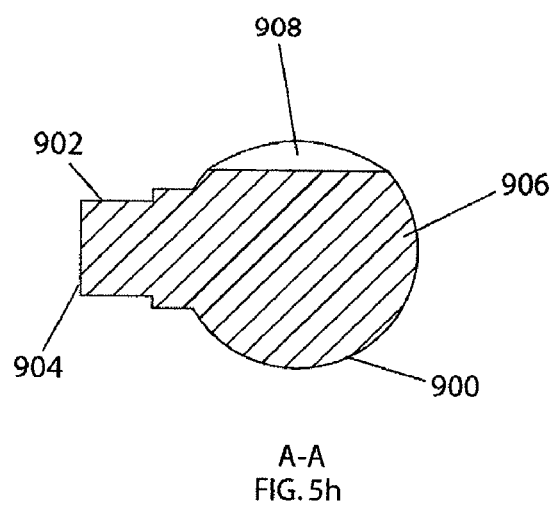
Figure 5G:
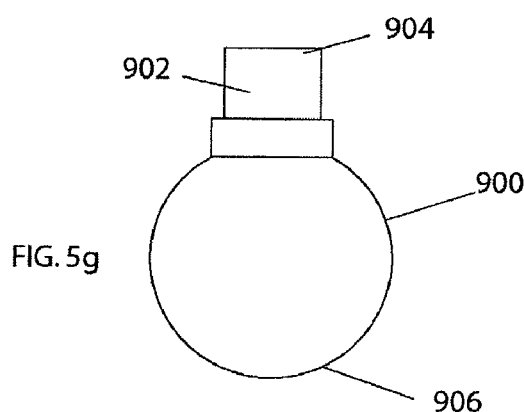
Figure 5I:
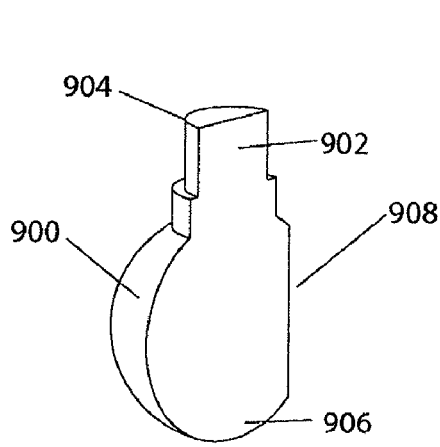
Figure 5J:
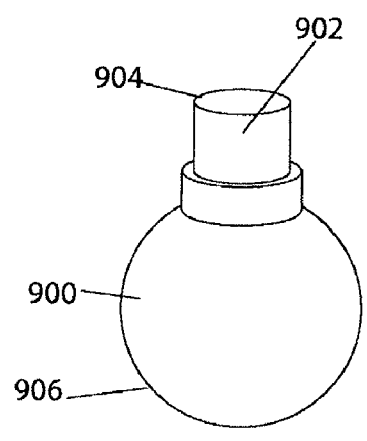
Figure 8K:
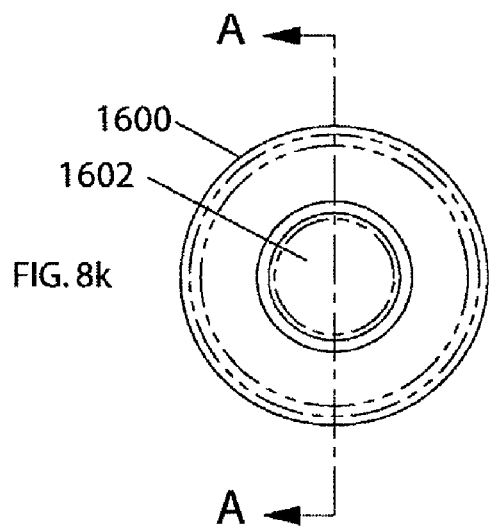
FIGS. 8*k–o* show top (FIG. 8*k*), side (FIG. 8*l*), side cutaway (FIG. 8*m*), perspective cutaway (FIG. 8*n*) and perspective (FIG. 8*o*) views of a first type of a ball of the fourth embodiment family.
Figure 8M:
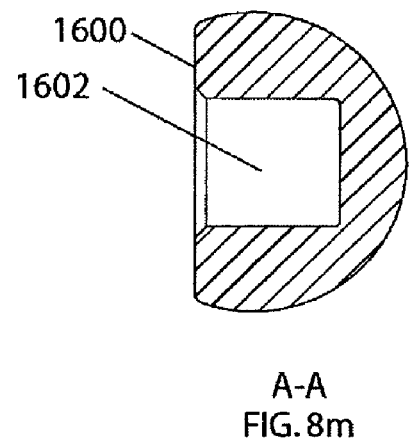
Figure 8L:
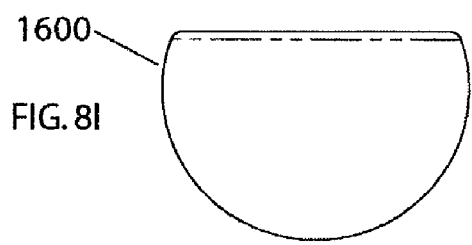
Figure 8N:
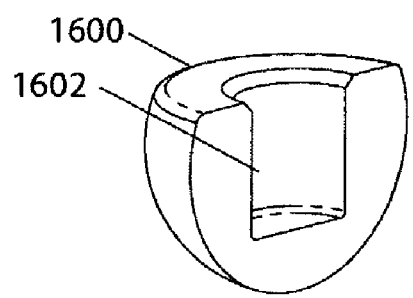
Figure 8O:
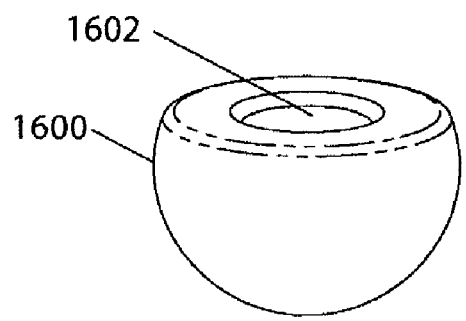
Figure 9F:
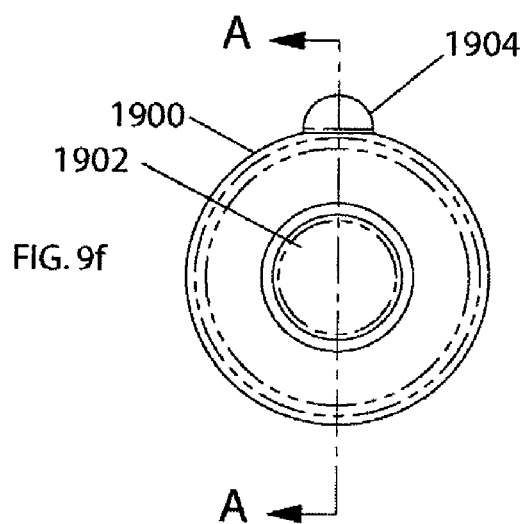
FIGS. 9*f–j* show top (FIG. 9*f*), side (FIG. 9*g*), side cutaway (FIG. 9*h*), perspective cutaway (FIG. 9*i*) and perspective (FIG. 9*j*) views of a second type of the ball of the fourth embodiment family, the second type of the ball having a protrusion.
Figure 9H:
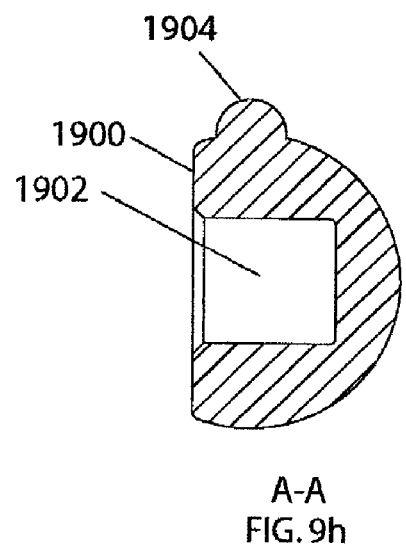
Figure 9G:
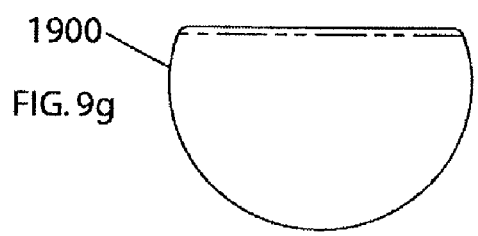
Figure 9I:
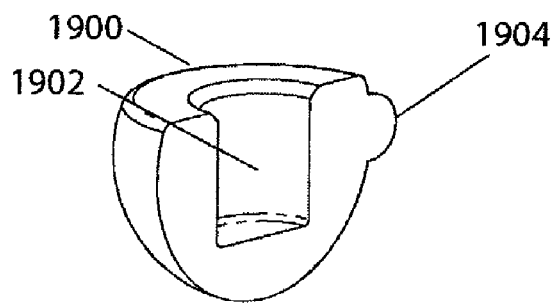
Figure 9J:
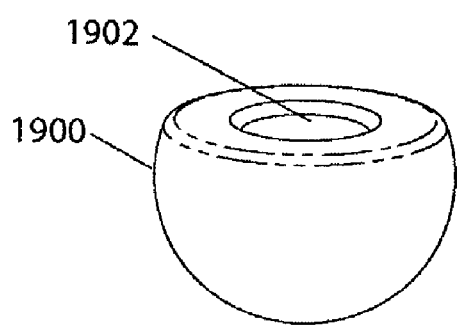
Figure 10F:
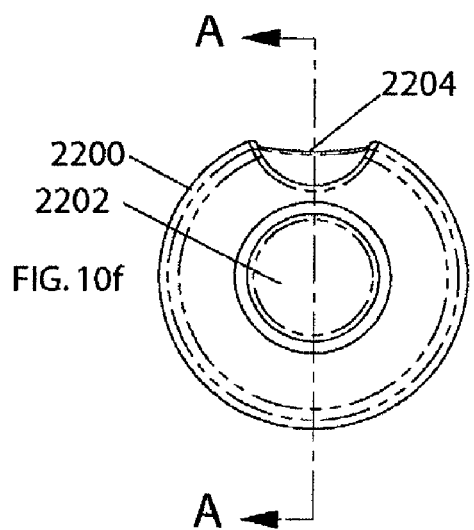
FIGS. 10*f–j* show top (FIG. 10*f*), side (FIG. 10*g*), side cutaway (FIG. 10*h*), perspective cutaway (FIG. 10*i*) and perspective (FIG. 10*j*) views of a third type of the ball of the fourth embodiment family, the third type of the ball having a curvate recess.
Figure 10H:
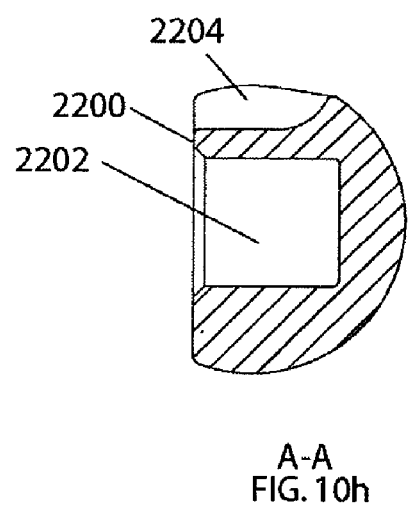
Figure 10G:
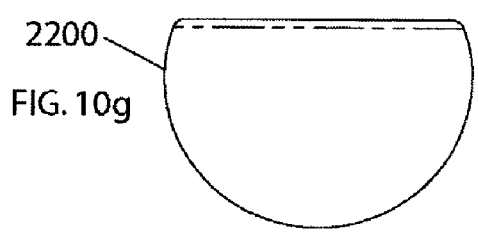
Figure 10I:
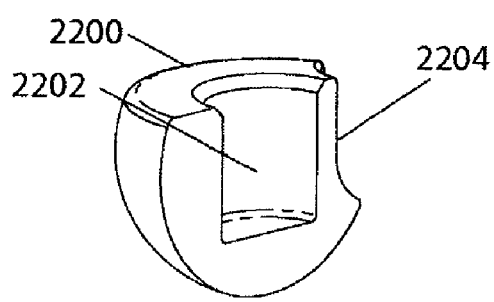
Figure 10J:
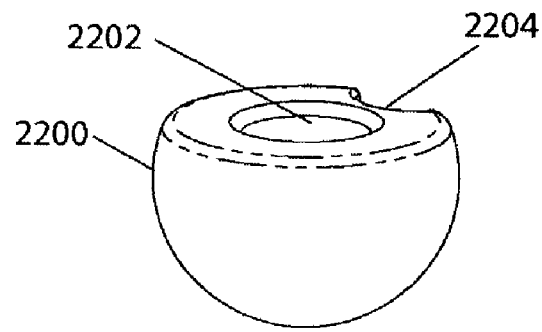
Figure 12F:
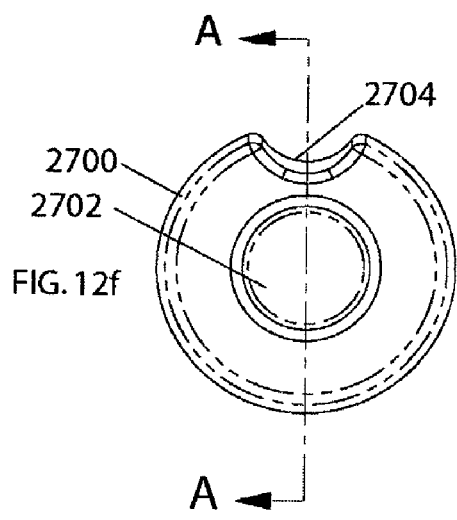
FIGS. 12*f–j* show top (FIG. 12*f*), side (FIG. 12*g*), side cutaway (FIG. 12*h*), perspective cutaway (FIG. 12*i*) and perspective (FIG. 12*j*) views of fourth type of ball of the fourth embodiment family, the fourth type of ball having a curvate recess.
Figure 12H:
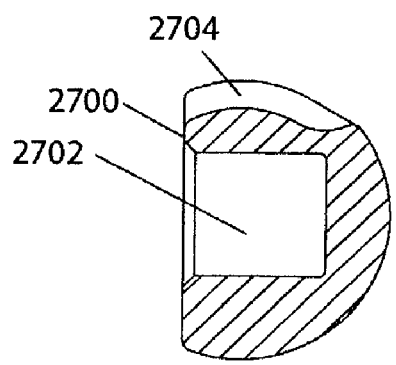
Figure 12G:
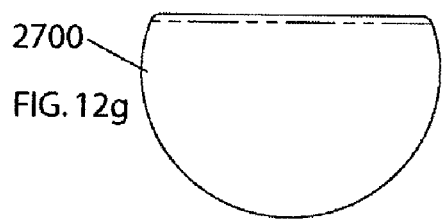
Figure 12I:
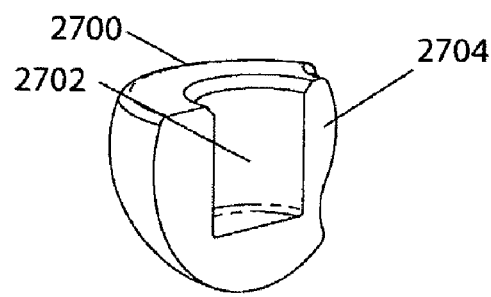
Figure 12J:
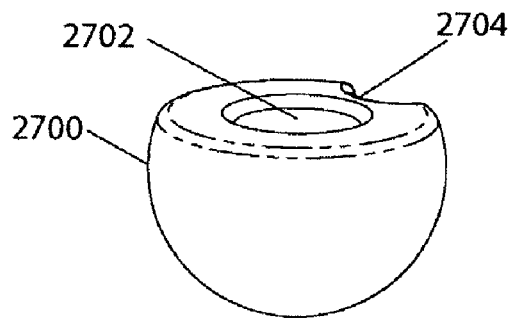
Figure 13:
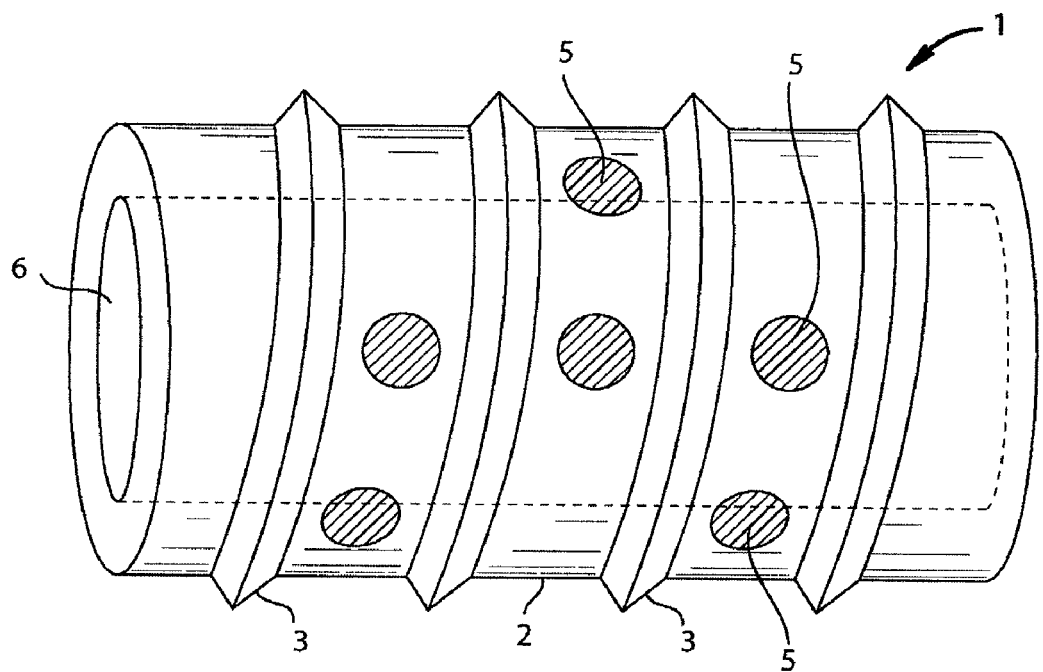
FIG. 13 shows a side perspective view of a prior art interbody fusion device.
Figure 14:
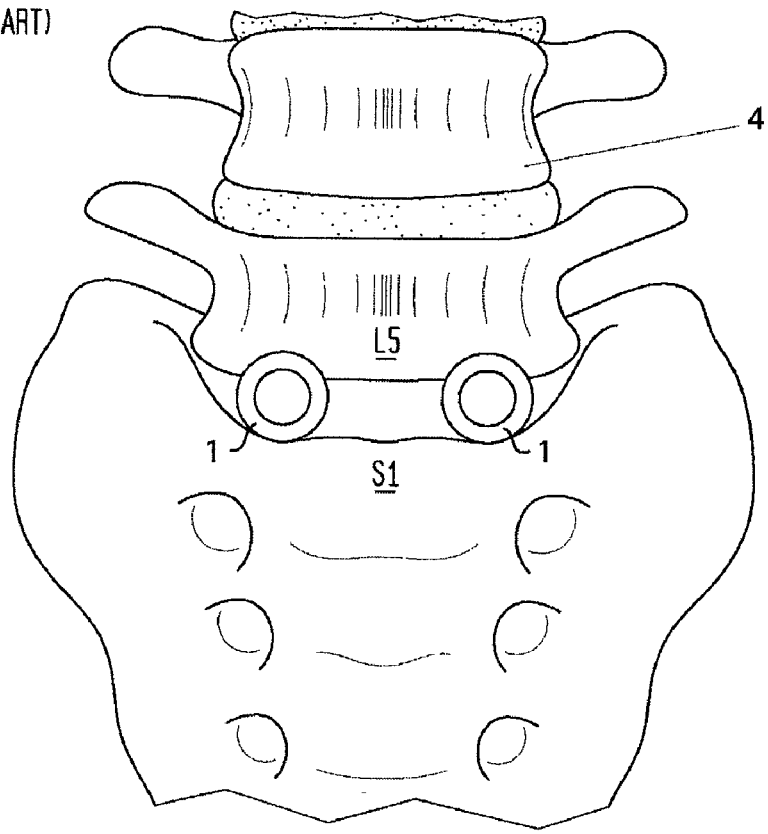
FIG. 14 shows a front view of the anterior portion of the lumbo-sacral region of a human spine, into which a pair of interbody fusion devices of FIG. 13 have been implanted.

Referring to FIGS. 2g–h, an assembled preferred embodiment of the second embodiment family is shown in exploded (FIG. 2g) and assembled (FIG. 2h) views. More particularly, assembly of the disc is preferably as follows. The first and second baseplates 50,70 are disposed so that their outwardly facing surfaces 52,72 face away from one another and their inwardly facing surfaces 58,78 are directed toward one another, and so that the ball 62 of the first baseplate 50 is aligned with the curvate socket 77 of the convex structure 71 of the second baseplate 70. Then, the ball 62 is pressed into the curvate socket 77 under a force sufficient to narrow the slots 64 and thereby radially compress the ball 62 until the ball 62 fits through and passes through the opening of the curvate socket 77. Once the ball 62 is inside the curvate socket 77, the ball 62 will radially expand as the slots 64 widen until it has returned to its uncompressed state and the spherical contour defined by the ball 62 is closely accommodated by the spherical contour defined by the curvate socket 77 and the ball 62 can rotate and angulate freely relative to the curvate socket 77. Thereafter, the rivet 68 is passed through the access hole 79 and pressed into the axial bore 66 of the ball 62 to prevent any subsequent radially compression of the ball 62 and therefore any escape from the curvate socket 77 thereby.

Accordingly, when the device of the preferred embodiment of the second embodiment family is assembled, the baseplates 50,70 are rotatable relative to one another because the ball 62 rotates freely within the curvate socket 77, and angulatable relative to one another because the ball 62 angulates freely within the socket 77. Because the ball 62 is held within the curvate socket 77 by a rivet 68 in the axial bore 66 preventing radial compression of the ball 62, the artificial disc can withstand tension loading of the baseplates 50,70. More particularly, when a tension load is applied to the baseplates 50,70, the ball 62 in the curvate socket 77 seeks to radially compress to fit through the opening of the curvate socket 77. However, the rivet 68 in the axial bore 66 of the ball 62 prevents the radial compression, thereby preventing the ball 62 from exiting the curvate socket 77. Therefore, the assembly does not come apart under normally experienced tension loads. This ensures that no individual parts of the assembly will pop out or slip out from between the vertebral bodies when, e.g., the patient stretches or hangs while exercising or performing other activities. Thus, in combination with the securing of the baseplates 50,70 to the adjacent vertebral bones via the mesh domes 54,74, the disc assembly has an integrity similar to the tension-bearing integrity of a healthy natural intervertebral disc. Also because the ball 62 is laterally captured in the curvate socket 77, lateral translation of the baseplates 50,70 relative to one another is prevented during rotation and angulation, similar to the performance of healthy natural intervertebral disc. Because the baseplates 50,70 are made angulatable relative to one another by the ball 62 being rotatably and angulatably coupled in the curvate socket 77, the disc assembly provides a centroid of motion within the ball 62. Accordingly, the centroid of motion of the disc assembly remains centrally located between the vertebral bodies, similar to the centroid of motion in a healthy natural intervertebral disc.

Embodiments of the third embodiment family of the present invention will now be described.

With regard to the configuration of the convex structure in the third embodiment family, the convex structure is configured as a non-flexible element that is integral with the second baseplate, and has the socket of the ball and socket joint at its peak, similar to the configuration of the convex structure in the second embodiment family. In the preferred embodiment, the convex structure is shaped to have a curved taper.

With regard to the manner in which the ball is captured in the socket in the third embodiment family, the capturing is effected through the use of a solid ball. In order to permit the seating of the ball into the socket formed at the peak of the convex structure, the access hole in the second baseplate has a diameter that accommodates the diameter of the ball, and leads to the interior of the peak, which interior is formed as a concavity having an opening diameter that accommodates the diameter of the ball. (Preferably, the concavity has a curvature closely accommodating the contour of the ball, and the concavity is either hemispherical or less-than-hemispherical so that the ball can easily be placed into it.) Further, in order to maintain the ball in the socket, an extension of the second baseplate (in the form of a cap element) is provided for sealing the access hole in the second baseplate (or reducing the opening diameter of the hole to a size that does not accommodate the diameter of the ball). The cap has an interior face that preferably has a concavity (that has a curvature that closely accommodates the contour of the ball) to complete the socket. The peak of the convex structure has a bore that accommodates a post to which the ball and the first baseplate are attached (one to each end of the post), but does not accommodate the ball for passage through the bore. Accordingly, the ball is maintained in the socket.

A first preferred embodiment of a third embodiment family of the present invention will now be described.

Referring to FIGS. 3a–e, a first baseplate 100 of the third embodiment family of the present invention is shown in top (FIG. 3a), side (FIG. 3b), side cutaway (FIG. 3c), perspective cutaway (FIG. 3d) and perspective (FIG. 3e) views. Also referring to FIGS. 3f–j, a first type 200 of a second baseplate of the third embodiment family is shown in top (FIG. 3f), side (FIG. 3g), side cutaway (FIG. 3h), perspective cutaway (FIG. 3i) and perspective (FIG. 3j) views.

More specifically, the first and second baseplates 100,200 are similar to the first and second baseplates 50,70 of the second embodiment family described above with regard to each having an outwardly facing surface 102,202, and each inwardly facing surface 108,208 having a perimeter region 110,210, all of which elements in the third embodiment family are, for example, identical to the corresponding elements in the first embodiment family as described above. However, each of the first and second baseplates 100,200 in this second embodiment family instead of having a convex mesh as a vertebral body contact element, have a convex solid dome 103,203 and a plurality of spikes 105,205 as vertebral body contact element. Preferably, the dome 103, 203 is covered with an osteoconductive layer of a type known in the art. It should be noted that the convex solid dome 203 of the second baseplate 200 is provided in this embodiment (and the other embodiments in this family) by the cap element (described below) that serves as an extension of the second baseplate 200 to capture the ball (described below), as best shown in FIGS. 3u–y. It should also be noted that the convex mesh used in other embodiments of the present invention is suitable for use with these other vertebral body contact elements, and can be attached over the convex dome 103,203 by laser welding, or more preferably, by plasma burying (where the perimeter region of the convex mesh is buried under a plasma coating, which coating secures to the outwardly facing surface of the baseplate to which it is applied, and thus secures the convex mesh to the outwardly facing surface).

Further, as with the first embodiment family, the two baseplates 100,200 are joined with a ball and socket joint, and therefore each of the baseplates 100,200 comprises features that, in conjunction with other components described below, form the ball and socket joint. The ball and socket joint includes a solid ball (described below) mounted to protrude from the inwardly facing surface 108 of the first baseplate 100, and a curvate socket formed at a peak of a non-flexible convex structure (described below) that is integral with the second baseplate 200, within which curvate socket the ball is capturable for free rotation and angulation therein. As shown in FIGS. 3a–e, the mounting for the ball includes a central hole 112 on the inwardly facing surface 108 of the first baseplate 100, which hole 112 accepts a tail end of a post (described below) that has the ball at a head end of the post. Preferably, the tail end compression locks into the hole 112. As shown in FIGS. 3f–j, the convex structure 201 is integral with the second baseplate 200 and includes a curvate pocket 212 formed by a central portion 211 of the inwardly facing surface 208 of the convex structure 201 convexing inwardly and by a central portion of an outwardly facing surface 213 of the convex structure 201 concaving inwardly. The pocket 212 has a semispherical contour on the central portion of the outwardly facing surface 213 and an apex at the center of the semispherical contour. Further, the convex structure 201 has a bore 214 through the apex of the pocket 212, to accommodate the post. Further, the second baseplate 200 has on its outwardly facing surface 202 an access hole 209 surrounded by a circular recess 216 leading to the pocket 212, which recess 216 accepts the cap (described below) that serves as an extension of the second baseplate 200.

Referring now to FIGS. 3k–o, a first type 300 of the ball of the third embodiment family is shown in top (FIG. 3k), side (FIG. 3l), side cutaway (FIG. 3m), perspective cutaway (FIG. 3n) and perspective (FIG. 3o) views. The ball 300 is mounted at a head end 306 of a post 302 that also has a tail end 304. The ball 300 defines a spherical contour that is interrupted by the shaft of the post 302.

Referring now to FIGS. 3p–t, a first type 400 of the cap of the third embodiment family is shown in top (FIG. 3p), side (FIG. 3q), side cutaway (FIG. 3r), perspective cutaway (FIG. 3s) and perspective (FIG. 3t) views. The cap 400 includes an outwardly facing surface 402 that complements the outwardly facing surface 202 of the second baseplate 200 when the cap 400 is secured in the circular recess 216 of the second baseplate 200 (preferably, as shown, the outwardly facing surface 402 of the cap 400 provides the second baseplate 200 with the convex dome 203, as best shown in FIGS. 3u–y). The cap 400 further includes an inwardly facing surface 404, and a curvate pocket 406 formed by a central portion of the inwardly facing surface 404 of the cap 400 concaving outwardly. The pocket 406 has a semispherical contour that closely accommodates the spherical contour defined by the ball 300. The semispherical contour of the pocket 406 of the cap 400 opposes the semispherical contour of the pocket 212 of the convex structure 201 such that when the cap 400 is secured in the circular recess 216 of the second baseplate 200, the semispherical contours together define a socket 207 defining a spherical contour that closely accommodates the spherical contour defined by the ball 300 for free rotation and angulation of the ball 300 in the pockets 406,212. Each of the semispherical contour of the pocket 406 and the semispherical contour of the pocket 212 are preferably no greater than hemispherical, to make easier the assembly of the device.

Referring now to FIGS. 3u–y, an assembled first preferred embodiment of the third embodiment family is shown in top (FIG. 3u), side (FIG. 3v), side cutaway (FIG. 3w), perspective cutaway (FIG. 3x) and perspective (FIG. 3y) views. More particularly, assembly of the disc is preferably as follows. The tail end 304 of the post 302 is passed through the access hole 209 in the second baseplate 200 and through the bore 214 at the apex of the curvate pocket 212 of the convex structure 201, and the tail end 304 is thereafter secured to the central hole 112 in the first baseplate 100. (The access hole 209 has a diameter that accommodates the diameter of the ball 300 at the head 306 of the post 302, and the curvate pocket 212 on the outwardly facing surface 213 of the convex structure 201 has an opening diameter that accommodates the ball 300 for seating in the pocket 212 when the tail end 304 is fully passed through the bore 214. Thus, the ball 300 can be placed through the access hole 209 and into the curvate pocket during this step.) The bore 214 at the apex of the curvate pocket 212 has a diameter greater than the diameter of the post 302 but smaller than the diameter of the ball 300 at the head 306 of the post 302. Therefore, as the ball 300 is being placed into the curvate pocket 212, the post 302 fits through the bore 214, but the ball 300 does not, and the convex structure 201 (and the second baseplate 200) cannot be freed from the ball 300 once the tail end 304 of the post 302 is secured to the first baseplate 100. Although any suitable method is contemplated by the present invention, the attachment of the tail end 304 of the post 302 is preferably accomplished by compression locking (if accomplished alternatively or additionally by laser welding, the laser weld can, e.g., be applied from the outwardly facing surface 102 of the first baseplate 100 if the hole 112 passes completely through the first baseplate 100). The tail end 304 can also alternatively or additionally be threaded into the central hole 112 for increased stability of the attachment.

The semispherical contour of the pocket 212 closely accommodates the spherical contour defined by the ball 300, so that the ball 300 can freely rotate in the pocket 212 about the longitudinal axis of the post 302, and can freely angulate in the pocket 212 about a centroid of motion located at the center of the ball 300. Further, the bore 214 is tapered to a larger diameter toward the first baseplate 100, to permit the post 302 to angulate (about the centroid of motion at the center of the ball 300) with respect to the bore 214 as the ball 300 angulates in the pocket 212. Preferably, the conformation of the taper accommodates angulation of the post 302 at least until the perimeter regions 110,210 of the inwardly facing surfaces 108,208/211 meet.

Finally, the cap 400 is secured in the circular recess 216 of the second baseplate 200, so that the curvate pocket 406 of the cap 400 and the opposing curvate pocket 212 of the convex structure 201 together form the socket 207 defining the spherical contour within which the ball 300 at the head 306 of the post 302 freely rotates and angulates as described above. The application of the cap 400 also seals the access hole 209 in the second baseplate (or, if the cap 400 has a bore, it preferably reduces the diameter of the access hole 209 to a size that does not accommodate the diameter of the ball 300). Although any suitable method is contemplated by the present invention, the cap 400 preferably is secured in the circular recess 216 by compression locking (a laser weld can alternatively or additionally be used, or other suitable attachment means). As stated above, the cap 400 preferably has an outwardly facing surface 402 that complements the outwardly facing surface 202 of the second baseplate 200 for surface uniformity once the cap 400 is secured. The cap 400 may also additionally or alternatively be threaded into the circular recess 216 for increased stability of the attachment.

Accordingly, when the device of the first preferred embodiment of the third embodiment family is assembled, the baseplates are rotatable relative to one another because the ball 300 rotates freely within the socket 207, and angulatable relative to one another because the ball 300 angulates freely within the socket 207. Because the ball 300 is held within the socket 207 by the securing of the tail end 304 of the post 302 to the first baseplate 100 and the securing of the cap 400 to the second baseplate 200, the artificial disc can withstand tension loading of the baseplates 100,200. More particularly, when a tension load is applied to the baseplates 100,200 the ball 300 seeks to pass through the bore 214 at the apex of the curvate pocket 212. However, the smaller diameter of the bore 214 relative to the diameter of the ball 300 prevents the ball 300 from exiting the socket 207. Therefore, the assembly does not come apart under normally experienced tension loads. This ensures that no individual parts of the assembly will pop out or slip out from between the vertebral bodies when, e.g., the patient stretches or hangs while exercising or performing other activities. Thus, in combination with the securing of the baseplates 100,200 to the adjacent vertebral bones via the domes 103,203 and spikes 105,205, the disc assembly has an integrity similar to the tension-bearing integrity of a healthy natural intervertebral disc. Also because the ball 300 is laterally captured in the socket 207, lateral translation of the baseplates 100,200 relative to one another is prevented during rotation and angulation, similar to the performance of healthy natural intervertebral disc. Because the baseplates 100,200 are made angulatable relative to one another by the ball 300 being rotatably and angulatably coupled in the socket 207, the disc assembly provides a centroid of motion within the ball 300. Accordingly, the centroid of motion of the disc assembly remains centrally located between the vertebral bodies, similar to the centroid of motion in a healthy natural intervertebral disc.

The remaining embodiments in the third embodiment family of the present invention limit the rotation (but preferably not the angulation) of the ball in the socket defined by the pocket of the convex structure and the pocket of the cap. Each embodiment accomplishes this in a different manner, but each embodiment utilizes interference between a protrusion and a recess to limit the rotation. In some embodiments, the protrusion is preferably hemispherical, and the recess preferably has a semicylindrical contour within which the protrusion fits. In other embodiments, the protrusion is preferably hemispherical, and the recess preferably has a curvate contour that is not semicylindrical. (It should be understood that the described formations of the recess and the protrusion are merely preferred, and that alternate formations, curvate or otherwise, for each are contemplated by the present invention; a particular shape or location of recess or a particular shape or location of protrusion is not required; any shape can be used so long as the recess and protrusion interact as desired. For example, the recess in the second preferred embodiment of the third embodiment family has a curvate contour that is not semicylindrical so that it optimally interacts with the protrusion in that embodiment.) The boundaries of the recess define the limits of rotation of the ball within the socket, by allowing movement of the protrusion relative to the recess as the ball rotates through a certain range in the socket, but providing interference with the protrusion to prevent rotation of the ball beyond that range in the socket. Preferably, for example, the recess has a depth equivalent to the radius of the protrusion, but a radius of curvature greater than that of the protrusion. At the same time, the boundaries of the recess preferably do not limit the angulation of the ball within the socket, at least until the perimeter regions of the inwardly facing surfaces meet. Preferably for example, the recess has a length greater than the range of movement of the protrusion relative to the recess as the ball angulates in the socket.

Therefore, when assembled, the discs of the remaining preferred embodiments of the third embodiment family enable angulation and limited rotation of the baseplates relative to one another about a centroid of motion that remains centrally located between the baseplates (at the center of the sphere defined by the ball), similar to the centroid of motion in a healthy natural intervertebral disc that is limited in its rotation by surrounding body structures. A benefit of limiting the relative rotation of the baseplates is that relative rotation beyond a certain range in a healthy natural disc is neither needed nor desired, because, for example, excess strain can be placed on the facet joints or ligaments thereby. As described with the first preferred embodiment of the third embodiment family, the construction also prevents translation and separation of the baseplates relative to one another during rotation and angulation.

As noted above, each of the remaining preferred embodiments in this third embodiment family forms the protrusion and corresponding recess in a different manner, utilizing components that are either identical or similar to the components of the first preferred embodiment, and some embodiments utilize additional components. Each of the remaining preferred embodiments will now be described in greater detail.

In the second preferred embodiment of the third embodiment family of the present invention, a hemispherical protrusion is formed on the ball itself, and interacts in the above-described manner with a curvate recess formed adjacent the socket defined by the pocket of the convex structure and the pocket of the cap. More particularly, this second preferred embodiment uses the same first baseplate 100 as the first preferred embodiment of the third embodiment family described above. Referring to FIGS. 4a–e, a second type 500 of second baseplate of the third embodiment family is shown in top (FIG. 4a), side (FIG. 4b), side cutaway (FIG. 4c), perspective cutaway (FIG. 4d) and perspective (FIG. 4e) views. This second type 500 of second baseplate is identical to the first type 200 of second baseplate described above (and thus similar features are reference numbered similar to those of the first type 200 of second baseplate, but in the 500s rather than the 200s), except that this second type 500 of second baseplate has a curvate recess 518 adjacent the curvate pocket 512 in the convex structure 501.

As shown in FIGS. 4a to 4e, the convex structure 501 is integral with the second baseplate 500 and includes a curvate pocket 512 formed by a central portion 511 of the inwardly-facing surface 508 of the convex structure 501 convexing inwardly and by a central portion of an outwardly-facing surface 513 of the convex structure 501 concaving inwardly. The pocket 512 has a semispherical contour on the central portion of the outwardly-facing surface 513 and an apex at the center of the semispherical contour. Further, the convex structure 501 has a bore 514 through the apex of the pocket 512, to accommodate the post. Further, the second baseplate 500 has an outwardly-facing surface 502 and an access hole 509 surrounded by a circular recess 516 leading to the pocket 512, which recess 216 accepts the cap that serves as an extension of the baseplate. The convex structure 501 also includes a perimeter region 510 extending about the inwardly-facing surface 508. A plurality of spikes 505 may also be included on the outwardly-facing surface 502 of baseplate 500.

Referring now to FIGS. 4f–j, a second type 600 of ball of the third embodiment family is shown in top (FIG. 4f), side (FIG. 4g), side cutaway (FIG. 4h), perspective cutaway (FIG. 4i) and perspective (FIG. 4j) views. The ball 600 is identical to the first type 300 of ball described above (and thus similar features are reference numbered similar to those of the first type 300 of ball, but in the 600s rather than the 300s), except that the spherical contour defined by this second type 600 of ball is also interrupted by a hemispherical protrusion 608. Thus, ball 600 includes a post 602 having a tail end 604 disposed at one end and a head 606 disposed opposite the tail end.

Referring now to FIGS. 4k–o, a second type 700 of cap of the third embodiment family is shown in top (FIG. 4k), side (FIG. 4l), side cutaway (FIG. 4m), perspective cutaway (FIG. 4n) and perspective (FIG. 4o) views. This second type 700 of cap is identical to the first type 400 of cap described above (and thus similar features are reference numbered similar to those of the first type 400 of cap, but in the 700s rather than the 400s), except that this second type 700 of cap has a curvate recess 708 adjacent the curvate pocket 706. Cap 700, similar to cap 400, also includes an outwardly-facing surface 702 and an inwardly-facing surface 704. As with regard to cap 400, outwardly-facing surface 702 compliments the outwardly-facing surface 502 of baseplate 500 to provide surface uniformity once the cap 700 is secured.

Referring now to FIGS. 4p–t, an assembled second preferred embodiment of the third embodiment family is shown in top (FIG. 4p), side (FIG. 4q), side cutaway (FIG. 4r), perspective cutaway (FIG. 4s) and perspective (FIG. 4t) views. It can be seen that the curvate recesses 518,708 together form the recess described above in the discussion of the manner in which these remaining embodiments limit rotation of the ball in the socket, and that the protrusion 608 serves as the protrusion described above in the same discussion. Thus, the protrusion 608 and recesses 518,708 interact in the above described manner to limit the rotation of the ball 600 in the socket 507 defined by the curvate pockets 512,706. Assembly of the disc is identical to that of the first preferred embodiment of the third embodiment family, except that the protrusion 608 is longitudinally aligned with the recess 518, and the recess 708 is similarly aligned, so that when the cap 700 is secured to the second baseplate 500, the protrusion 608 is fitted within the recesses 518,708 for interaction as described above as the ball 600 rotates and angulates in the socket 507.

In the third preferred embodiment of the third embodiment family of the present invention, a hemispherical protrusion is formed to protrude into the socket defined by the pocket of the convex structure and the pocket of the cap, and interacts in the above-described manner with a semicylindrical recess formed on the ball. More particularly, this third preferred embodiment uses the same first baseplate 100 and the same cap 400 as the first preferred embodiment of the third embodiment family. Referring to FIGS. 5a–e, a third type 800 of second baseplate of the third embodiment family is shown in top (FIG. 5a), side (FIG. 5b), side cutaway (FIG. 5c), perspective cutaway (FIG. 5d) and perspective (FIG. 5e) views. This third type 800 of second baseplate is identical to the first type 200 of second baseplate described above (and thus similar features are reference numbered similar to those of the first type 200 of second baseplate, but in the 800s rather than the 200s), except that this third type 800 of second baseplate has a protrusion 818 jutting out from the wall of the pocket 812 in the convex structure 801.

As shown in FIGS. 5a to 5e, the convex structure 801 is integral with the second baseplate 800 and includes a curvate pocket 812 formed by a central portion 811 of the inwardly-facing surface 808 of the convex structure 801 convexing inwardly and by a central portion of an outwardly-facing surface 813 of the convex structure 801 concurving inwardly. The inwardly-facing surface 808 also includes a perimeter region 810. The pocket 812 has a semispherical contour on the central portion on the outwardly-facing surface 813 and an apex at the center of the semispherical contour. Further, the convex structure 801 has a bore 814 extending through the apex of the pocket 812, to accommodate the post. Further, baseplate 800 has an outwardly-facing surface 802 and an access hole 809 surrounded by a circular recess 816 leading to the pocket 812, which recess 816 accepts the cap (described below) that serves as an extension of the baseplate 800. The baseplate

800 preferably also includes a plurality of spikes 805 disposed along the outwardly-facing surface 802. As shown in FIG. 5*n*, cap 400 can be secured to the circular recess 816 and provide a convex dome 803 to baseplate 800.

Referring now to FIGS. 5*f–j*, a third type 900 of ball of the third embodiment family is shown in top (FIG. 5*f*), side (FIG. 5*g*), side cutaway (FIG. 5*h*), perspective cutaway (FIG. 5*i*) and perspective (FIG. 5*j*) views. The ball 900 is identical to the first type 300 of ball described above (and thus similar features are reference numbered similar to those of the first type 300 of ball, but in the 900s rather than the 300s), except that the spherical contour of this third type 900 of ball is also interrupted by a curvate recess 908. As with previous embodiments ball 900 includes a post 902 having a tail end 904 and a head end 906.

Referring now to FIGS. 5*k–o*, an assembled third preferred embodiment of the third embodiment family is shown in top (FIG. 5*k*), side (FIG. 5*l*), side cutaway (FIG. 5*m*), perspective cutaway (FIG. 5*n*) and perspective (FIG. 5*o*) views. It can be seen that the curvate recess 908 forms the recess described above in the discussion of the manner in which these remaining embodiments limit rotation of the ball in the socket, and that the protrusion 818 serves as the protrusion described above in the same discussion. Thus, the protrusion 818 and recess 908 interact in the above described manner to limit the rotation of the ball 900 in the socket 807 defined by the curvate pockets 812,406. Assembly of the disc is identical to that of the first preferred embodiment of the third embodiment family, except that the protrusion 818 is longitudinally aligned with the recess 908 during assembly so that the protrusion 818 is fitted within the recess 908 for interaction as described above as the ball 900 rotates and angulates in the socket 807.

In the fourth preferred embodiment of the third embodiment family of the present invention, a pin is secured in a pin hole so that the hemispherical head of the pin protrudes into the socket defined by the pocket of the convex structure and the pocket of the cap, and interacts in the above-described manner with a semicylindrical recess formed on the ball. More particularly, this fourth preferred embodiment uses the same first baseplate 100 and cap 400 of the first preferred embodiment, and the same ball 900 of the third preferred embodiment, but utilizes a fourth type of second baseplate of the third embodiment family. Referring to FIGS. 6*a–e*, the fourth type 1000 of second baseplate is shown in top (FIG. 6*a*), side (FIG. 6*b*), side cutaway (FIG. 6*c*), perspective cutaway (FIG. 6*d*) and perspective (FIG. 6*e*) views. This fourth type 1000 of second baseplate is identical to the first type 200 of second baseplate described above (and thus similar features are reference numbered similar to those of the first type 200 of second baseplate, but in the 1000s rather than the 200s), except that this fourth type 1000 of second baseplate has a lateral through hole (e.g., a pin hole 1020) and a protrusion (e.g., a pin 1018) secured in the pin hole 1020 (as shown in FIGS. 6*f–j*) with the hemispherical head of the pin 1018 jutting out from the wall of the pocket 1012 toward the center of the pocket 1012 in the convex structure 1001.

As shown in FIGS. 6*a* to 6*e*, second baseplate 1000 similar to second baseplate 200, includes convex structure 1001 integral with second baseplate 1000 and includes a curvate pocket 1012 formed by a central portion 1011 of the inwardly-facing surface 1008 of the convex structure 1001 convexing inwardly and by a central portion of an outwardly-facing surface 1013 of the convex structure 1001 concaving inwardly. The inwardly-facing surface 1008 also includes a perimeter region 1010 extending about the inwardly-facing surface. The pocket 1012 has a semispherical contour on the central portion of the outwardly-facing surface 1013 and an apex at the center of the semispherical contour. Further, the convex structure 1001 has a bore 1014 extending through the apex of the pocket 1012 to accommodate the post. Further, the second baseplate 1000 has on its outwardly-facing surface 1002 an access hole 1009 surrounded by a circular recess 1016 leading to the pocket 1012, which recess 1016 accepts the cap as previously described in conjunction with previous embodiments. In one preferred embodiment, the second baseplate 1000 includes a plurality of spikes 1005 disposed along its outwardly-facing surface 1002. As best seen in FIG. 6*i*, cap 400 may be secured in the circular recess 1016 of the baseplate 1000 and preferably includes a convex dome 1003 similar to convex dome 203.

Referring now to FIGS. 6*f–j*, an assembled fourth preferred embodiment of the third embodiment family is shown in top (FIG. 6*f*), side (FIG. 6*g*), side cutaway (FIG. 6*h*), perspective cutaway (FIG. 6*i*) and perspective (FIG. 6*j*) views. It can be seen that the curvate recess 908 of the ball 900 forms the recess described above in the discussion of the manner in which these remaining embodiments limit rotation of the ball in the socket, and that the head of the pin 1018 serves as the protrusion described above in the same discussion. Thus, the head of the pin 1018 and the recess 908 interact in the above described manner to limit the rotation of the ball 900 in the socket 1007 defined by the curvate pockets 1012,406. Assembly of the disc is identical to that of the first preferred embodiment of the third embodiment family, except that the head of the pin 1018 is longitudinally aligned with the recess 908 during assembly so that the head of the pin 1018 is fitted within the recess 908 for interaction as described above as the ball 900 rotates and angulates in the socket 1007.

In the fifth preferred embodiment of the third embodiment family of the present invention, a ball bearing protrudes into the socket defined by the pocket of the convex structure and the pocket of the cap, and interacts in the above-described manner with a semicylindrical recess formed on the ball. More particularly, this fifth preferred embodiment uses the same first baseplate 100 and cap 400 of the first preferred embodiment, and the same ball 900 of the third preferred embodiment, but utilizes a fifth type of second baseplate of the third embodiment family. Referring to FIGS. 7*a–e*, the fifth type 1200 of second baseplate is shown in top (FIG. 7*a*), side (FIG. 7*b*), side cutaway (FIG. 7*c*), perspective cutaway (FIG. 7*d*) and perspective (FIG. 7*e*) views. This fifth type 1200 of second baseplate is identical to the first type 200 of second baseplate described above (and thus similar features are reference numbered similar to those of the first type 200 of second baseplate, but in the 1200s rather than the 200s), except that this fifth type 1200 of second baseplate has a recess 1218 adjacent the curvate pocket 1212 in the convex structure 1201, the recess 1218 preferably being semicylindrical as shown.

As shown in FIGS. 7*a* to 7*e*, second baseplate 1200 is similarly designed to baseplate 200 and includes a convex structure 1201 integral with the second baseplate 1200 and includes a curvate pocket 1212 formed by a central portion 1211 of the inwardly-facing surface 1208 of the convex structure 1201 convexing inwardly and by a central portion of an outwardly-facing surface 1213 of convex structure 1201 concaving inwardly. The inwardly-facing surface 1208 preferably includes a perimeter region 1210 extending about its surface. The pocket 1212 has a semispherical contour of the central portion of the outwardly-facing surface 1213 and an apex at the center of the semispherical contour. Further, the convex structure 1201 has a bore 1214 through the apex of the pocket 1212, to accommodate the post. Further, the second baseplate 1200 has on its outwardly-facing surface 1202 an access hole 1209 surrounded by a circular recess 1216 leading to the pocket 1212, which recess 1216 accepts the cap 400. As best seen in FIG. 7*i*, cap 400 when received within recess 1216 provides a convex dome 1203 to the second baseplate, as described with reference to second baseplate 200. In one preferred embodiment, baseplate 1200 includes a plurality of spikes 1205 extending from outwardly-facing surface 1202.

Referring now to FIGS. 7*f–j*, an assembled fifth preferred embodiment of the third embodiment family is shown in top (FIG. 7*f*), side (FIG. 7*g*), side cutaway (FIG. 7*h*), perspective cutaway (FIG. 7*i*) and perspective (FIG. 7*j*) views. A ball bearing 1300 of the third embodiment family is captured for free rotation and angulation with one part closely accommodated in the semicylindrical recess 1218 and one part protruding into the curvate pocket 1212 to interact with the curvate recess 908 of the ball 900. It can be seen that the curvate recess 908 of the ball 900 forms the recess described above in the discussion of the manner in which these remaining embodiments limit rotation of the ball in the socket, and that the ball bearing 1300 serves as the protrusion described above in the same discussion. Thus, the ball bearing 1300 and the recess 908 interact in the above described manner to limit the rotation of the ball 900 in the socket 1207 defined by the curvate pockets 1212,406. Assembly of the disc is identical to that of the first preferred embodiment of the third embodiment family, except that the semicylindrical recess 1218 is longitudinally aligned with the curvate recess 908 during assembly so that the ball bearing 1300 can be and is then placed into the recesses 1218,908 for interaction as described above as the ball 900 rotates and angulates in the socket 1207.

Embodiments of the fourth embodiment family of the present invention will now be described.

With regard to the configuration of the convex structure in the fourth embodiment family, the convex structure is configured as a non-flexible element that has the socket of the ball and socket joint at its peak. In the preferred embodiment, the convex structure is shaped to have a curved taper, similar to the configuration of the convex structure in the third embodiment family. The convex structure in the fourth embodiment family is separated from the second baseplate during assembly of the device, for reasons related to the manner in which the ball is captured in the socket, but is attached to the second baseplate by the time assembly is complete.

With regard to the manner in which the ball is captured in the socket in the fourth embodiment family, the capturing is effected through the use of a solid ball. In order to permit the seating of the ball into the socket formed at the peak of the convex structure, the convex structure is a separate element from the second baseplate. The ball is first seated against the central portion of the second baseplate (which central portion preferably has a concavity that has a curvature that closely accommodates the contour of the ball), and then the convex structure is placed over the ball to seat the ball in the socket formed in the interior of the peak of the convex structure (the interior is preferably formed as a concavity that is either hemispherical or less-than-hemispherical so that the ball can easily fit into it). After the convex structure is placed over the ball, the convex structure is attached to the second baseplate to secure the ball in the socket. As in the third embodiment family, the peak of the convex structure has a bore that accommodates a post to which the ball and the first baseplate are attached (one to each end of the post), but does not accommodate the ball for passage through the bore. Accordingly, the ball is maintained in the socket.

A first preferred embodiment of a fourth embodiment family of the present invention will now be described.

Referring to FIGS. 8*a–e*, a first baseplate 1400 of a fourth embodiment family of the present invention is shown in top (FIG. 8*a*), side (FIG. 8*b*), side cutaway (FIG. 8*c*), perspective cutaway (FIG. 8*d*) and perspective (FIG. 8*e*) views. Also referring to FIGS. 8*f–j*, a first type 1500 of a second baseplate of the fourth embodiment family is shown in top (FIG. 8*f*), side (FIG. 8*g*), side cutaway (FIG. 8*h*), perspective cutaway (FIG. 8*i*) and perspective (FIG. 8*j*) views.

More specifically, the first and second baseplates 1400, 1500 are similar to the first and second baseplates of the third embodiment family described above with regard to their outwardly facing surfaces 1402,1502 having a convex dome 1403,1503 and a plurality of spikes 1405,1505 as vertebral body contact elements, and the inwardly facing surface 1408 of the first baseplate having a perimeter region 1410, all of which elements in the fourth embodiment family are, for example, identical to the corresponding elements in the third embodiment family as described above. Preferably, the dome 1403,1503 is covered with an osteoconductive layer of a type known in the art. It should be noted that the convex mesh used in other embodiments of the present invention is suitable for use with these other vertebral body contact elements, and can be attached over the convex dome 1403,1503 by laser welding, or more preferably, by plasma burying (where the perimeter region of the convex mesh is buried under a plasma coating, which coating secures to the outwardly facing surface of the baseplate to which it is applied, and thus secures the convex mesh to the outwardly facing surface).

Further, as with the first embodiment family, the two baseplates 1400,1500 are joined with a ball and socket joint, and therefore each of the baseplates 1400,1500 comprises features that, in conjunction with other components described below, form the ball and socket joint. The ball and socket joint includes a solid ball (described below) mounted to protrude from the inwardly facing surface 1408 of the first baseplate 1400, and a curvate socket formed at a peak of a non-flexible convex structure (described below) that is attached to the inwardly facing surface 1508 of the second baseplate 1500, within which curvate socket the ball is capturable for free rotation and angulation therein. As shown in FIGS. 8*a–d*, the mounting for the ball includes a central inwardly directed post 1412 that extends from the inwardly facing surface 1408 of the first baseplate 1400, which post's head end compression locks into a central bore in the ball (described below). As shown in FIGS. 8*e–h*, the second baseplate 1500 includes an inwardly facing surface 1508 and a curvate pocket 1512 formed by a central portion of the inwardly facing surface 1508 concaving outwardly with a semispherical contour (preferably a hemispherical contour). Preferably, as shown, the curvate pocket 1512 is surrounded by a circumferential wall 1514 and a circumferential recess 1516 that cooperate with the convex structure to attach the convex structure to the second baseplate 1500.

Referring now to FIGS. 8*k–o*, a first type 1600 of a ball of the fourth embodiment family is shown in top (FIG. 8*k*), side (FIG. 8*l*), side cutaway (FIG. 8*m*), perspective cutaway (FIG. 8*n*) and perspective (FIG. 8*o*) views. The ball 1600 is semispherical (preferably greater than hemispherical as shown) and therefore defines a spherical contour, and has a central bore 1602 within which the first baseplate's post's head end is securable. The ball 1600 seats in the curvate pocket 1512 of the second baseplate 1500 with the spherical contour defined by the ball 1600 closely accommodated by the hemispherical contour of the curvate pocket 1512 for free rotation and free angulation of the ball 1600 in the curvate pocket 1512.

Referring now to FIGS. 8*p–t*, a first type 1700 of a convex structure of the fourth embodiment family is shown in top (FIG. 8*p*), side, (FIG. 8*q*), side cutaway (FIG. 8*r*), perspective cutaway (FIG. 8*s*) and perspective (FIG. 8*t*) views. The convex structure 1700 is shaped to have a curved taper on its inwardly facing surface 1706 (as opposed to the frustoconical shape of the convex structure in the first and second embodiment families) and includes a central bore 1702 extending from an outwardly facing surface 1704 of the convex structure 1700 to an inwardly facing surface 1706 of the convex structure 1700, the bore 1702 being surrounded by a curvate taper 1708 on the outwardly facing surface 1704, and the curvate taper 1708 being surrounded by a circumferential recess 1710 and a circumferential wall 1712. The convex structure 1700 is securable to the second baseplate 1500 with the circumferential recess 1710 of the convex structure 1700 mating with the circumferential wall 1514 of the second baseplate 1500 and the circumferential wall 1712 of the convex structure 1700 mating with the circumferential recess 1516 of the second baseplate 1500, so that when the convex structure 1700 is so secured, the curvate taper 1708 of the convex structure 1700 serves as a curvate pocket opposite the curvate pocket 1512 of the second baseplate 1500. That is, the curvate taper 1708 complements the hemispherical contour of the curvate pocket 1512 of the second baseplate 1500 to form a semispherical (and preferably greater than hemispherical as shown) socket 1707 defining a spherical contour that closely accommodates the spherical contour defined by the ball 1600 so that the ball 1600 is captured in the socket 1707 for free rotation and free angulation of the ball 1600 therein. (When the formed socket 1707 is greater than hemispherical, and the shape of the ball 1600 is greater than hemispherical, the ball 1600 cannot escape the formed socket 1707.) Further, the inwardly facing surface 1706 of the convex structure 1700 has a perimeter region 1714 that faces the perimeter region 1410 of the first baseplate 1400 when the convex structure 1700 is secured to the second baseplate 1500.

Referring now to FIGS. 8*u–y*, an assembled first preferred embodiment of the fourth embodiment family is shown in top (FIG. 8*u*), side (FIG. 8*v*), side cutaway (FIG. 8*w*), perspective cutaway (FIG. 8*x*) and perspective (FIG. 8*y*) views. More particularly, assembly of the disc is preferably as follows. The ball 1600 is seated within the curvate pocket 1512 of the second baseplate 1500 (the curvate pocket 1512 has an opening diameter that accommodates the ball 1600) so that the spherical contour defined by the ball 1600 is closely accommodated by the hemispherical contour of the curvate pocket 1512. Thereafter, the convex structure 1700 is secured to the second baseplate 1500 as described above with the convex structure's curvate pocket 1708 (the curvate tapered lip 1708 of the convex structure's central bore 1702) fitting against the ball 1600 so that the ball 1600 is captured in the socket 1707 (formed by the curvate taper 1708 and the curvate pocket 1512) for free rotation and free angulation of the ball 1600 therein. Thereafter, the first baseplate's post's head end is secured into the bore 1602 of the ball 1600. The central bore 1702 of the convex structure 1700 has a diameter that accommodates the diameter of the post 1412, but not the diameter of the ball 1600. Therefore, after the ball 1600 is secured in the socket 1707, the post 1412 fits through the bore 1702 so that the head end of the post 1412 can be compression locked to the ball 1600, but the ball 1600 is prevented from escaping the socket 1707 through the central bore 1702 of the convex structure 1700.

Accordingly, the ball 1600 is captured in the socket 1707 (so that the device will not separate in tension), can freely rotate in the socket 1707 about the longitudinal axis of the post 1412, and can freely angulate in the socket 1707 about a centroid of motion located at the center of the sphere defined by the ball 1600. Further, the opening of the bore 1702 of the cap 1700 on the inwardly facing surface 1706 of the convex structure 1700 is large enough to permit the post 1412 to angulate (about the centroid of motion at the center of the sphere defined by the ball 1600) with respect to the bore 1702 as the ball 1600 angulates in the socket 1707. Preferably, the conformation of the bore 1702 accommodates angulation of the post 1412 at least until the perimeter regions 1410,1714 of the inwardly facing surfaces 1408, 1508/1706 meet. Further preferably, the perimeter regions 1410,1714 have corresponding contours, so that the meeting of the perimeter regions reduces any surface wearing.

Accordingly, when the device of the first preferred embodiment of the fourth embodiment family is assembled, the baseplates 1400,1500 are rotatable relative to one another because the ball 1600 rotates freely within the socket 1707, and angulatable relative to one another because the ball 1600 angulates freely within the socket 1707. Because the ball 1600 is held within the socket 1707 by the securing of the tail end of the central post 1412 of the first baseplate 1400 to the ball 1600 and the securing of the convex structure 1700 to the second baseplate 1500, the artificial disc can withstand tension loading of the baseplates 1400,1500. More particularly, when a tension load is applied to the baseplates 1400,1500 the ball 1600 seeks to pass through the bore 1702 in the convex structure 1700. However, the curvate taper 1708 of the bore 1702 prevents the ball 1600 from exiting the socket 1707. Therefore, the assembly does not come apart under normally experienced tension loads. This ensures that no individual parts of the assembly will pop out or slip out from between the vertebral bodies when, e.g., the patient stretches or hangs while exercising or performing other activities. Thus, in combination with the securing of the baseplates 1400,1500 to the adjacent vertebral bones via the domes 1403,1503 and spikes 1405,1505, the disc assembly has an integrity similar to the tension-bearing integrity of a healthy natural intervertebral disc. Also, because the ball 1600 is laterally captured in the socket 1707, lateral translation of the baseplates 1400,1500 relative to one another is prevented during rotation and angulation, similar to the performance of healthy natural intervertebral disc. Because the baseplates 1400,1500 are made angulatable relative to one another by the ball 1600 being rotatably and angulatably coupled in the socket 1707, the disc assembly provides a centroid of motion within the sphere defined by the ball 1600. Accordingly, the centroid of motion of the disc assembly remains centrally located between the vertebral bodies, similar to the centroid of motion in a healthy natural intervertebral disc.

The remaining embodiments in the fourth embodiment family of the present invention limit the rotation (but preferably not the angulation) of the ball in the socket formed by the curvate taper of the convex structure and the hemispherical contour of the curvate pocket of the second baseplate. Each embodiment accomplishes this in a different manner, but each embodiment utilizes interference between a protrusion and a recess to limit the rotation, similar to the manner in which such interference is utilized in the third embodiment family. In some embodiments, the protrusion is preferably hemispherical, and the recess preferably has a semicylindrical contour within which the protrusion fits. In other embodiments, the protrusion is preferably hemispherical, and the recess preferably has a curvate contour that is not semicylindrical. (It should be understood that the described formations of the recess and the protrusion are merely preferred, and that alternate formations, curvate or otherwise, for each are contemplated by the present invention; a particular shape or location of recess or a particular shape or location of protrusion is not required; any shape can be used so long as the recess and protrusion interact as desired. For example, the recess in the second preferred embodiment of the fourth embodiment family has a curvate contour that is not semicylindrical, and the recess in the fifth preferred embodiment of the fourth embodiment family has a different curvate contour that is not semicylindrical, each being formed so that it optimally interacts with the protrusion in its respective embodiment.) The boundaries of the recess define the limits of rotation of the ball within the socket, by allowing movement of the protrusion relative to the recess as the ball rotates through a certain range in the socket, but providing interference with the protrusion to prevent rotation of the ball beyond that range in the socket. Preferably, for example, the recess has a depth equivalent to the radius of the hemispherical protrusion, but a radius of curvature greater than that of the protrusion. At the same time, the boundaries of the recess preferably do not limit the angulation of the ball within the socket, at least until the perimeter regions of the inwardly facing surface of the convex structure and the inwardly facing surface of the first baseplate meet. Preferably, for example, the recess has a length greater than the range of movement of the protrusion relative to the recess as the ball angulates in the socket.

Therefore, when assembled, the discs of the remaining preferred embodiments of the fourth embodiment family enable angulation and limited rotation of the baseplates relative to one another about a centroid of motion that remains centrally located between the baseplates (at the center of the sphere defined by the ball), similar to the centroid of motion in a healthy natural intervertebral disc that is limited in its rotation by surrounding body structures. A benefit of limiting the relative rotation of the baseplates is that relative rotation beyond a certain range in a healthy natural disc is neither needed nor desired, because, for example, excess strain can be placed on the facet joints or ligaments thereby. As described with the first preferred embodiment of the fourth embodiment family, the construction also prevents translation and separation of the baseplates relative to one another during rotation and angulation.

As noted above, each of the remaining preferred embodiments in this fourth embodiment family forms the protrusion and corresponding recess in a different manner, utilizing components that are either identical or similar to the components of the first preferred embodiment, and some embodiments utilize additional components. Each of the remaining preferred embodiments will now be described in greater detail.

In the second preferred embodiment of the fourth embodiment family of the present invention, a hemispherical protrusion is formed on the ball, and interacts in the above-described manner with a recess formed adjacent the socket formed by the curvate taper of the convex structure and the hemispherical contour of the curvate pocket of the second baseplate. More particularly, this second preferred embodiment uses the same first baseplate 1400 as the first preferred embodiment of the fourth embodiment family described above. Referring to FIGS. 9a–e, a second type 1800 of second baseplate of the fourth embodiment family is shown in to top (FIG. 9a), side (FIG. 9b), side cutaway (FIG. 9c), perspective cutaway (FIG. 9d) and perspective (FIG. 9e) views. This second type 1800 of second baseplate is identical to the first type 1500 of second baseplate described above (and thus similar features are reference numbered similar to those of the first type 1500 of second baseplate, but in the 1800s rather than the 1500s), except that this second type 1800 of second baseplate has a curvate recess 1818 adjacent the curvate pocket 1812, and preferably in the circumferential wall 1814.

As shown in FIGS. 9a to 9e, second baseplate 1800 is similarly constructed to second base 1500 and includes an outwardly-facing surface 1802 having a convex dome 1803 and a plurality of spikes 1805. The convex dome 1803 may have similar attributes and be attached to second baseplate 1800 similarly to convex dome 1503. Second baseplate 1800 also includes an inwardly-facing surface 1808 and a curvate pocket 1812 formed by a central portion of the inwardly-facing surface 1808 concaving outwardly with a semispherical contour. Preferably, as shown, the curvate pocket 1812 is surrounded by a circumferential wall 1814 and a circumferential recess 1816 which are similar to circumferential wall 1512 and circumferential recess 1516. Further, the second baseplate 1200 includes an access hole 1809.

Referring now to FIGS. 9f–j, a second type 1900 of ball of the fourth embodiment family is shown in top (FIG. 9f), side (FIG. 9g), side cutaway (FIG. 9h), perspective cutaway (FIG. 9i) and perspective (FIG. 9j) views. The ball 1900 is identical to the first type 1600 of ball described above and includes central bore 1902 (and thus similar features are reference numbered similar to those of the first type 1600 of ball, but in the 1900s rather than the 1600s), except that the semispherical contour of this second type 1900 of ball is also interrupted by a hemispherical protrusion 1904.

Referring now to FIGS. 9k–o, a second type 2000 of convex structure of the fourth embodiment family is shown in top (FIG. 9k), side (FIG. 9l), side cutaway (FIG. 9m), perspective cutaway (FIG. 9n) and perspective (FIG. 9o) views. This second type 2000 of convex structure is identical to the first type 1700 of convex structure described above (and thus similar features are reference numbered similar to those of the first type 1700 of convex structure, but in the 2000s rather than the 1700s), except that this second type 2000 of convex structure has a curvate recess 2016 adjacent the curvate taper 2008.

As shown in the FIGS. 9k to 9o, convex structure 2000 is designed similarly as convex structure 1700. Convex structure 2000 is shaped to have a curved taper on its inwardly-facing surface 2006 and includes a central bore 2002 extending from an outwardly-facing surface 2004 of the convex structure 2000 to an inwardly-facing surface 2006 of the convex structure 2000. The bore 2002 is surrounded by a curvet taper 2008 on the outwardly-facing surface 2004 with the curvet taper 2008 being surrounded by a circumferential recess 2010 and a circumferential wall 2012. The convex structure 2000 also includes a perimeter region 2014 extending radially around the structure.

Referring now to FIGS. 9p–t, an assembled second preferred embodiment of the fourth embodiment family is shown in top (FIG. 9p), side (FIG. 9q), side cutaway (FIG. 9r), perspective cutaway (FIG. 9s) and perspective (FIG. 9t) views. It can be seen that the curvate recesses 1818,2016 together form the recess described above in the discussion of the manner in which these remaining embodiments limit rotation of the ball in the socket formed by the curvate taper of the convex structure and the hemispherical contour of the curvate pocket of the second baseplate, and that the protrusion 1904 serves as the protrusion described above in the same discussion. Thus, the protrusion 1904 and recesses 1818,2016 interact in the above described manner to limit the rotation of the ball 1900 in the socket 2007. Assembly of the disc is identical to that of the first preferred embodiment of the fourth embodiment family, except that the protrusion 1904 is longitudinally aligned with the recess 1818, and the recess 2016 is similarly aligned, so that when the convex structure 2000 is secured to the second baseplate 1800, the protrusion 1904 is fitted within the recesses 1818,2016 for interaction as described above as the ball 1900 rotates and angulates in the socket 2007.

In the third preferred embodiment of the fourth embodiment family of the present invention, a hemispherical protrusion is formed to protrude into the socket formed by the curvate taper of the convex structure and the hemispherical contour of the curvate pocket of the second baseplate, and interacts in the above-described manner with a semicylindrical recess formed on the ball. More particularly, this third preferred embodiment uses the same first baseplate 1400 as the first preferred embodiment of the fourth embodiment family described above. Referring to FIGS. 10*a–e*, a third type 2100 of second baseplate of the fourth embodiment family is shown in top (FIG. 10*a*), side (FIG. 10*b*), side cutaway (FIG. 10*c*), perspective cutaway (FIG. 10*d*) and perspective (FIG. 10*e*) views. This third type 2100 of second baseplate is identical to the first type 1500 of second baseplate described above (and thus similar features are reference numbered similar to those of the first type 1500 of second baseplate, but in the 2100s rather than the 1500s), except that this third type 2100 of second baseplate has a recess 2118 adjacent the curvate pocket 2112, and preferably in the circumferential wall 2114 as shown.

As shown in FIGS. 10*a* to 10*e*, second baseplate 2100 is similarly designed as second baseplate 1500 and includes an outwardly-facing surface 2102 having a convex dome 2103 and a plurality of spikes 2105 that may act as vertebral body contact elements. The second baseplate 2100 also includes and inwardly-facing surface 2108 and a curvate pocket 2112 formed by a central portion of the inwardly-facing surface 2108 concaving outwardly with the semispherical contour. Preferably, as shown, the curvet pocket 2112 is surrounded by a circumferential wall 2114 and a circumferential recess 2116 that operates similarly to the circumferential wall and circumferential recess 1514 and 1516, respectively.

Referring now to FIGS. 10*f–j*, a third type 2200 of ball of the fourth embodiment family is shown in top (FIG. 10*f*), side (FIG. 10*g*), side cutaway (FIG. 10*h*), perspective cutaway (FIG. 10*i*) and perspective (FIG. 10*j*) views. The ball 2200 is identical to the first type 1600 of ball described above and includes central bore 2202, (and thus similar features are reference numbered similar to those of the first type 1600 of ball, but in the 2200s rather than the 1600s), except that the semispherical contour of this third type 2200 of ball is also interrupted by a curvate recess 2204.

Referring now to FIGS. 10*k–o*, a third type 2300 of convex structure of the fourth embodiment family is shown in top (FIG. 10*k*), side (FIG. 10*l*), side cutaway (FIG. 10*m*), perspective cutaway (FIG. 10*n*) and perspective (FIG. 10*o*) views. This third type 2300 of convex structure is identical to the first type 1700 of convex structure described above (and thus similar features are reference numbered similar to those of the first type 1700 of convex structure, but in the 2300s rather than the 1700s), except that this third type 2300 of convex structure has a protrusion 2316 adjacent the curvate taper 2008.

As shown in FIGS. 10*k* to 10*o*, the convex structure 2300 is similarly designed to convex structure 1700 and includes an inwardly-facing surface 2306 and a central bore 2302 extending from an outwardly-facing surface 2304 of the convex structure. The bore 1702 is surrounded by a curvet taper 2308 on the outwardly-facing surface 2304 and the curvate taper 2308 is surrounded by a circumferential recess 2310 and a circumferential wall 2312. Further, the inwardly-facing surface 2306 of the convex structure 2300 has a perimeter region 2314 that faces the perimeter region 1410 of the first baseplate 1400 when the convex structure is secured to the second baseplate 2100.

Referring now to FIGS. 10*p–t*, an assembled third preferred embodiment of the fourth embodiment family is shown in top (FIG. 10*p*), side (FIG. 10*q*), side cutaway (FIG. 10*r*), perspective cutaway (FIG. 10*s*) and perspective (FIG. 10*t*) views. It can be seen that the curvate recess 2204 of the ball 2200 forms the recess described above in the discussion of the manner in which these remaining embodiments limit rotation of the ball in the socket formed by the curvate taper of the convex structure and the hemispherical contour of the curvate pocket of the second baseplate, and that the protrusion 2316 fits into the recess 2118 to serve as the protrusion described above in the same discussion. Thus, the protrusion 2316 and the recess 2204 interact in the above described manner to limit the rotation of the ball 2200 in the socket 2307. Assembly of the disc is identical to that of the first preferred embodiment of the fourth embodiment family, except that the protrusion 2316 is longitudinally aligned with the recess 2204 and the recess 2118 during assembly so that the protrusion 2316 fits into the recess 2118 to extend into the recess 2204 for interaction as described above as the ball 2200 rotates and angulates in the socket 2307.

In the fourth preferred embodiment of the fourth embodiment family of the present invention, a pin is secured in a pin hole so that the hemispherical head of the pin protrudes into the socket formed by the curvate taper of the convex structure and the hemispherical contour of the curvate pocket of the second baseplate, and interacts in the above-described manner with a semicylindrical recess formed on the ball. More particularly, this fourth preferred embodiment uses the same first baseplate 1400 of the first preferred embodiment, and the same ball 2200 and second baseplate 2100 of the fourth preferred embodiment. Referring to FIGS. 11*a–e*, a fourth type 2400 of convex structure of the fourth embodiment family is shown in top (FIG. 11*a*), side (FIG. 11*b*), side cutaway (FIG. 11*c*), perspective cutaway (FIG. 11*d*) and perspective (FIG. 11*e*) views. This fourth type 2400 of convex structure is identical to the first type 1700 of convex structure described above (and thus similar features are reference numbered similar to those of the first type 1700 of convex structure, but in the 2400s rather than the 1700s), except that this fourth type 2400 of convex structure has a lateral through hole (e.g., a pin hole 2416) and a protrusion (e.g., a pin 2418) secured in the pin hole 2416 (as shown in FIGS. 11*f–j*) and jutting into the socket 2407.

As shown in FIGS. 11*a* to 11*e*, convex structure 2400 is similarly designed to convex structure 1700 and includes an inwardly facing surface 2406 and a central bore 2402 extending from an outwardly-facing surface 2404 of the convex structure 2400 to an inwardly-facing surface 2406 of the convex structure. The bore 2402 is surrounded by a curvate taper 2408 on the outwardly-facing surface 2404 and the curvate taper is surrounded by a circumferential recess 2410 and a circumferential wall 2412. Further, the inwardly-facing surface 2406 of the convex structure 2400 has a perimeter region 2414. Convex structure 2400 also includes a pinhole 2416 that is not included in the embodiment of convex structure 1700.

Referring now to FIGS. 11*f–j*, an assembled fourth preferred embodiment of the fourth embodiment family is shown in top (FIG. 11*f*), side (FIG. 11*g*), side cutaway (FIG. 11*h*), perspective cutaway (FIG. 11*i*) and perspective (FIG. 11*j*) views. It can be seen that the curvate recess 2204 of the ball 2200 forms the recess described above in the discussion of the manner in which these remaining embodiments limit rotation of the ball in the socket formed by the curvate taper of the convex structure and the hemispherical contour of the curvate pocket of the second baseplate, and that the head of the pin 2418 serves as the protrusion described above in the same discussion. Thus, the head of the pin 2418 and the recess 2204 interact in the above described manner to limit the rotation of the ball 2200 in the socket 2407. Assembly of the disc is identical to that of the first preferred embodiment of the fourth embodiment family, except that the head of the pin 2418 is longitudinally aligned with the recess 2204 and the recess 2118 during assembly so that the head of the pin 2418 fits into the recess 2118 to extend into the recess 2204 for interaction as described above as the ball 2200 rotates and angulates in the socket 2407.

In the fifth preferred embodiment of the fourth embodiment family of the present invention, a ball bearing protrudes into the socket formed by the curvate taper of the convex structure and the hemispherical contour of the curvate pocket of the second baseplate, and interacts in the above-described manner with a recess formed on the ball. More particularly, this fifth preferred embodiment uses the same first baseplate 1400 of the first preferred embodiment, and the same second baseplate 2100 of the third preferred embodiment. Referring to FIGS. 12*a–e*, a fifth type 2500 of convex structure of the fourth embodiment family is shown in top (FIG. 12*a*), side (FIG. 12*b*), side cutaway (FIG. 12*c*), perspective cutaway (FIG. 12*d*) and perspective (FIG. 12*e*) views. This fifth type 2500 of convex structure is identical to the first type 1700 of convex structure described above (and thus similar features are reference numbered similar to those of the first type 1700 of convex structure, but in the 2500s rather than the 1700s), except that this fifth type 2500 of convex structure has a has a recess 2516 adjacent the curvate taper 2508.

As shown in FIGS. 11*a* to 11*e*, convex structure 2500 is similarly designed to convex structure 1700 and includes an inwardly facing surface 2406 and a central bore 2502 extending from an outwardly-facing surface 2504 of the convex structure 2500 to an inwardly-facing surface 2506 of the convex structure. The bore 2502 is surrounded by a curvate taper 2408 on the outwardly-facing surface 2504 and the curvate taper is surrounded by a circumferential recess 2510 and a circumferential wall 2512. Further, the inwardly-facing surface 2506 of the convex structure 2500 has a perimeter region 2514.

Referring to FIGS. 12*f–j*, a fourth type of ball 2700 of the fourth embodiment family is shown in top (FIG. 12*f*), side (FIG. 12*g*), side cutaway (FIG. 12*h*), perspective cutaway (FIG. 12*i*) and perspective (FIG. 12*j*) views. The ball 2700 is identical to the first type 1600 of ball described above and includes a central bore 2702, (and thus similar features are reference numbered similar to those of the first type 1600 of ball, but in the 2700s rather than the 1600s), except that the semispherical contour of this third type 2700 of ball is also interrupted by a curvate recess 2704.

Referring now to FIGS. 12*k–o*, an assembled fifth preferred embodiment of the fourth embodiment family is shown in top (FIG. 12*k*), side (FIG. 12*l*), side cutaway (FIG. 12*m*), perspective cutaway (FIG. 12*n*) and perspective (FIG. 12*o*) views. A ball bearing 2600 of the fourth embodiment family is captured for free rotation and angulation, with one part of the ball bearing 2600 closely accommodated in the recesses 2118,2516, and another part of the ball bearing 2600 protruding into the socket to interact with the curvate recess 2704 of the ball 2700. It can be seen that the curvate recess 2704 of the ball 2704 forms the recess described above in the discussion of the manner in which these remaining embodiments limit rotation of the ball in the socket, and that the ball bearing 2600 serves as the protrusion described above in the same discussion. Thus, the ball bearing 2600 and the recess 2704 interact in the above described manner to limit the rotation of the ball 2700 in the socket 2507. Assembly of the disc is identical to that of the first preferred embodiment of the fourth embodiment family, except that the recess 2704 is aligned with the curvate recess 2118 during assembly so that the ball bearing 2600 can be and is then placed into the recesses 2118,2704 (and then captured in the recess 2118 by the recess 2516 of the convex structure 2500) for interaction as described above as the ball 2700 rotates and angulates in the socket 2507.

While there has been described and illustrated specific embodiments of an artificial disc, it will be apparent to those skilled in the art that variations and modifications are possible without deviating from the broad spirit and principle of the invention. The invention, therefore, shall not be limited to the specific embodiments discussed herein.

What is claimed is:

1. An intervertebral spacer device, comprising:
   a first baseplate having an outwardly facing surface and an inwardly facing surface, the inwardly facing surface having a central hole;
   a second baseplate having an outwardly facing surface and an integrated convex structure, the convex structure including a curvate pocket, the convex structure's curvate pocket being formed by a central portion of an outwardly facing surface of the convex structure concaving inwardly to define a semispherical contour, the convex structure's curvate pocket further having an apex at a center of the convex structure's curvate pocket's semispherical contour, the convex structure further having a bore through the convex structure's curvate pocket's apex from the convex structure's outwardly facing surface to the convex structure's inwardly facing surface, the second baseplate having on its outwardly facing surface an access hole leading to the convex structure's curvate pocket;
   a post having a longitudinal axis, a tail end, and a head end having a ball defining a spherical contour;
   a cap having an inwardly facing surface and a curvate pocket having a semispherical contour, the cap's curvate pocket being formed by a central portion of the cap's inwardly facing surface concaving outwardly, wherein the axis hole is surrounded by a circular recess, and the cap is securable to the circular recess;
   wherein the tail end of the post is disposable through the access hole and through the bore, and the head end of the post is disposable through the access hole and prevented from passage through the bore, such that the ball is seatable in the convex structure's curvate pocket wherein the tail end is securable in the central hole; and wherein the cap is securable to the second baseplate such that the cap's curvate pocket's semispherical contour opposes the convex structure's curvate pocket's semispherical contour such that the semispherical contours together define a curvate socket defining a spherical contour that closely accommodates the ball's spherical contour for rotation and angulation of the ball in the curvate socket about a central portion of the ball, and such that the post is accommodated for rotation in the bore about the longitudinal axis as the ball rotates in the curvate socket, and such that the post is accommodated for angulation in the bore about the ball's central portion as the ball angulates in the curvate socket.

2. The intervertebral spacer device of claim 1, wherein the inwardly facing surface of the first baseplate and the inwardly facing surface of the convex structure each has a respective perimeter region, and the perimeter regions have corresponding contours that reduce surface wearing during rotation and angulation of the ball in the curvate socket.

3. The intervertebral spacer device of claim 1, wherein the cap is compression lockable to the second baseplate.

4. The intervertebral spacer device of claim 1, wherein the bore is tapered to a larger diameter toward the convex structure's inwardly facing surface, and the post is accommodated by the bore being tapered for angulation in the bore about the ball's central portion as the ball angulates in the curvate socket.

5. The intervertebral spacer device of claim 1, wherein at least one of the curvate pockets has a hemispherical contour.

6. The intervertebral spacer device of claim 1, wherein the cap has an outwardly facing surface and at least one of the cap and the first baseplate includes an osteoconductive vertebral body contact surface on its outwardly facing surface.

7. The intervertebral spacer device of claim 1, wherein the tail end is compression lockable into the central hole.

8. An intervertebral spacer device, comprising:
a first baseplate having an outwardly facing surface and an inwardly facing surface, the inwardly facing surface having a central post secured thereto, the post having a longitudinal axis and a ball at a head end of the post, the ball defining a spherical contour;
a second baseplate having an outwardly facing surface and an inwardly facing surface, the second baseplate including a convex structure integral therewith and a cap secured thereto, the convex structure and the cap together establishing a curvate socket communicating with a central bore through the convex structure, the curvate socket defining a spherical contour, the head of the post being inwardly directed toward the second baseplate;
wherein the ball is capturable in the curvate socket, with the curvate socket's spherical contour accommodating the ball's spherical contour for rotation and angulation of the ball in the curvate socket about a central portion of the ball;
wherein the central bore accommodates the post for rotation in the central bore about the longitudinal axis as the ball rotates in the curvate socket, and accommodates the post for angulation in the central bore about the ball's central portion as the ball angulates in the curvate socket; and
wherein each of the convex structure and the cap has a respective curvate pocket, the second baseplate has an access hole leading to the convex structure's curvate pocket and accommodating passage of the post and the ball for seating of the ball in the convex structure's curvate pocket with the post disposed in the central bore, and the cap is secured to the second baseplate such that the curvate pockets of the convex structure and the cap oppose one another to define the curvate socket, wherein the axis hole is surrounded by a circular recess, and the cap is secure to the circular recess.

9. The intervertebral spacer device of claim 8, wherein the cap is compression locked to the second baseplate.

10. The intervertebral spacer device of claim 8, wherein at least one of the curvate pockets has a hemispherical contour.

11. The intervertebral spacer device of claim 8, wherein the central bore is tapered to a larger diameter toward the second baseplate's inwardly facing surface, and the post is accommodated by the central bore being tapered for angulation in the central bore about the ball's central portion as the ball angulates in the curvate socket.

* * * * *